US008231876B2

(12) United States Patent
Wan et al.

(10) Patent No.: US 8,231,876 B2
(45) Date of Patent: Jul. 31, 2012

(54) PURIFIED ANTIBODY COMPOSITION

(75) Inventors: Min M. Wan, Worcester, MA (US);
George Avgerinos, Sudbury, MA (US);
Gregory Zarbis-Papastoitsis,
Watertown, MA (US)

(73) Assignee: Abbott Biotechnology Ltd., Hamilton (BM)

( * ) Notice: Subject to any disclaimer, the term of this patent is extended or adjusted under 35 U.S.C. 154(b) by 0 days.

(21) Appl. No.: 12/882,601

(22) Filed: Sep. 15, 2010

(65) Prior Publication Data
US 2011/0002935 A1 Jan. 6, 2011

Related U.S. Application Data

(62) Division of application No. 11/732,918, filed on Apr. 4, 2007, now Pat. No. 7,863,426.

(60) Provisional application No. 60/789,725, filed on Apr. 5, 2006, provisional application No. 60/790,414, filed on Apr. 6, 2006.

(51) Int. Cl.
*A61K 39/395* (2006.01)
*C07K 16/00* (2006.01)

(52) U.S. Cl. .......... 424/142.1; 424/158.1; 424/176.1; 424/177.1; 530/388.15; 530/388.23; 530/390.1; 530/390.5; 530/416

(58) Field of Classification Search .................. None
See application file for complete search history.

(56) References Cited

U.S. PATENT DOCUMENTS

| 5,110,913 | A | 5/1992 | Coan et al. |
|---|---|---|---|
| 5,118,796 | A | 6/1992 | Prior et al. |
| 5,231,024 | A | 7/1993 | Moeller et al. |
| 5,429,746 | A | 7/1995 | Shadle et al. |
| 5,654,407 | A | 8/1997 | Boyle et al. |
| 5,656,272 | A | 8/1997 | Le et al. |
| 5,672,347 | A | 9/1997 | Aggarwal et al. |
| 5,795,967 | A | 8/1998 | Aggarwal et al. |
| 5,859,205 | A | 1/1999 | Adair et al. |
| 5,877,293 | A | 3/1999 | Adair et al. |
| 5,929,212 | A | 7/1999 | Jolliffe et al. |
| 5,945,098 | A | 8/1999 | Sarno et al. |
| 5,994,510 | A | 11/1999 | Adair et al. |
| 6,024,938 | A | 2/2000 | Corbo et al. |
| 6,090,382 | A | 7/2000 | Salfeld et al. |
| 6,171,586 | B1 | 1/2001 | Lam et al. |
| 6,258,562 | B1 | 7/2001 | Salfeld et al. |
| 6,448,380 | B2 | 9/2002 | Rathjen et al. |
| 6,451,983 | B2 | 9/2002 | Rathjen et al. |
| 6,489,447 | B1 | 12/2002 | Basey et al. |
| 6,498,237 | B2 | 12/2002 | Rathjen et al. |
| 6,509,015 | B1 | 1/2003 | Salfeld et al. |
| 6,593,458 | B1 | 7/2003 | Rathjen et al. |
| 6,870,034 | B2 | 3/2005 | Breece et al. |
| 7,070,775 | B2 | 7/2006 | Le et al. |
| 7,122,641 | B2 * | 10/2006 | Vedantham et al. .......... 530/413 |
| 7,223,394 | B2 | 5/2007 | Salfeld et al. |
| 7,250,165 | B2 | 7/2007 | Heavner et al. |
| 7,276,239 | B2 | 10/2007 | Le et al. |
| 7,541,031 | B2 | 6/2009 | Salfeld et al. |
| 7,588,761 | B2 | 9/2009 | Salfeld et al. |
| 7,714,112 | B2 * | 5/2010 | Engstrand et al. .......... 530/390.5 |
| 7,750,129 | B2 * | 7/2010 | Johansson et al. ............ 530/413 |
| 7,863,426 | B2 | 1/2011 | Wan et al. |
| 7,919,264 | B2 | 4/2011 | Maksymowych et al. |
| 2003/0012786 | A1 | 1/2003 | Teoh et al. |
| 2003/0049725 | A1 | 3/2003 | Heavner et al. |
| 2003/0125247 | A1 | 7/2003 | Rosen et al. |
| 2003/0161828 | A1 | 8/2003 | Abdelghany et al. |
| 2003/0166869 | A1 * | 9/2003 | Vedantham et al. ....... 530/387.1 |
| 2003/0206898 | A1 | 11/2003 | Fischkoff et al. |
| 2003/0219438 | A1 | 11/2003 | Salfeld et al. |
| 2003/0229212 | A1 | 12/2003 | Fahrner et al. |
| 2003/0235585 | A1 | 12/2003 | Fischkoff et al. |
| 2004/0009172 | A1 | 1/2004 | Fischkoff et al. |
| 2004/0033228 | A1 | 2/2004 | Krause et al. |
| 2004/0120952 | A1 | 6/2004 | Knight et al. |
| 2004/0126372 | A1 | 7/2004 | Banerjee et al. |
| 2004/0126373 | A1 | 7/2004 | Banerjee et al. |
| 2004/0131614 | A1 | 7/2004 | Banerjee et al. |
| 2004/0136989 | A1 | 7/2004 | Banerjee et al. |
| 2004/0136990 | A1 | 7/2004 | Banerjee et al. |
| 2004/0136991 | A1 | 7/2004 | Banerjee et al. |
| 2004/0151722 | A1 | 8/2004 | Banerjee et al. |
| 2004/0166111 | A1 | 8/2004 | Kaymakcalan et al. |
| 2004/0219142 | A1 | 11/2004 | Banerjee et al. |
| 2005/0123541 | A1 | 6/2005 | Heavner et al. |

(Continued)

FOREIGN PATENT DOCUMENTS

CN  1563090 A  1/2005

(Continued)

OTHER PUBLICATIONS

Abraham, E., et al., "Efficacy and Safety of Monoclonal Antibody to Human Tumor Necrosis Factor α in Patients with Sepsis Syndrome," *JAMA*, vol. 273(12):934-941 (1995). Barbuto, J. et al. "Production of Neutralizing Antibodies to Tumor Necrosis Factor by Human Tumor-Infiltrating B Lymphocytes" *Proc. Am. Assoc. Cancer Res*,. 34:487, Abstr. 2904 (1993).
Bendtzen, K. et al. "Auto-antibodies to IL-1α and TNFα in Normal Individuals and in Infectious and Immunoinflammatory Disorders" *The Physiological and Pathological Effects of Cytokines*, 447-52 (1990).
Boekstegers, P., et al., "Repeated administration of a F(ab')2 fragment of an anti-tumor necrosis factor alpha monoclonal antibody in patients with severe sepsis: effects on the cardiovascular system and cytokine levels," *Shock*, vol. 1(4):237-245 (1994).
Boyle, P. et al. "A Novel Monoclonal Human IgM Autoantibody which Binds Recombinant Human and Mouse Tumor Necrosis Factor-α" *Cell. Immunol*, 152:556-68 (1993).
Boyle, P. et al. "The B5 Monoclonal Human Autoantibody Binds to Cell Surface TNFα on Human Lymphoid Cells and Cell Lines and Appears to Recognize a Novel Epitope" *Cell. Immunol.*, 152:569-81 (1993).
Brekke, O. et al., "Therapeutic Antibodies for Human Diseases at the Dawn of the Twenty-first Century," *Nature*, vol. 2:52-62 (2002).

(Continued)

*Primary Examiner* — David A Saunders
(74) *Attorney, Agent, or Firm* — McCarter & English LLP; Cristin H. Cowles; Christopher B. Westberg

(57) ABSTRACT

The invention provides a method for producing a host cell protein-(HCP) reduced antibody preparation from a mixture comprising an antibody and at least one HCP, comprising an ion exchange separation step wherein the mixture is subjected to a first ion exchange material, such that the HCP-reduced antibody preparation is obtained.

13 Claims, 6 Drawing Sheets

U.S. PATENT DOCUMENTS

| | | | |
|---|---|---|---|
| 2005/0249735 | A1 | 11/2005 | Le et al. |
| 2005/0271654 | A1 | 12/2005 | Rinderknecht et al. |
| 2006/0009385 | A1 | 1/2006 | Hoffman et al. |
| 2006/0018907 | A1 | 1/2006 | Le et al. |
| 2006/0083741 | A1 | 4/2006 | Hoffman et al. |
| 2006/0153846 | A1 | 7/2006 | Krause et al. |
| 2006/0246073 | A1 | 11/2006 | Knight et al. |
| 2007/0003548 | A1 | 1/2007 | Heavner et al. |
| 2007/0041905 | A1 | 2/2007 | Hoffman et al. |
| 2007/0071747 | A1 | 3/2007 | Hoffman et al. |
| 2007/0081996 | A1 | 4/2007 | Hoffman et al. |
| 2007/0202104 | A1 | 8/2007 | Banerjee et al. |
| 2007/0298040 | A1 | 12/2007 | Le et al. |
| 2008/0025976 | A1 | 1/2008 | Le et al. |
| 2008/0118496 | A1 | 5/2008 | Medich et al. |
| 2008/0131374 | A1 | 6/2008 | Medich et al. |
| 2008/0166348 | A1 | 7/2008 | Kupper et al. |
| 2008/0193466 | A1 | 8/2008 | Banerjee et al. |
| 2008/0227136 | A1 | 9/2008 | Pla et al. |
| 2008/0311043 | A1 | 12/2008 | Hoffman et al. |
| 2009/0017472 | A1 | 1/2009 | Stuhlmuller et al. |
| 2009/0028794 | A1 | 1/2009 | Medich et al. |
| 2009/0110679 | A1 | 4/2009 | Li et al. |
| 2009/0123378 | A1 | 5/2009 | Wong et al. |
| 2009/0148513 | A1 | 6/2009 | Fraunhofer et al. |
| 2009/0155205 | A1 | 6/2009 | Salfeld et al. |
| 2009/0226530 | A1 | 9/2009 | Lassner et al. |
| 2009/0239259 | A1 | 9/2009 | Hsieh et al. |
| 2009/0258018 | A1 | 10/2009 | Medich et al. |
| 2009/0271164 | A1 | 10/2009 | Peng et al. |
| 2009/0280065 | A1 | 11/2009 | Willian et al. |
| 2009/0291062 | A1 | 11/2009 | Fraunhofer et al. |
| 2009/0304682 | A1 | 12/2009 | Hoffman et al. |
| 2009/0317399 | A1 | 12/2009 | Pollack et al. |
| 2010/0003243 | A1 | 1/2010 | Okun et al. |
| 2010/0016557 | A1 | 1/2010 | Salfeld et al. |
| 2010/0021451 | A1 | 1/2010 | Wong et al. |
| 2010/0034823 | A1 | 2/2010 | Borhani et al. |
| 2010/0040604 | A1 | 2/2010 | Salfeld et al. |
| 2010/0040630 | A1 | 2/2010 | Elden et al. |
| 2010/0160894 | A1 | 6/2010 | Julian et al. |
| 2010/0278822 | A1 | 11/2010 | Fraunhofer et al. |
| 2011/0054414 | A1 | 3/2011 | Shang et al. |

FOREIGN PATENT DOCUMENTS

| | | |
|---|---|---|
| EP | 0101681 B1 | 3/1984 |
| EP | 0186833 B1 | 7/1986 |
| EP | 0212489 B1 | 3/1987 |
| EP | 0351789 B1 | 1/1990 |
| EP | 0366043 B1 | 5/1990 |
| EP | 0492448 B1 | 7/1992 |
| EP | 0614984 B1 | 9/1994 |
| EP | 0659766 A1 | 6/1995 |
| EP | 1174148 A1 | 1/2002 |
| EP | 1254666 A1 | 11/2002 |
| GB | 2279077 | 12/1994 |
| WO | WO 91/02078 A1 | 2/1991 |
| WO | WO 92/11383 A1 | 7/1992 |
| WO | WO 92/16553 A1 | 10/1992 |
| WO | WO 93/06213 A1 | 4/1993 |
| WO | WO 94/29347 A1 | 12/1994 |
| WO | WO 95/23813 A1 | 9/1995 |
| WO | WO 96/33208 A1 | 10/1996 |
| WO | WO 97/04801 A1 | 2/1997 |
| WO | WO 98/56418 A1 | 12/1998 |
| WO | WO 99/57134 A1 | 11/1999 |
| WO | WO 01/47554 A1 | 7/2001 |
| WO | WO 02/012502 A3 | 2/2002 |
| WO | WO 2005/082483 A1 * | 9/2005 |
| WO | WO 2006/043895 A1 * | 4/2006 |

OTHER PUBLICATIONS

Chow, A et al. "Effect of monoclonal antibody on human tumor necrosis factor (TNF MAb) on TNFα, IL-1β, and IL-6 levels in patients with sepsis syndrome" Clinical Research, 42:2 299A (1994).

Cleland, J. et al., "A Specific Molar Ratio of Stabilizer to Protein is Required for Storage Stability of a Lyophilized Monoclonal Antibody," Journal of Pharmaceutical Sciences, vol. 90(3):310-321 (2001).

Cohen, J., et al., "Intersept: An international, multicenter, placebo-controlled trial of monoclonal anitbody to human tumor necrosis factor-α in patients with sepsis," Crit Care Med, vol. 24(9):1431-1440 (1996).

Cox, J. et al. "A directory of human germ-line $V_k$ segments reveals a strong bias in their usage" Eur. J. Immunol., 24(2):827-36 (1994).

Elliott, M. et al. "Treatment of rheumatoid arthritis with chimeric monoclonal antibodies to tumor necrosis factor α" Arthritis & Rheumatism, 36(12):1681-90 (1993).

Emery, P. "Adalimumab therapy: Clinical findings and implications for integration into clinical guidelines for rheumatoid arthritis." Drugs of Today, 41(3): p. 155-153. (2005).

Feldmann, M. et al., "Anti-TNFα Therapy of Rheumatoid Arthritis: What Have We Learned," Annu. Rev. Immunol., vol. 19:163-196 (2001).

Figini, M. et al., "In Vitro Assembly of Repertoires of Antibody Chains on the Surface of Phage by Renaturation," J. Mol. Biol., vol. 239:68-78 (1994).

Fomsgaard, A. et al. "Auto-antibodies to Tumour Necrosis Factor α in Healthy Humans and Patients with Inflammatory Diseases and Gram-Negative Bacterial Infections" Scand. J. Immunol., 30:219-23 (1989).

Foote, J. et al., "Antibody Framework Residues Affecting the Conformation of the Hypervariable Loops," J. Mol. Biol., vol. 224:487-499 (1992).

Graf et al., "Ion exchange resins for the purification of monoclonal antibodies from animal cell culture" Bioseparation 4 (1) :7-20 (Feb. 1994). ;4 (1) :7-20 (Feb. 1994).

Griffiths, A.D. et al. "Human anti-self antibodies with high specificity from phage display libraries" The EMBO J., 12(2):725-34 (1993).

Hawkins, R. et al., "Selection of Phage Antibodies by Binding Affinity Mimicking Affinity Maturation," J. Mol. Biol., vol. 226:889-896 (1992).

Hillgren, A. et al., "Protection mechanism of Tween 80 during freeze-thawing of a model protein LDH," International Journal of Pharmaceutics, vol. 237:57-69 (2002).

Holler, E. et al., "Modulation of Acute Graft-Versus-Host Disease After Allogeneic Bone Marrow Transplantation by Tumor Necrosis Factor α (TNFα) Release in the Course of Pretransplant Conditioning: Role of Conditioning Regimens and Prophylactic Application of a Monoclonal Antibody Neutralizing Human TNFα (MAK 195F)," Blood, vol. 86(3):890-899 (1995).

Holt, L. et al., "Domain antibodies: proteins for therapy," Trends in Biotechnology, vol. 21(11):484-490 (2003).

Hoogenboom, H. et al., "Converting rodent into human antibodies by guided selection," Antibody Engineering, Oxford University Press, Chpt. 8, pp. 169-185 (1996).

Huse, W.D. et al. "Generation of a large combinatorial library of the immunoglobulin repertoire in phage lambda" Science, 246:1275-81 (1989).

Jespers, L. et al., "Guiding the Selection of Human Antibodies from Phage Display Repertoires to a Single Epitope of an Antigen," Bio/Technology, vol. 12:899-903 (1994).

Kalyanpur, M., "Downstream Processing in the Biotechnology Industry" Molecular Biotechnology, vol. 22:87-98 (2002).

Kempeni, J, "Preliminary results of early clinical trials with the fully human anti-TNFα monoclonal antibody D2E7", Ann. Rheum. Dis., 1999, pp. 170-172, vol. 58, (Suppl. I).

Kempeni, J., "Update on D2E7: a fully human anti-tumour necrosis factor α monoclonal antibody," Ann. Rheum. Dis., vol. 59(Suppl. 1):144-145 (2000).

Lerner, R.A. et al. "Antibodies without immunization" Science, 258:1313-14 (1992).

Leusch, H-G. et al. "Failure to demonstrate TNFα-specific autoantibodies in human sera by Elisa and Western blot" J. ImmunoL Methods, 139:145-47 (1991).

Lewis et aL "Use of alanine scanning mutagenesis to improve the affinity of an anti gp120 (HIV) antibody." J. Cell. Biochem., 18D:215 (1994).

Low, N. et al., "Mimicking Somatic Hypermutation: Affinity Maturation of Antibodies Displayed on Bacteriophage Using a Bacterial Mutator Strain," *J. Mol. Biol.*, vol. 260:359-368 (1996).

Low, N., thesis extract, Cambridge University (1996).

Marks, J.D. et al. "By-passing immunization: Human antibodies from V-gene libraries displayed on phage" *J. Mol. Biol.* 222:581-97 (1991).

Medynski, D., "Phage Display: All Dressed Up and Ready to Role," *Bio/Technology*, vol. 12:1134-1136 (1994).

Möller, A. et al. "Monoclonal antibodies to human tumor necrosis factor α: in vitro and vivo application" *Cytokine*, 2(3):162-69 (1990).

Nilsson, B., "Antibody engineering," *Current Opinion in Structural Biology*, vol. 5:450-456 (1995).

Osbourn, J. et al., "From rodent reagents to human therapeutics using antibody guided selection," *Methods*, vol. 36:61-68 (2005).

Queen, C. et al., "A humanized antibody that binds to the interleukin 2 receptor," *Proc. Natl. Acad. Sci. USA*, vol. 86:10029-10033 (1989).

Reinhart, K. et al., "Assessment of the safety and efficacy of the monoclonal anti-tumor necrosis factor antibody-fragment, MAK 195F, in patients with sepsis and septic shock: A multicenter, randomized, placebo-controlled, dose-ranging study," *Crit. Care. Med.*, vol. 24(5):733-742 (1996).

Riechmann, L. et al., "Phage Display and Selection of a Site-Directed Randomized Single-Chain Antibody Fv Fragment for Its Affinity Improvement," *Biochemistry*, vol. 32:8848-8855 (1993).

Santora, L. et al., "Characterization of Noncovalent Complexes of Recombinant Human Monoclonal Antibody and Antigen Using Carbon Exchange, Size Exclusion Chromatography, and BIAcore," *Analytical Biochemistry*, vol. 299(2):119-129 (2001).

Thompson, J. et al., "Affinity Maturation of a High-affinity Human Monoclonal Antibody Against the Third Hypervariable Loop of Human Immunodeficiency Virus: Use of Phage Display to Improve Affinity and Broaden Strain Reactivity," *J. Mol. Biol.*, vol. 256:77-88 (1996).

Tomlinson, I. et al., "The Repertoire of Human Germline $V_H$ Sequences Reveals about Fifty Groups of $V_H$ Segments with Different Hypervariable Loops," *J. Mol. Biol.*, vol. 227:776-798 (1992).

Tomlinson, I. et al., "The structural repertoire of the human $V_k$ domain," *The EMBO Journal*, vol. 14(18):4628-4638 (1995).

Tracey, K. et al., "Tumor Necrosis Factor: A Pleiotropic Cytokine and Therapeutic Target," *Annu. Rev. Med.*, vol. 45:491-503 (1994).

Van Der Poll, T. et al., "Effect of postponed treatment with an anti-tumour necrosis factor (TNF) F(ab')2 fragment on endotoxin-induced cytokine and neutrophil responses in chimpanzees," *Clin. Exp. Immunol.*, vol. 100:21-25 (1995).

Vaughan, T. et al., "Human antibodies by design," *Nature Biotechnology*, vol. 16:535-539 (1998).

Ward, E. et al., "Binding activities of a repertoire of single immunoglobulin variable domains secreted from *Escherichia coli*," Nature, vol. 341:544-546 (1989).

Winter, G. et al., "Humanized antibodies," *Immunology Today*, vol. 14(6):243-246 (1993).

Winter, G. et al., "Making Antibodies by Phage Display Technology," *Annu. Rev. Immunol.*, vol. 12:433-455 (1994).

Kempf, C, et al. "Virus inactivation during production of intravenous immunoglobulin." *Transfusion* 1991; vol. 31: p. 423-427.

Gonzalez et al. "Purification of Lactic Acid from Fermentation Broths by Ion-Exchange Resins" *Ind. Eng. Chem. Res.* 45:3243 (2006).

Department of Surgery, University of Toronto, Annual Report (1998-1999).

International Search Report for Application No. PCT/IB03/04502, dated May 26, 2004.

Li, F. et al., "Current Therapeutic Antibody Production and Process Optimization" *BioProcessing Journal*, vol. 4(5):23-30 (2005).

International Preliminary Report on Patentability for PCT/US07/08359, dated Dec. 12, 2011.

Gagnon et al., "A Systematic Approach to the Purification of Monoclonal Antibodies" *LC-GC* 11(1):26-34 (1993).

Graf et al., "Ion exchange resins for the purification of monoclonal antibodies from animal cell culture" *Bioseparation* 4:7-20 (1994).

\* cited by examiner

PURIFIED ANTIBODY COMPOSITION

RELATED APPLICATIONS

This application is a divisional of U.S. patent application Ser. No. 11/732,918, filed Apr. 4, 2007, now U.S. Pat. No. 7,863,426, which claims priority to U.S. provisional application Ser. No. 60/789,725, filed on Apr. 5, 2006 and to U.S. provisional application Ser. No. 60/790,414, filed on Apr. 6, 2006, the contents of each of which are hereby incorporated in their entirety.

BACKGROUND OF THE INVENTION

Large-scale, economic purification of proteins is increasingly an important problem for the biotechnology industry. Generally, proteins are produced by cell culture, using either mammalian or bacterial cell lines engineered to produce the protein of interest by insertion of a recombinant plasmid comprising the gene for that protein. Since the cell lines used are living organisms, they must be fed with a complex growth medium, comprising sugars, amino acids, and growth factors, usually supplied from preparations of animal serum. Separation of the desired protein from the mixture of compounds fed to the cells and from the by-products of the cells themselves to a purity sufficient for use as a human therapeutic poses a formidable challenge.

SUMMARY OF THE INVENTION

There is a need for improved methods of obtaining antibody preparations comprising a reduced amount of host cell protein, including procathepsin L. The invention provides a method for purifying antibodies expressed in a host cell expression system, wherein the resulting antibody preparation comprises a reduced amount of host cell protein, including procathepsin L. The improved method of the invention also includes the the development of reproducible methods of accurately detecting host cell proteins, and a kinetic assay The invention provides a method for producing a host cell protein-(HCP) reduced antibody preparation from a mixture comprising an antibody and at least one HCP, comprising an ion exchange separation step wherein the mixture is subjected to a first ion exchange material, such that the HCP-reduced antibody preparation is obtained. In one embodiment, the ion exchange separation step comprises passing the mixture over the first ion exchange material such that a first eluate having a reduced level of HCP is obtained. In one embodiment, the method of the invention further comprises a second ion exchange separation step wherein the first eluate is subjected to a second ion exchange material such that a first flowthrough having a reduced level of HCP is obtained. In another embodiment, the method of the invention further comprises a hydrophobic interaction separation step wherein the first flowthrough is subjected to a first hydrophobic interaction material such that a second eluate having a reduced level of HCP is obtained.

In one embodiment of the invention, the ion exchange separation step comprises a first ion exchange chromatography step, wherein the mixture is loaded onto a column comprising the first ion exchange material, such that a first eluate having a reduced level of HCP is obtained. In one embodiment, the invention further comprises a second ion exchange chromatography step comprising loading the first eluate onto a column comprising a second ion exchange material, such that a first flowthrough is obtained.

In one embodiment, the invention further comprises a hydrophobic interaction separation step comprising loading the first flowthrough onto a column comprising a first hydrophobic interaction material, such that a second eluate is obtained. In one embodiment, the hydrophobic interaction separation step comprises hydrophobic interaction chromatography. In one embodiment, the hydrophobic interaction chromatography is phenyl sepharose chromatography. In still another embodiment, the amount of antibody loaded on to the hydrophobic interaction material ranges from about 20 to about 40 grams of antibody per liter of hydrophobic interaction material. In yet another embodiment, the amount of antibody loaded on to the hydrophobic interaction material ranges from about 30 to about 36 grams of antibody per liter of hydrophobic interaction material.

In one embodiment, the ion exchange chromatography step is cation exchange chromatography. In another embodiment, the cation exchange chromatography is a synthetic methacrylate based polymeric resin attached to a sulfonate group. In still another embodiment, the invention further comprises washing the ion exchange material with a plurality of wash steps. In one embodiment, the plurality of wash steps comprises an increase in conductivity. In one embodiment, the ion exchange material is washed with a wash comprising about 40-50% elution buffer and about 50-60% water (e.g., water for injection (WFI)). In one embodiment, the elution buffer is 20 mM $Na_2PO_4$, 150 mM sodium chloride, pH 7.

In one embodiment, the first eluate is subjected to viral inactivation prior to the first ion exchange chromatography step. In one embodiment, the viral inactivation is achieved through pH viral inactivation (e.g., lower the pH of the first eluate to thereby inactivate viruses).

In one embodiment of the invention, the second ion exchange chromatography step comprises anion exchange chromatography. In one embodiment, the anion exchange chromatography is Q sepharose chromatography.

The invention also provides a method method for producing a host cell protein-(HCP) reduced antibody preparation from a mixture comprising an antibody and at least one HCP, wherein the reduced level of HCP is achieved by altering the pH and conductivity of the first eluate such that the pH and conductivity of the first eluate is substantially similar to the pH and conductivity of the second ion exchange material. In one embodiment, the pH of the second ion exchange material ranges from about 7.7 to about 8.3. In another embodiment, the pH of the first eluate is altered to range from about 7.7 to about 8.3. In still another embodiment, the pH of the first eluate is altered to about 8.0. In one embodiment, the conductivity of the second ion exchange material ranges from about 3.5 mS/cm to about 5.2 mS/cm, or from about 3.5 mS/cm to about 4.9 mS/cm. In one embodiment, the conductivity of the first eluate is altered to range from about 3.5 mS/cm to about 5.2 mS/cm or from about 3.5 mS/cm to about 4.9 mS/cm.

In one embodiment of the invention, the first eluate comprises a range of about 90 to about 100 fold less HCP than the mixture as determined by a HCP ELISA. In another embodiment, the first flowthrough comprises a range of about 840 to about 850 fold less HCP than the first eluate as determined by a HCP ELISA. In yet another embodiment, the second eluate comprises a range of about 3 to about 5 fold less HCP than the first flowthrough as determined by a HCP ELISA.

The invention provides a method for producing a procathepsin L-reduced antibody preparation from a mixture comprising an antibody and procathepsin L, comprising an ion exchange separation step wherein the mixture is subjected to a first ion exchange material, such that the procathepsin L-reduced antibody preparation is obtained.

In one embodiment, the ion exchange separation step comprises passing the mixture over the first ion exchange material such that a first eluate having a reduced level of procathepsin L is obtained. In one embodiment, the ion exchange separation step comprises a first ion exchange chromatography step, wherein the mixture is loaded onto a column comprising the first ion exchange material, such that a first eluate having a reduced level of procathepsin L is obtained.

In one embodiment, the invention further comprises a second ion exchange separation step wherein the first eluate is subjected to a second ion exchange material such that a first flowthrough having a reduced level of procathepsin L is obtained. In one embodiment, the invention further comprises a second ion exchange chromatography step comprising loading the first eluate onto a column comprising a second ion exchange material, such that a first flowthrough is obtained.

In one embodiment, the invention further comprises a hydrophobic interaction separation step wherein the first flowthrough is subjected to a first hydrophobic interaction material such that a second eluate having a reduced level of procathepsin L is obtained. In another embodiment, the invention further comprises a hydrophobic interaction separation step comprising loading the first flowthrough onto a column comprising a first hydrophobic interaction material, such that a second eluate is obtained.

In one embodiment, the ion exchange chromatography step is cation exchange chromatography, including, but not limited to a synthetic methacrylate based polymeric resin attached to a sulfonate group.

In another embodiment, the ion exchange chromatography step further comprises washing the ion exchange material with a plurality of wash steps. In one embodiment, the plurality of wash steps comprises an increase in conductivity. In one embodiment, the ion exchange material is washed with a wash buffer comprising about 40-50% elution buffer and about 50-60% water (e.g., water for injection (WFI)). In still another embodiment, the elution buffer is 20 mM $Na_2PO_4$, 150 mM sodium chloride, pH 7.

In one embodiment of the invention, the first eluate is subjected to viral inactivation prior to ion exchange chromatography step. In one embodiment, the viral inactivation is achieved through pH viral inactivation (e.g., lowering of the pH of the first eluate to thereby inactive viruses).

In one embodiment, the ion exchange chromatography step comprises anion exchange chromatography. In one embodiment, the anion exchange chromatography is Q sepharose chromatography.

The invention also describes a method wherein the reduced level of procathepsin L is attained by altering the pH and conductivity of the first eluate such that the pH and conductivity of the first eluate is substantially similar to the pH and conductivity of the second ion exchange material. In one embodiment, the pH of the second ion exchange material ranges from about 7.7 to about 8.3. In another embodiment the pH of the first eluate is altered to range from about 7.7 to about 8.3. In still another embodiment wherein the pH of the first eluate is altered to about 8.0. In yet another embodiment, the conductivity of the second ion exchange material ranges from about 3.5 mS/cm to about 5.2 mS/cm, or from about 3.5 mS/cm to about 4.9 mS/cm. In one embodiment, the conductivity of the first eluate is altered to range from about 3.5 mS/cm to about 5.2 mS/cm, or from about 3.5 mS/cm to about 4.9 mS/cm.

In one embodiment of the invention, the hydrophobic interaction separation step comprises hydrophobic interaction chromatography. In one embodiment, the hydrophobic interaction chromatography is phenyl sepharose chromatography. In still another embodiment, the amount of antibody loaded on to the hydrophobic interaction material ranges from about 20 to about 40 grams of antibody per liter of hydrophobic interaction material. In yet another embodiment, the amount of antibody loaded on to the hydrophobic interaction material ranges from about 30 to about 36 grams of antibody per liter of hydrophobic interaction material.

In one embodiment, the first eluate comprises cathepsin L activity ranging from between about 25 to about 60 RFU/s/mg of antibody as measured by a cathepsin L kinetic assay.

In another embodiment, the first flowthrough comprises cathepsin L activity ranging from between about 0.4 to about 4 RFU/s/mg of antibody as measured by a cathepsin L kinetic assay.

In still another embodiment, the second eluate comprises cathepsin L activity ranging from between about 0.5 to about 1.5 RFU/s/mg of antibody as measured by a cathepsin L kinetic assay.

In one embodiment of the invention, the level of procathepsin L is reproducibly low.

In a particularly preferred aspect, the invention provides antibody purification methods in which high amounts of an antibody-HCP mixture can be loaded onto an ion exchange resin to achieve reduction in HCP in the mixture. This methodology has the advantage that it can be used with antibody-HCP mixtures that have not been subjected to protein A capture prior to application of the antibody-HCP mixture to the ion exchange resin. Protein A capture, in which an antibody-HCP mixture is applied to a protein A column such that the antibody binds to protein A and HCPs flow through, typically is used as an initial purification step in antibody purification procedures as a means to remove HCPs. Thus, the methods of the invention are useful for purifying large loads of antibody-HCP mixtures without the need to carry out a protein A chromatography as an initial step.

Thus, in one embodiment, the invention provides a method for producing a host cell protein-(HCP) reduced antibody preparation from a mixture comprising an antibody and at least one HCP, the method comprising:

(a) applying the mixture to a first ion exchange resin in an equilibration buffer, wherein greater than 30 grams of antibody per liter of resin are applied;

(b) washing HCP from the resin with a plurality of wash steps; and (c) eluting the antibody from the resin with an elution buffer to form a first eluate, such that the HCP-reduced antibody preparation is obtained.

In another embodiment, about 35-70 grams of antibody per liter of resin are applied. In yet another embodiment, about 70 grams of antibody per liter of resin are applied. In a preferred embodiment, the mixture comprising an antibody and at least one HCP is not subjected to protein A capture (e.g., is not applied to protein A column) prior to applying the mixture to the first ion exchange resin.

Preferably, the plurality of wash steps comprises at least a first wash and a second wash, wherein there is an increase in conductivity from the first wash to the second wash. More preferably, the first wash is with equilibration buffer and the second wash is with a mixture of elution buffer and water (e.g., WFI). For example, the mixture of elution buffer and water can comprise about 40-50% elution buffer and about 50-60% water. More preferably, the mixture of elution buffer and water can comprise about 45% elution buffer and about 55% water. In a preferred embodiment, the elution buffer comprises 20 mM sodium phosphate and 150 mM sodium chloride. In this situation, a mixture of elution buffer and water that is 45% elution buffer and about 55% water is 9 mM sodium phosphate and 68 mM sodium chloride. In a preferred embodiment, the first wash is with an equilibrium buffer comprising 20 mM phosphate, 25 mM sodium chloride, the second wash is with a buffer comprising 9 mM phosphate, 68 mM sodium chloride (45% elution buffer, 55% water) and the elution buffer comprises 20 mM sodium phosphate and 150 mM sodium chloride.

In one embodiment, the method using the first ion exchange resin is carried out at pH 7. In another embodiment, the method using the first ion exchange resin is carried out at pH 5. In yet another embodiment, the method using the first ion exchange resin is carried out at a pH in a range of about pH 5 to about pH 7, or a range of pH 5 to pH 7. When pH 7 is used, preferably about 35 grams of antibody per liter of resin is applied. When pH 5 is used, preferably about 70 grams of antibody per liter of resin is applied. When a pH in the range of about pH 5 to about pH 7 (e.g., pH 5 to pH 7) is used, preferably an amount of antibody from about 35 to about 70 grams of antibody per liter of resin (e.g., 35-70 grams of antibody per liter of resin) is applied.

In a preferred embodiment, better HCP clearance from the antibody-HCP mixture is achieved (e.g., at pH 5) by loading more antibody onto the resin (e.g., about 70 grams of antibody per liter of resin) than is achieved when less antibody (e.g., about 30 grams of antibody per liter of resin) is loaded onto the resin. This is thought to be the result of displacement of HCP from the resin by the antibody when conditions are used at which the binding affinity of the antibody for the resin is significantly greater than that of HCP for the resin.

Preferably, the first ion exchange resin is a cation exchange resin. Preferably, the cation exchange resin is formed into a column and the mixture comprising the antibody and at least one HCP is applied to the column. Preferably, the cation exchange resin comprises a synthetic methacrylate based polymeric resin attached to a sulfonate group (e.g., Fractogel S). Alternatively, the cation exchange resin can comprise, for example, methacrylate or polystyrene based synthetic polymers, silica, highly cross-linked agarose with dextran surface extender, cross-linked copolymer of allyl dextran and N. N. methylene bisacryla resins attached to a sulfonate group, such as sulfonium ions or sulfoethyl.

In another aspect of the invention, after the method using the first ion exchange resin described above is carried out, the method further comprises subjecting the first eluate to a viral inactivation step. For example, wherein viral inactivation can be achieved by pH viral inactivation to form a virally-inactived preparation (e.g., the first eluate is subjected to low pH conditions, such as pH of about 3.5, to thereby inactivate viruses). Preferably, the virally-inactivated preparation is applied to a second ion exchange resin, wherein, prior to applying the virally-inactivated preparation to the second ion exchange resin, pH and conductivity of the virally-inactivated preparation is adjusted to be substantially similar to pH and conductivity of the second ion exchange resin. For example, the pH of the second ion exchange resin can be in a range of about pH 7.7 to about pH 8.3 and the pH of the virally-inactivated preparation is adjusted to be in a range of about pH 7.7 to about pH 8.3. In another embodiment, the pH of the second ion exchange resin can be in a range of about pH 7.8 to about pH 8.2 and the pH of the virally-inactivated preparation is adjusted to be in a range of about pH 7.8 to about pH 8.2. More preferably, the pH of the second ion exchange resin is about pH 8.0 and the pH of the virally-inactivated preparation is adjusted to be about pH 8.0. Furthermore, the conductivity of the second ion exchange resin can be in a range of about 3.5 mS/cm to about 5.2 mS/cm and the conductivity of the virally-inactivated preparation is adjusted to be in a range of about 3.5 mS/cm to about 5.2 mS/cm. Preferably, the conductivity of the second ion exchange resin is about 5.0 mS/cm and the conductivity of the virally-inactivated preparation is adjusted to be about 5.0 mS/cm.

In a preferred embodiment, the second ion exchange resin is an anion exchange resin. For example, the anion exchange resin can be a Q sepharose resin. Preferably, the second ion exchange resin is formed into a column and the virally-inactivated preparation is applied to the column such that a first flow through is obtained.

In another aspect of the invention, after the first through is obtained from the second ion exchange resin, the first flow through can be applied to a hydrophobic interaction column such that a second eluate is obtained. In a preferred embodiment, the hydrophobic interaction column is a phenyl sepharose column. In one embodiment, the first flow through applied to the hydrophobic interaction column comprises about 20 to about 40 grams of antibody per liter of hydrophobic interaction column material. In another embodiment, the first flow through applied to the hydrophobic interaction column comprises about 30 to about 36 grams of antibody per liter of hydrophobic interaction column material. Due to the efficiency of the prior steps in the purification process, it has been found that it is not necessary to subject the second eluate, obtained from the hydrophobic interaction column, to product peak fractionation. Thus, in one embodiment, the second eluate is not subjected to product peak fractionation.

In a particularly preferred embodiment, the method of the invention for producing a host cell protein-(HCP) reduced antibody preparation from a mixture comprising an antibody and at least one HCP comprises:

(a) applying the mixture to a cation exchange resin in an equilibration buffer, wherein the mixture has not been subjected to protein A capture prior to applying to the cation exchange resin and wherein greater than 30 grams of antibody per liter of resin are applied;

(b) washing HCP from the cation exchange resin with a plurality of wash steps;

(c) eluting the antibody from the cation exchange resin with an elution buffer to form a first eluate;

(d) subjecting the first eluate to a viral inactivation step;

(e) applying the virally-inactivated preparation to an anion exchange resin to obtain a first flow through; and (f) applying the first flow through to a hydrophobic interaction column such that a second eluate is obtained;

such that the HCP-reduced antibody preparation is obtained.

In one embodiment, the cation exchange resin is at pH 7 and about 35 grams of antibody per liter of resin are applied. In another embodiment, the cation exchange resin is at pH 5 and about 70 grams of antibody per liter of resin are applied. In yet another embodiment, the pH is in a range of about pH 5 to about pH 7 (e.g., pH 5 to pH 7) and an amount of antibody from about 35 to about 70 grams of antibody per liter of resin (e.g., 35-70 grams of antibody per liter of resin) is applied.

Preferably, the plurality of wash steps comprises washing the resin with a first wash using the equilibration buffer and a second wash using a mixture of the elution buffer and water. For example, the mixture of elution buffer and water can comprise about 40-50% elution buffer and about 50-60% water (e.g., WFI), more prefably about 45% elution buffer and about 55% water (e.g., WFI). In a preferred embodiment, the elution buffer comprises 20 mM sodium phosphate and 150 mM sodium chloride. In this situation, a mixture of elution buffer and water that is 45% elution buffer and about 55% water is 9 mM sodium phosphate and 68 mM sodium chloride. In a preferred embodiment, the first wash is with an equilibrium buffer comprising 20 mM phosphate, 25 mM sodium chloride, the second wash is with a buffer comprising 9 mM phosphate, 68 mM sodium chloride (45% elution buffer, 55% water) and the elution buffer comprises 20 mM sodium phosphate and 150 mM sodium chloride.

Preferably, in the above-described method with steps (a) through (f), prior to applying the virally-inactivated preparation to the anion ion exchange resin (i.e., between steps (d) and (e)), pH and conductivity of the virally-inactivated preparation is adjusted to be substantially similar to pH and conductivity of the anion exchange resin. For example, the pH of the second ion exchange resin can be in a range of about pH 7.7 to about pH 8.3 and the pH of the virally-inactivated preparation is adjusted to be in a range of about pH 7.7 to about pH 8.3. In another embodiment, the pH of the second ion exchange resin can be in a range of about pH 7.8 to about pH 8.2 and the pH of the virally-inactivated preparation is adjusted to be in a range of about pH 7.8 to about pH 8.2. More preferably, the pH of the second ion exchange resin is about pH 8.0 and the pH of the virally-inactivated preparation is adjusted to be about pH 8.0. Furthermore, the conductivity of the second ion exchange resin can be in a range of about 3.5 mS/cm to about 5.2 mS/cm and the conductivity of the virally-inactivated preparation is adjusted to be in a range of about 3.5 mS/cm to about 5.2 mS/cm. Preferably, the conductivity of the second ion exchange resin is about 5.0 mS/cm and the conductivity of the virally-inactivated preparation is adjusted to be about 5.0 mS/cm.

In the above-described method with steps (a) through (f), preferably the cation exchange resin is a synthetic methacrylate-based polymeric resin attached to a sulfonate group (e.g., Fractogel), the anion exchange resin is a Q sepharose resin and the hydrophobic interaction column is a phenyl sepharose column.

Preferably, the first eluate comprises a range of about 90 to about 100 fold less HCP than the mixture as determined by a HCP ELISA. Preferably, the first flowthrough comprises a range of about 840 to about 850 fold less HCP than the first eluate as determined by a HCP ELISA. Preferably, the second eluate comprises a range of about 3 to about 5 fold less HCP than the first flowthrough as determined by a HCP ELISA.

In a particularly preferred embodiment, the method of the invention for producing a host cell protein-(HCP) reduced antibody preparation from a mixture comprising an antibody and at least one HCP comprises:

(a) applying the mixture to a cation exchange resin in an equilibration buffer, wherein the cation exchange resin is at pH 7 and about 35 grams of antibody per liter of resin are applied, or the cation exchange resin is at a pH in a range of pH 5 to pH 7 and about 35 to about 70 grams of antibody per liter of resin are applied, or the cation exchange resin is at pH 5 and about 70 grams of antibody per liter of resin are applied;

(b) washing HCP from the cation exchange resin with wash steps comprising a first wash using the equilibration buffer and a second wash using a mixture of an elution buffer and water;

(c) eluting the antibody from the cation exchange resin with the elution buffer to form a first eluate;

(d) subjecting the first eluate to a viral inactivation step, wherein viral inactivation is achieved by pH viral inactivation to form a virally-inactived preparation;

(e) applying the virally-inactivated preparation to an anion exchange resin, wherein, prior to applying the virally-inactivated preparation to the anion ion exchange resin, pH and conductivity of the virally-inactivated preparation is adjusted to be substantially similar to pH and conductivity of the anion exchange resin, such that a first flow through is obtained; and (f) applying the first flow through to a hydrophobic interaction column such that a second eluate is obtained;
such that the HCP-reduced antibody preparation is obtained.

Preferably, the antibody mixture has not been subjected to protein A capture prior to applying to the cation exchange resin. Preferably, the mixture of elution buffer and water comprises about 40-50% elution buffer and about 50-60% water, more prefably about 45% elution buffer and about 55% water (e.g., WFI). In a preferred embodiment, the elution buffer comprises 20 mM sodium phosphate and 150 mM sodium chloride. In this situation, a mixture of elution buffer and water that is 45% elution buffer and about 55% water is 9 mM sodium phosphate and 68 mM sodium chloride. In a preferred embodiment, the first wash is with an equilibrium buffer comprising 20 mM phosphate, 25 mM sodium chloride, the second wash is with a buffer comprising 9 mM phosphate, 68 mM sodium chloride (45% elution buffer, 55% water) and the elution buffer comprises 20 mM sodium phosphate and 150 mM sodium chloride. Preferably, the first eluate comprises a range of about 90 to about 100 fold less HCP than the mixture as determined by a HCP ELISA. Preferably, the first flowthrough comprises a range of about 840 to about 850 fold less HCP than the first eluate as determined by a HCP ELISA. Preferably, the second eluate comprises a range of about 3 to about 5 fold less HCP than the first flowthrough as determined by a HCP ELISA.

In a preferred aspect of any of the above-described purification methods, the HCP comprises procathepsin L such that a procathepsin L-reduced antibody preparation is obtained. Preferably, the eluate comprises cathepsin L activity ranging from between about 25 to about 60 RFU/s/mg of antibody as measured by a cathepsin L kinetic assay. Preferably, the first flowthrough comprises cathepsin L activity ranging from between about 0.4 to about 4 RFU/s/mg of antibody as measured by a cathepsin L kinetic assay. Preferably, the second eluate comprises cathepsin L activity ranging from between about 0.5 to about 1.5 RFU/s/mg of antibody as measured by a cathepsin L kinetic assay Preferably, the level of procathepsin L is reproducibly low.

In yet another aspect, the invention pertains to a method for producing a host cell protein-(HCP) reduced antibody preparation from a mixture comprising an antibody and at least one HCP, the method comprising:

(a) applying the mixture to a cation exchange resin to obtain a first eluate;

(b) applying the first eluate to an anion ion exchange resin to obtain a first flow through; and (c) applying the first flow through to a hydrophobic interaction column such that a second eluate is obtained;
such that the HCP-reduced antibody preparation is obtained.

Preferably, the mixture comprising an antibody and at least one HCP is not subjected to protein A capture prior to applying the mixture to the first ion exchange resin. Preferably, the method further comprises subjecting the first eluate to a viral inactivation step prior to applying the first eluate to the anion exchange resin. For example, viral inactivation can be achieved by pH viral inactivation.

Preferably, the cation exchange resin comprises a synthetic methacrylate based polymeric resin attached to a sulfonate group (e.g., the the cation exchange resin can be a Fractogel S column). For example, a Fractogel S column can be equilibrated with an equilibration buffer comprising 20 mM sodium phosphate, 25 mM sodium chloride, the mixture can be applied to the column, the column can be at least washed once with equilibration buffer and the first eluate can be obtained by eluting with an elution buffer comprising 20 mM sodium phosphate, 150 mM sodium chloride.

Preferably, the anion exchange resin is a Q sepharose column For example, a Q sepharose column can be equilibrated with an equilibratoin buffer comprising 25 mM trolamine, 40 mM sodium chloride, pH 7.6.

Preferably, the hydrophobic interaction column is a phenyl sepharose column. For example, a phenyl sepharose column can be equilibrated with an equilibration buffer comprising 20 mM sodium phosphate, 1.1 M $(NH_4)_2SO_4$, pH 7, the first flowthrough can be applied to the column, the column can be at least washed once with equilibration buffer and the second eluate can be obtained by performing a salt step-gradient to 11 mM sodium phosphate, 0.625 M $(NH_4)_2SO_4$, pH 7.0.

Preferably, pH viral inactivation is achieved by maintaining the first eluate at pH 3.5 for approximately one hour.

In yet another aspect, the invention pertains to a method for producing a host cell protein-(HCP) reduced adalimumab preparation from a mixture comprising adalimumab and at least one HCP, the method comprising:

(a) applying the mixture to a cation exchange resin, wherein the mixture is not subjected to protein A capture prior to applying the mixture to the first ion exchange resin, to obtain a first eluate;

(b) subjecting the first eluate to pH viral inactivation to obtain a virally inactivated preparation;

(c) applying the virally inactivated preparation to an anion ion exchange resin to obtain a first flow through; and (c) applying the first flow through to a hydrophobic interaction column such that a second eluate is obtained;

such that the HCP-reduced adalimumab preparation is obtained.

Preferably, the cation exchange resin is a Fractogel S column, the anion exchange resin is a Q sepharose column and the hydrophobic interaction column is a phenyl sepharose column. For example, a Fractogel S column can be equilibrated with an equilibration buffer comprising 20 mM sodium phosphate, 25 mM sodium chloride, the mixture can be applied to the column, the column can be at least washed once with equilibration buffer and the first eluate can be obtained by eluting with an elution buffer comprising 20 mM sodium phosphate, 150 mM sodium chloride. Also for example, a Q sepharose column can be equilibrated with an equilibration buffer comprising 25 mM trolamine, 40 mM sodium chloride, pH 7.6. Also for example, a phenyl sepharose column can be equilibrated with an equilibration buffer comprising 20 mM sodium phosphate, 1.1 M $(NH_4)_2SO_4$, pH 7, the first flowthrough can be applied to the column, the column can be at least washed once with equilibration buffer and the second eluate can be obtained by performing a salt step-gradient to 11 mM sodium phosphate, 0.625 M $(NH_4)_2SO_4$, pH 7.0. Also for example, pH viral inactivation can be achieved by maintaining the first eluate at pH 3.5 for approximately one hour.

With respect to all of the above-described purification methods, in a preferred embodiment of the invention, the antibody is an anti-tumor necrosis factor-alpha (TNFα) antibody, or antigen-binding portion thereof. In one embodiment, the anti-TNFα antibody, or antigen-binding portion thereof, is a chimeric antibody, a humanized antibody or a multivalent antibody. In one embodiment, the anti-TNFα antibody, or antigen-binding portion thereof, is infliximab or golimumab.

In another embodiment, the anti-TNFα antibody, or antigen-binding portion thereof, is a human antibody. In one embodiment, the anti-TNFα antibody, or antigen-binding portion thereof, is an isolated human antibody that dissociates from human TNFα with a $K_d$ of $1\times10^{-8}$ M or less and a $K_{off}$ rate constant of $1\times10^{-3}$ $s^{-1}$ or less, both determined by surface plasmon resonance, and neutralizes human TNFα cytotoxicity in a standard in vitro L929 assay with an $IC_{50}$ of $1\times10^{-7}$ M or less.

In another embodiment, the anti-TNFα antibody, or antigen-binding portion thereof, is an isolated human antibody with the following characteristics:

a) dissociates from human TNFα with a $K_{off}$ rate constant of $1\times10^{-3}$ $s^{-1}$ or less, as determined by surface plasmon resonance;

b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9;

c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12.

In still another embodiment, the anti-TNFα antibody, or antigen-binding portion thereof, is an isolated human antibody with a light chain variable region (LCVR) comprising the amino acid sequence of SEQ ID NO: 1 and a heavy chain variable region (HCVR) comprising the amino acid sequence of SEQ ID NO: 2

In yet another embodiment, the anti-TNFα antibody, or antigen-binding portion thereof, is adalimumab.

The invention provides an antibody preparation which is substantially free of HCP as measured by a HCP ELISA produced using any of the methods of the invention. The invention also provides a pharmaceutical composition comprising an HCP-reduced antibody preparation produced using any of the methods of of the invention, and a pharmaceutically acceptable carrier.

The invention includes a pharmaceutical composition comprising an antibody an HCP-reduced antibody, wherein the level of HCP comprises no greater than about 70 ng of HCP per mg of antibody as measured by a HCP ELISA, and a pharmaceutically acceptable carrier. In one embodiment, the level of HCP comprises no greater than about 13 ng of HCP per mg of antibody as measured by a HCP ELISA. In another embodiment, the level of HCP comprises no greater than about 5 ng of HCP per mg of antibody as measured by a HCP ELISA.

The invention provides a composition comprising an antibody, wherein said composition has no detectable level of HCP as determined by a HCP ELISA assay.

The invention also provides an antibody preparation which is substantially free of procathepsin L produced using any of the methods described herein. The invention also includes a pharmaceutical composition comprising a procathepsin L-reduced antibody preparation produced using any of the methods described herein, and a pharmaceutically acceptable carrier.

The invention provides a pharmaceutical composition comprising an antibody a procathepsin L-reduced antibody and a pharmaceutically acceptable carrier, wherein the level of procathepsin L is no greater than a cathepsin activity of about 3.0 RFU/s/mg of antibody.

With respect to all of the above-described antibody preparations and pharmaceutical compositions, preferably the antibody is an anti-tumor necrosis factor-alpha (TNFα) antibody, or antigen-binding portion thereof. In one embodiment, the anti-TNFα antibody, or antigen-binding portion thereof, is an antibody selected from the group consisting of humanized, chimeric or multivalent. In one embodiment, the anti-TNFα antibody, or antigen-binding portion thereof, is infliximab or golimumab.

In another embodiment, the anti-TNFα antibody, or antigen-binding portion thereof, is a human antibody. In one embodiment, the anti-TNFα antibody, or antigen-binding portion thereof, is an isolated human antibody that dissociates from human TNFα with a $K_d$ of $1\times10^{-8}$ M or less and a $K_{off}$ rate constant of $1\times10^{-3}$ s$^{-1}$ or less, both determined by surface plasmon resonance, and neutralizes human TNFα cytotoxicity in a standard in vitro L929 assay with an IC$_{50}$ of $1\times10^{-7}$ M or less.

In another embodiment, the anti-TNFα antibody, or antigen-binding portion thereof, is an isolated human antibody with the following characteristics:

a) dissociates from human TNFα with a $K_{off}$ rate constant of $1\times10^{-3}$ s$^{-1}$ or less, as determined by surface plasmon resonance;

b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9;

c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12.

In still another embodiment, the anti-TNFα antibody, or antigen-binding portion thereof, is an isolated human antibody with a light chain variable region (LCVR) comprising the amino acid sequence of SEQ ID NO: 1 and a heavy chain variable region (HCVR) comprising the amino acid sequence of SEQ ID NO: 2

In yet another embodiment, the anti-TNFα antibody, or antigen-binding portion thereof, is adalimumab.

The invention includes a method of treating a disorder in which TNFα activity is detrimental comprising administering to a human subject a pharmaceutical compositions comprising an antibody obtained using any of the methods of the invention. In one embodiment, the preparation is administering to the human subject over a prolonged period of time. In one embodiment, the prolonged period of time includes at least about 3 months, at least about 4 months or at least about 5 months.

In one embodiment, the disorder in which TNFa activity is detrimental is selected from the group consisting of an autoimmune disorder, an intestinal disorder, and a skin disease. In one embodiment, the autoimmune disorder is selected from the group consisting of rheumatoid arthritis, rheumatoid spondylitis, osteoarthritis, gouty arthritis, an allergy, multiple sclerosis, psoriatic arthritis, autoimmune diabetes, autoimmune uveitis, nephrotic syndrome, and juvenile rheumatoid arthritis. In another embodiment,the intestinal disorder is Crohn's disease. In still another embodiment, the skin disease is psoriasis.

In one embodiment, the pharmaceutical composition is administering in combination with an additional therapeutic agent. In one embodiment, the additional therapeutic agent is methotrexate.

The invention includes a method of treating a disorder in which TNFα activity is detrimental comprising administering to a human subject the pharmaceutical composition comprising an antibody obtained using any of the methods of the invention. In one embodiment, the preparation is administering to a human subject over a prolonged period of time. In one embodiment, the prolonged period of time includes at least about 3 months, at least about 4 months or at least about 5 months. In one embodiment, the disorder in which TNFα activity is detrimental is selected from the group consisting of an autoimmune disorder, an intestinal disorder, and a skin disease. In one embodiment, the autoimmune disorder is selected from the group consisting of rheumatoid arthritis, rheumatoid spondylitis, osteoarthritis, gouty arthritis, an allergy, multiple sclerosis, psoriatic arthritis, autoimmune diabetes, autoimmune uveitis, nephrotic syndrome and juvenile rheumatoid arthritis. In one embodiment, the intestinal disorder is Crohn's disease. In one embodiment, the skin disease is psoriasis.

In one embodiment, the pharmaceutical composition is administered in combination with an additional therapeutic agent. In one embodiment, the additional therapeutic agent is methotrexate.

The invention provides an article of manufacture comprising a packaging material, adalimumab, and a label or package insert contained within the packaging material indicating that the adalimumab formulation comprises no greater than about 70 ng of HCP per mg of adalimumab. In one embodiment, the about 70 ng of HCP per mg of adalimumab is measured by a HCP ELISA.

The invention also provides an article of manufacture comprising a packaging material, adalimumab, and a label or package insert contained within the packaging material indicating that the adalimumab formulation comprises no greater than about 13 ng of HCP per mg of adalimumab. In one embodiment, the about 13 ng of HCP per mg of adalimumab is measured by a HCP ELISA.

The invention includes an article of manufacture comprising a packaging material, adalimumab, and a label or package insert contained within the packaging material indicating that the adalimumab formulation comprises no greater than about 5 ng of HCP per mg of adalimumab. In one embodiment, the about 5 ng of HCP per mg of adalimumab is measured by a HCP ELISA.

The invention includes an article of manufacture comprising a packaging material, adalimumab, and a label or package insert contained within the packaging material indicating that the adalimumab formulation comprises no greater a level of procathepsin L than that indicated by a cathepsin L activity of about 3.0 RFU/s/mg adalimumab. In one embodiment, cathepsin L activity is measured by a cathepsin L kinetic assay.

The invention further provides a kinetic assay for determining the amount of procathepsin L in a material derived from a mammalian cell expression system comprising contacting the material derived from a mammalian cell expression system with an enzyme to process procathepsin L to an active cathepsin L form, such that a cathepsin L sample is obtained; contacting the cathepsin L sample with a substrate for cathepsin L; and determining the cathepsin L activity in the cathepsin L sample as an indication of the amount procathepsin L in the material derived from the mammalian cell expression system. In one embodiment, the mammalian cell expression system is Chinese Hamster Ovary (CHO) cells. In another embodiment, the enzyme to process procathepsin L is an endopeptidase. In still another embodiment, the substrate for cathepsin L comprises a label. In still another embodiment, the label is a fluorescent agent. In one embodiment, the fluorescent agent comprises a fluorescent 7-amino-4-methyl coumarin (AMC) group. In one embodiment, the substrate for cathepsin L comprises Z-leucine-arginine. In still another embodiment, the Z-leucine-arginine comprises an AMC group.

DETAILED DESCRIPTION OF THE INVENTION

I. Definitions

Figure 1A:
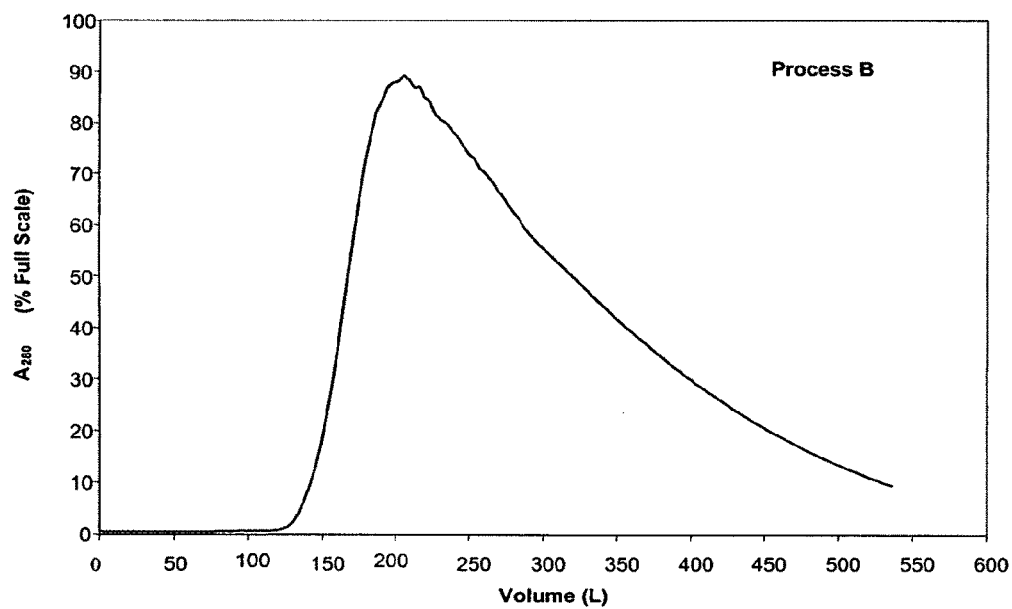
FIGS. 1A and 1B show the typical elution profiles for the Fractogel S chromatography step for each process, including the process of the invention (FIG. 1A) and process A (FIG. 1B).

In order that the present invention may be more readily understood, certain terms are first defined.

The term "mixture", as used herein, refers to a material having viscosity which is to be purified comprising at least one antibody of interest which is sought to be purified from other substances which may also be present. Mixtures can, for example, be aqueous solutions, organic solvent systems, or aqueous/organic solvent mixtures or solutions. The mixtures are often complex mixtures or solutions comprising many biological molecules (such as proteins, antibodies, hormones, and viruses), small molecules (such as salts, sugars, lipids, etc.) and even particulate matter. While a typical mixture of biological origin may begin as an aqueous solution or suspension, it may also contain organic solvents used in earlier separation steps such as solvent precipitations, extractions, and the like. Examples of mixtures that may contain valuable biological substances amenable to the purification by various embodiments the present invention include, but are not limited to, a culture supernatant from a bioreactor, a homogenized cell suspension, plasma, plasma fractions, and milk.

By "purifying" an antibody from a mixture comprising the antibody and one or more substances is meant increasing the degree of purity of the antibody in the mixture by removing (completely or partially) at least one substance from the composition. The substance may be an impurity or contaminant, such as, but not limited to, a host cell protein (HCP).

The term "host cell protein(s)" or "HCP(s)" refers to proteins in the mixture that are different from the antibody of interest and typically originate from the source of the antibody production. HCPs are desirably excluded from the final antibody preparation.

The term "reduced" refers to the lessening or diminishing the amount of a substance. A reduced preparation includes a preparation which has less of a substance, such as HCPs or procathepsin L, relative to an initial amount. In one embodiment, the substance is an impurity or contaminant. In one embodiment, the term "reduced" means substantially less of the substance. In another embodiment, the term "reduced" means no amount of the substance. In one embodiment, no amount of a substance includes "no detectable amount" using assays described herein.

The term "substantially free" includes no amount of a substance, but can also include a minimal amount of a substance. In one embodiment, no amount of a substance includes "no detectable amount" using assays described herein.

The term "host cell protein- (HCP-) reduced" refers to a composition, including, but not limited to, an eluate, an preparation, a flowthrough, comprising an antibody and a lessened or diminished amount of HCP(s) following one or more purification steps. In one embodiment, the term "HCP-reduced" means substantially less of the HCP(s) in the composition comprising an antibody. In another embodiment, the term "HCP-reduced" means no amount of the HCP(s) in the composition comprising an antibody. In one embodiment, the term "HCP-reduced" means no detectable amount using assays described herein in the composition comprising an antibody.

The term "procathepsin L-reduced" refers to a composition, including, but not limited to, an eluate, an preparation, a flowthrough, comprising an antibody and a lessened or diminished amount of procathepsin L following one or more purification steps. In one embodiment, the term "procathepsin L-reduced" means substantially less of the HCP(s) in the composition comprising an antibody. In another embodiment, the term "procathepsin L-reduced" means no amount of the HCP(s) in the composition comprising an antibody. In one embodiment, the term "procathepsin L-reduced" means no detectable amount using assays described herein in the composition comprising an antibody.

The term "reproducibly low" refers to an ability to consistently achieve a lessened or diminished amount, such as an ability to achieve a lessened or diminished amount at least 80% of the time, more preferably at least 90% of the time, more preferably at least 95% of the time and even more preferably at least 98% of the time.

The term "ion exchange separation step" refers to a step where undesired substances or impurities, e.g., HCPs or procathepsin L, are set apart from an antibody of interest based on differences in the ionic interactions of the antibody of interest and the undesired substance with a charged material. An example of an ion exchange separation step includes, but is not limited to, ion exchange chromatography, including anion exchange chromatography and cation exchange chromatography.

"Ion exchange material" refers to an ionic material which is used as the basis for the separation of the undesired substances or impurities, e.g., HCPs or procathepsin L, from the antibody. Examples of ion exchange materials include anionic and cationic resins.

"Cation exchange material" refers to an ion exchange resin with covalently bound negatively charged ligands, and which thus has free cations for exchange with cations in a solution with which the resin is contacted. A wide variety of cation exchange resins are known in the art, for example, those wherein the covalently bound groups are carboxylate or sulfonate. Commercially available cation exchange resins include CMC-cellulose, SP-Sephadex™, and Fast S-Sepharose™ (the latter two being commercially available from Pharmacia).

"Anion exchange material" refers to an ion exchange resin with covalently bound positively charged groups, such as quaternary amino groups. Commercially available anion exchange resins include DEAE cellulose, TMAE, QAE Sephadex™, and Fast Q Sepharose™ (the latter two being commercially available from Pharmacia).

By "binding" a molecule to an ion exchange material is meant exposing the molecule to the ion exchange material under appropriate conditions (pH/conductivity) such that the molecule is reversibly immobilized in or on the ion exchange material by virtue of ionic interactions between the molecule and a charged group or charged groups of the ion exchange material.

The term "hydrophobic interaction step" refers to a step where undesired substances, e.g., HCPs or procathepsin L, are set apart from an antibody of interest based on the differences in the hydrophobic interactions of the antibody of interest and the undesired substance with a hydrophobic material.

The term "hydrophobic interaction material" refers to a hydrophobic material which is used as the basis for the separation of the undesired substances, e.g., HCPs or procathepsin L, and the antibody. Examples of hydrophobic interaction materials include hydrophobic ligands such as alkyl groups having from about 2 to about 8 carbon atoms, or aryl groups such as phenyl.

The term "washing" or "wash step" includes passing an appropriate buffer through or over a given material, e.g., ion exchange material or hydrophobic interaction material.

The term "plurality of wash steps" includes more than one successive wash steps The successive buffers may have varying properties such as pH, conductivity, solvent concentration, etc., designed to dissociate and remove varying types of impurities that are non-specifically associated with the given material, e.g., ion exchange material or hydrophobic interaction material. In one embodiment, the plurality of wash steps includes an intermediate wash, further comprising about 40-50% elution buffer.

To "elute" a molecule (e.g. antibody or contaminant substance) from a material is meant to remove the molecule therefrom by altering the buffer surrounding the material and thereby decreasing the interaction of the molecule and the material. In one embodiment, an antibody is eluted from an ion exchange column wherein the buffer competes with the antibody for the charged sites on the ion exchange material.

The term "eluate" refers to liquid comprising the molecule, (e.g. antibody or contaminant substance) which was obtained subsequent to the binding of the antibody of interest to a chromatography material and addition of an elution buffer to dissociate the antibody. Eluates may be referred to with respect to the step in the purification process. For example, the term "first eluate" refers to the eluate from the first chromatographic step, the term "second eluate" refers to the eluate from the second chromatographic step, etc.

The term "flowthrough" refers to a liquid comprising a molecule (e.g. antibody or contaminant substance) which was obtained by passing a mixture comprising the molecule over a chromatography material such that the molecule passes over the material without binding.

A "buffer" refers to a substance which, by its presence in solution, increases the amount of acid or alkali that must be added to cause unit change in pH. A buffered solution resists changes in pH by the action of its acid-base conjugate components. Buffered solutions for use with biological reagents are generally capable of maintaining a constant concentration of hydrogen ions such that the pH of the solution is within a physiological range. Traditional buffer components include, but are not limited to, organic and inorganic salts, acids and bases. Exemplary buffers for use in purification of biological molecules (e.g., antibodies) include the zwitterionic or "Good" Buffers, see e.g., Good et al. (1966) *Biochemistry* 5:467 and Good and Izawa (1972) *Methods Enzymol.* 24:62. Exemplary buffers include but are not limited to TES, MES, PIPES, HEPES, MOPS, MOPSO, TRICINE and BICINE.

"Wash buffer" as used herein all refer herein to the substance used to carry away impurities from the given material, e.g., ion exchange material or hydrophobic interaction material, to which the antibody is bound.

The "elution buffer" refers to a substance that is used to dissociate the antibody from the given material, e.g., ion exchange material or hydrophobic interaction material, after it has been washed with one or more wash substances. The elution buffer acts to dissociate the antibody. Typical elution substances are well known in the art and may have higher concentrations of salts, free affinity ligands or analogs, or other substances that promote dissociation of the target substance, e.g., antibody from the given material. The conductivity and/or pH of the elution buffer is/are such that the antibody is eluted from the ion exchange or hydrophobic interaction material.

The term "conductivity" refers to the ability of an aqueous solution to conduct an electric current between two electrodes. In solution, the current flows by ion transport. Therefore, with an increasing amount of ions present in the aqueous solution, the solution will have a higher conductivity. The unit of measurement for conductivity is mmhos (mS/cm), and can be measured using a conductivity meter sold, e.g., by Orion. The conductivity of a solution may be altered by changing the concentration of ions therein. For example, the concentration of a buffering agent and/or concentration of a salt (e.g. NaCl or KCl) in the solution may be altered in order to achieve the desired conductivity. In one embodiment, the salt concentration of a wash buffer or any other aqueous solution used in chromatography is modified to achieve the desired conductivity.

The "pI" or "isoelectric point" of a polypeptide, such as an antibody, refers to the pH at which the polypeptide's positive charge balances its negative charge. pI can be calculated from the net charge of the amino acid residues of the polypeptide or can be determined by isoelectric focusing.

The term "viral inactivation" includes rendering a virus contained in the mixture nonfunctional or removing a virus from the mixture to be purified. The virus may originate from the source of antibody production, downstream processing steps or manufacturing conditions. Methods of rendering a virus nonfunctional or removing a virus include heat activation, pH inactivation, chemical inactivating agents, etc. The term "pH viral inactivation" includes subjecting a virus to a pH sufficient to render the virus nonfunctional.

The term "human TNFα" (abbreviated herein as hTNFα, or simply hTNF), as used herein, is intended to refer to a human cytokine that exists as a 17 kD secreted form and a 26 kD membrane associated form, the biologically active form of which is composed of a trimer of noncovalently bound 17 kD molecules. The structure of hTNFα is described further in, for example, Pennica, D., et al. (1984) *Nature* 312:724-729; Davis, J. M., et al. (1987) *Biochemistry* 26:1322-1326; and Jones, E. Y., et al. (1989) *Nature* 338:225-228. The term human TNFα is intended to include recombinant human TNFα (rhTNFα), which can be prepared by standard recombinant expression methods or purchased commercially (R & D Systems, Catalog No. 210-TA, Minneapolis, Minn.). TNFα is also referred to as TNF.

The term "antibody", as used herein, is intended to refer to immunoglobulin molecules comprised of four polypeptide chains, two heavy (H) chains and two light (L) chains interconnected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The antibodies of the invention are described in further detail in U.S. Pat. Nos. 6,090,382; 6,258,562; and 6,509,015, each of which is incorporated herein by reference in its entirety. In one embodiment, the antibody of the invention is an anti-TNFα which interfere with TNFα activity. Examples of anti-TNFα antibodies include, but are not limited to, anti-TNFα human antibodies and antibody portions described herein as well as those described in U.S. Pat. Nos. 6,090,382; 6,258,562; 6,509,015, and in U.S. patent application Ser. Nos. 09/801,185 and 10/302,356, each of which is incorporated by reference herein. In one embodiment, the TNFα inhibitor used in the invention is an anti-TNFα antibody, or a fragment thereof, including infliximab (Remicade®, Johnson and Johnson; described in U.S. Pat. No. 5,656,272, incorporated by reference herein), CDP571 (a humanized monoclonal anti-TNF-alpha IgG4 antibody), CDP 870 (a humanized monoclonal anti-TNF-alpha antibody fragment), an anti-TNF dAb (Peptech), CNTO 148 (golimumab; Medarex and Centocor), antibodies described in WO 02/12502, and adalimumab (Humira® Abbott Laboratories, a human anti-TNF mAb, described in U.S. Pat. No. 6,090,382 as D2E7). Additional TNF antibodies which may be used in the invention are described in U.S. Pat. Nos. 6,593,458; 6,498,237; 6,451,983; and 6,448,380, each of which is incorporated by reference herein. The term includes the "antibody of interest" which is the antibody which is the target of the process of the invention.

The term "antigen-binding portion" of an antibody (or simply "antibody portion"), as used herein, refers to one or more fragments of an antibody that retain the ability to specifically bind to an antigen (e.g., hTNFα). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. (1993) *Proc. Natl. Acad. Sci. USA* 90:6444-6448; Poljak et al. (1994) *Structure* 2:1121-1123). The antibody portions of the invention are described in further detail in U.S. Pat. Nos. 6,090,382, 6,258,562, 6,509,015, each of which is incorporated herein by reference in its entirety.

Binding fragments are produced by recombinant DNA techniques, or by enzymatic or chemical cleavage of intact immunoglobulins. Binding fragments include Fab, Fab', F(ab')$_2$, Fabc, Fv, single chains, and single-chain antibodies. Other than "bispecific" or "bifunctional" immunoglobulins or antibodies, an immunoglobulin or antibody is understood to have each of its binding sites identical. A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992).

A "conservative amino acid substitution", as used herein, is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

"Chimeric antibodies" refers to antibodies wherein one portion of each of the amino acid sequences of heavy and light chains is homologous to corresponding sequences in antibodies derived from a particular species or belonging to a particular class, while the remaining segment of the chains is homologous to corresponding sequences from another species. In one embodiment, the invention features a chimeric antibody or antigen-binding fragment, in which the variable regions of both light and heavy chains mimics the variable regions of antibodies derived from one species of mammals, while the constant portions are homologous to the sequences in antibodies derived from another species. In a preferred embodiment of the invention, chimeric antibodies are made by grafting CDRs from a mouse antibody onto the framework regions of a human antibody.

"Humanized antibodies" refer to antibodies which comprise at least one chain comprising variable region framework residues substantially from a human antibody chain (referred to as the acceptor immunoglobulin or antibody) and at least one complementarity determining region (CDR) substantially from a non-human-antibody (e.g., mouse). In addition to the grafting of the CDRs, humanized antibodies typically undergo further alterations in order to improve affinity and/or immmunogenicity.

The term "multivalent antibody" refers to an antibody comprising more than one antigen recognition site. For example, a "bivalent" antibody has two antigen recognition sites, whereas a "tetravalent" antibody has four antigen recognition sites. The terms "monospecific", "bispecific", "trispecific", "tetraspecific", etc. refer to the number of different antigen recognition site specificities (as opposed to the number of antigen recognition sites) present in a multivalent antibody. For example, a "monospecific" antibody's antigen recognition sites all bind the same epitope. A "bispecific" or "dual specific" antibody has at least one antigen recognition site that binds a first epitope and at least one antigen recognition site that binds a second epitope that is different from the first epitope. A "multivalent monospecific" antibody has multiple antigen recognition sites that all bind the same epitope. A "multivalent bispecific" antibody has multiple antigen recognition sites, some number of which bind a first epitope and some number of which bind a second epitope that is different from the first epitope The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) *Nucl. Acids Res.* 20:6287) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

Such chimeric, humanized, human, and dual specific antibodies can be produced by recombinant DNA techniques known in the art, for example using methods described in PCT International Application No. PCT/US86/02269; European Patent Application No. 184,187; European Patent Application No. 171,496; European Patent Application No. 173,494; PCT International Publication No. WO 86/01533; U.S. Pat. No. 4,816,567; European Patent Application No. 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Cancer Res.* 47:999-1005; Wood et al. (1985) *Nature* 314:446-449; Shaw et al. (1988) *J. Natl. Cancer Inst.* 80:1553-1559); Morrison (1985) *Science* 229:1202-1207; Oi et al. (1986) *BioTechniques* 4:214; U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060, Queen et al., *Proc. Natl. Acad. Sci. USA* 86:10029-10033 (1989), U.S. Pat. Nos. 5,530,101, 5,585,089, 5,693,761, 5,693,762, Selick et al., WO 90/07861, and Winter, U.S. Pat. No. 5,225,539.

An "isolated antibody", as used herein, is intended to refer to an antibody that is substantially free of other antibodies having different antigenic specificities (e.g., an isolated antibody that specifically binds hTNFα is substantially free of antibodies that specifically_bind antigens other than hTNFα). An isolated antibody that specifically binds hTNFα may, however, have cross-reactivity to other antigens, such as TNFα molecules from other species (discussed in further detail below). Moreover, an isolated antibody may be substantially free of other cellular material and/or chemicals.

A "neutralizing antibody", as used herein (or an "antibody that neutralized hTNFα activity"), is intended to refer to an antibody whose binding to hTNFα results in inhibition of the biological activity of hTNFα. This inhibition of the biological activity of hTNFα can be assessed by measuring one or more indicators of hTNFα biological activity, such as hTNFα-induced cytotoxicity (either in vitro or in vivo), hTNFα-induced cellular activation and hTNFα binding to hTNFα receptors. These indicators of hTNFα biological activity can be assessed by one or more of several standard in vitro or in vivo assays known in the art (see U.S. Pat. No. 6,090,382). Preferably, the ability of an antibody to neutralize hTNFα activity is assessed by inhibition of hTNFα-induced cytotoxicity of L929 cells. As an additional or alternative parameter of hTNFα activity, the ability of an antibody to inhibit hTNFα-induced expression of ELAM-1 on HUVEC, as a measure of hTNFα-induced cellular activation, can be assessed.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Example 1 of U.S. Pat. No. 6,258,562 and Jönsson et al. (1993) *Ann. Biol. Clin.* 51:19; Jönsson et al. (1991) *Biotechniques* 11:620-627; Johnsson et al. (1995) *J. Mol. Recognit.* 8:125; and Johnnson et al. (1991) *Anal. Biochem.* 198:268.

The term "$K_{off}$", as used herein, is intended to refer to the off rate constant for dissociation of an antibody from the antibody/antigen complex.

The term "$K_d$", as used herein, is intended to refer to the dissociation constant of a particular antibody-antigen interaction.

The term "$IC_{50}$" as used herein, is intended to refer to the concentration of the inhibitor required to inhibit the biological endpoint of interest, e.g., neutralize cytotoxicity activity.

The term "nucleic acid molecule", as used herein, is intended to include DNA molecules and RNA molecules. A nucleic acid molecule may be single-stranded or double-stranded, but preferably is double-stranded DNA.

The term "isolated nucleic acid molecule", as used herein in reference to nucleic acids encoding antibodies or antibody portions (e.g., VH, VL, CDR3) that bind hTNFα, is intended to refer to a nucleic acid molecule in which the nucleotide sequences encoding the antibody or antibody portion are free of other nucleotide sequences encoding antibodies or antibody portions that bind antigens other than hTNFα, which other sequences may naturally flank the nucleic acid in human genomic DNA. Thus, for example, an isolated nucleic acid of the invention encoding a VH region of an anti-hTNFα antibody contains no other sequences encoding other VH regions that bind antigens other than hTNFα.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "kit" as used herein refers to a packaged product or article of manufacture comprising components. The kit preferably comprises a box or container that holds the components of the kit. The box or container is affixed with a label or a Food and Drug Administration approved protocol. The box or container holds components of the invention which are preferably contained within plastic, polyethylene, polypropylene, ethylene, or propylene vessels. The vessels can be capped-tubes or bottles. The kit can also include instructions for administering the TNFα antibody of the invention. In one embodiment the kit of the invention includes the formulation comprising the human antibody D2E7, as described in PCT/IB03/04502 and U.S. application Ser. No. 10/222,140.

Various aspects of the invention are described in further detail herein.

II. Antibody Production

The invention herein provides methods for purifying an antibody from a mixture comprising the antibody and one or more HCPs. The initial mixture is generally one resulting from the recombinant production of the antibody. Alternatively, the initial mixture may result from production of the antibody by peptide synthesis (or other synthetic means) or the antibody may be purified from a native source of the antibody.

To express the antibodies, or antibody portions of the invention, DNAs encoding partial or full-length light and heavy chains are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). Prior to insertion of the antibody or antibody-related light or heavy chain sequences, the expression vector may already carry antibody constant region sequences. For example, one approach to converting the adalimumab or adalimumab-related VH and VL sequences to full-length antibody genes is to insert them into expression vectors already encoding heavy chain constant and light chain constant regions, respectively, such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel; *Gene Expression Technology: Methods in Enzymology* 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner et al.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399, 216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr⁻ host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss and Wood (1985) *Immunology Today* 6:12-13).

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P disclosed in DD 266,710 published Apr. 12, 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for polypeptide encoding vectors. Saccharomyces cerevisiae, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183, 070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger.*

Suitable host cells for the expression of glycosylated antibodies are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

Preferred mammalian host cells for expressing the recombinant antibodies of the invention include Chinese Hamster Ovary (CHO cells) (including dhfr− CHO cells, described in Urlaub and Chasin, (1980) *PNAS USA* 77:4216-4220, used with a DHFR selectable marker, e.g., as described in Kaufman and Sharp (1982) *Mol. Biol.* 159:601-621), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Other examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for antibody production and cultured in conventional nutrient media modified as appropriate for inducing promoters, selecting transformants, or amplifying the genes encoding the desired sequences.

The host cells used to produce an antibody may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927, 762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as gentamycin drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Host cells can also be used to produce portions of intact antibodies, such as Fab fragments or scFv molecules. It is understood that variations on the above procedure are within the scope of the present invention. For example, it may be desirable to transfect a host cell with DNA encoding either the light chain or the heavy chain (but not both) of an antibody of this invention. Recombinant DNA technology may also be used to remove some or all of the DNA encoding either or both of the light and heavy chains that is not necessary for binding to hTNFα. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than hTNFα by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are culture to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium.

Recombinant human antibodies of the invention, including adalimumab or an antigen binding portion thereof, or adalimumab-related antibodies disclosed herein can be isolated by screening of a recombinant combinatorial antibody library, preferably a scFv phage display library, prepared using human VL and VH cDNAs prepared from mRNA derived from human lymphocytes. Methodologies for preparing and screening such libraries are known in the art. In addition to commercially available kits for generating phage display libraries (e.g., the Pharmacia *Recombinant Phage Antibody System*, catalog no. 27-9400-01; and the Stratagene SurfZAP™ phage display kit, catalog no. 240612), examples of methods and reagents particularly amenable for use in generating and screening antibody display libraries can be found in, for example, Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) *Bio/Technology* 9:1370-1372; Hay et al. (1992) *Hum Antibod Hybridomas* 3:81-85; Huse et al. (1989) *Science* 246:1275-1281; McCafferty et al., *Nature* (1990) 348:552-554; Griffiths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrard et al. (1991) *Bio/Technology* 9:1373-1377; Hoogenboom et al. (1991) *Nuc Acid Res* 19:4133-4137; and Barbas et al. (1991) *PNAS* 88:7978-7982.

When using recombinant techniques, the antibody can be produced intracellularly, in the periplasmic space, or directly secreted into the medium. If the antibody is produced intracellularly, as a first step, the particulate debris, either host cells or lysed cells (e.g. resulting from homogenization), is removed, for example, by centrifugation or ultrafiltration. Where the antibody is secreted into the medium, supernatants from such expression systems are generally first concentrated using a commercially available protein concentration filter, for example, an Amicon or Millipore Pellicon ultrafiltration unit.

Prior to the process of the invention, procedures for purification of antibodies from cell debris initially depend on the site of expression of the antibody. Some antibodies can be caused to be secreted directly from the cell into the surrounding growth media; others are made intracellularly. For the latter antibodies, the first step of a purification process involves: lysis of the cell, which can be done by a variety of methods, including mechanical shear, osmotic shock, or enzymatic treatments. Such disruption releases the entire contents of the cell into the homogenate, and in addition produces subcellular fragments that are difficult to remove due to their small size. These are generally removed by differential centrifugation or by filtration. Where the antibody is secreted it not he medium, supernatants from such expression systems are generally first concentrated using a commercially available protein concentration filter, for example, an Amicon or Millipore Pellicon ultrafiltration unit. Where the antibody is secreted into the medium, the recombinant host cells can also be separated from the cell culture medium, for example, by tangential flow filtration. Antibodies can be further recovered from the culture medium using the antibody purification methods of the invention.

In one embodiment, the process of the invention includes human antibodies, or antigen-binding portions thereof, that bind to human TNFα with high affinity and a low off rate, and have a high neutralizing capacity. Preferably, the human antibodies are recombinant, neutralizing human anti-hTNFα antibodies. The most preferred recombinant, neutralizing antibody used in the method of the invention is referred to herein as adalimumab, also referred to as adalimumab, Humira®, and D2E7 (the amino acid sequence of the D2E7 VL region is shown in SEQ ID NO: 1; the amino acid sequence of the D2E7 VH region is shown in SEQ ID NO: 2). The properties of D2E7 (adalimumab; Humira®) have been described in Salfeld et al., U.S. Pat. Nos. 6,090,382, 6,258,562, and 6,509,015, which are each incorporated by reference herein. Other examples of TNFα antibodies include chimeric and humanized murine anti-hTNFα antibodies which have undergone clinical testing for treatment of rheumatoid arthritis (see e.g., Elliott et al. (1994) *Lancet* 344:1125-1127; Elliot et al. (1994) *Lancet* 344:1105-1110; Rankin et al. (1995) *Br. J. Rheumatol.* 34:334-342). In another embodiment, the TNFα antibody used in the invention is infliximab (Remicade®, Johnson and Johnson; described in U.S. Pat. No. 5,656,272, incorporated by reference herein), CDP571 (a humanized monoclonal anti-TNF-alpha IgG4 antibody), CDP 870 (a humanized monoclonal anti-TNF-alpha antibody fragment), an anti-TNF dAb (Peptech), and CNTO 148 (golimumab; Medarex and Centocor, see also WO 02/12502).

In one embodiment, the methods of the invention include adalimumab antibodies and antibody portions, adalimumab-related antibodies and antibody portions, and other human antibodies and antibody portions with equivalent properties to adalimumab, such as high affinity binding to hTNFα with low dissociation kinetics and high neutralizing capacity. In one embodiment, the invention provides treatment with an isolated human antibody, or an antigen-binding portion thereof, that dissociates from human TNFα with a $K_d$ of $1 \times 10^{-8}$ M or less and a $K_{off}$ rate constant of $1 \times 10^{-3}$ s$^{-1}$ or less, both determined by surface plasmon resonance, and neutralizes human TNFα cytotoxicity in a standard in vitro L929 assay with an IC$_{50}$ of $1 \times 10^{-7}$ M or less. More preferably, the isolated human antibody, or antigen-binding portion thereof, dissociates from human TNFα with a $K_{off}$ of $5 \times 10^{-4}$ s$^{-1}$ or less, or even more preferably, with a $K_{off}$ of $1 \times 10^{-4}$ s$^{-1}$ or less. More preferably, the isolated human antibody, or antigen-binding portion thereof, neutralizes human TNFα cytotoxicity in a standard in vitro L929 assay with an IC$_{50}$ of $1 \times 10^{-8}$ M or less, even more preferably with an IC$_{50}$ of $1 \times 10^{-9}$ M or less and still more preferably with an $IC_{50}$ of $1\times10^{-10}$ M or less. In a preferred embodiment, the antibody is an isolated human recombinant antibody, or an antigen-binding portion thereof.

It is well known in the art that antibody heavy and light chain CDR3 domains play an important role in the binding specificity/affinity of an antibody for an antigen. Accordingly, in another aspect, the invention pertains to methods of treating rheumatoid arthritis by administering human antibodies obtained using the methods of the invention, wherein the antibodies have slow dissociation kinetics for association with hTNFα and that have light and heavy chain CDR3 domains that structurally are identical to or related to those of adalimumab. Position 9 of the adalimumab VL CDR3 can be occupied by Ala or Thr without substantially affecting the $K_{off}$. Accordingly, a consensus motif for the adalimumab VL CDR3 comprises the amino acid sequence: Q-R-Y-N-R-A-P-Y-(T/A) (SEQ ID NO: 3). Additionally, position 12 of the adalimumab VH CDR3 can be occupied by Tyr or Asn, without substantially affecting the $K_{off}$. Accordingly, a consensus motif for the adalimumab VH CDR3 comprises the amino acid sequence: V-S-Y-L-S-T-A-S-S-L-D-(Y/N) (SEQ ID NO: 4). Moreover, as demonstrated in Example 2 of U.S. Pat. No. 6,090,382, the CDR3 domain of the adalimumab heavy and light chains is amenable to substitution with a single alanine residue (at position 1, 4, 5, 7 or 8 within the VL CDR3 or at position 2, 3, 4, 5, 6, 8, 9, 10 or 11 within the VH CDR3) without substantially affecting the $K_{off}$. Still further, the skilled artisan will appreciate that, given the amenability of the adalimumab VL and VH CDR3 domains to substitutions by alanine, substitution of other amino acids within the CDR3 domains may be possible while still retaining the low off rate constant of the antibody, in particular substitutions with conservative amino acids. Preferably, no more than one to five conservative amino acid substitutions are made within the adalimumab VL and/or VH CDR3 domains. More preferably, no more than one to three conservative amino acid substitutions are made within the adalimumab VL and/or VH CDR3 domains. Additionally, conservative amino acid substitutions should not be made at amino acid positions critical for binding to hTNFα. Positions 2 and 5 of the adalimumab VL CDR3 and positions 1 and 7 of the adalimumab VH CDR3 appear to be critical for interaction with hTNFα and thus, conservative amino acid substitutions preferably are not made at these positions (although an alanine substitution at position 5 of the adalimumab VL CDR3 is acceptable, as described above) (see U.S. Pat. No. 6,090,382).

Accordingly, in another embodiment, the antibody or antigen-binding portion thereof preferably contains the following characteristics:

a) dissociates from human TNFα with a $K_{off}$ rate constant of $1\times10^{-3}$ s$^{-1}$ or less, as determined by surface plasmon resonance;

b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9;

c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12.

More preferably, the antibody, or antigen-binding portion thereof, dissociates from human TNFα with a $K_{off}$ of $5\times10^{-4}$ s$^{-1}$ or less. Even more preferably, the antibody, or antigen-binding portion thereof, dissociates from human TNFα with a $K_{off}$ of $1\times10^{-4}$ s$^{-1}$ or less.

Figure 1B:
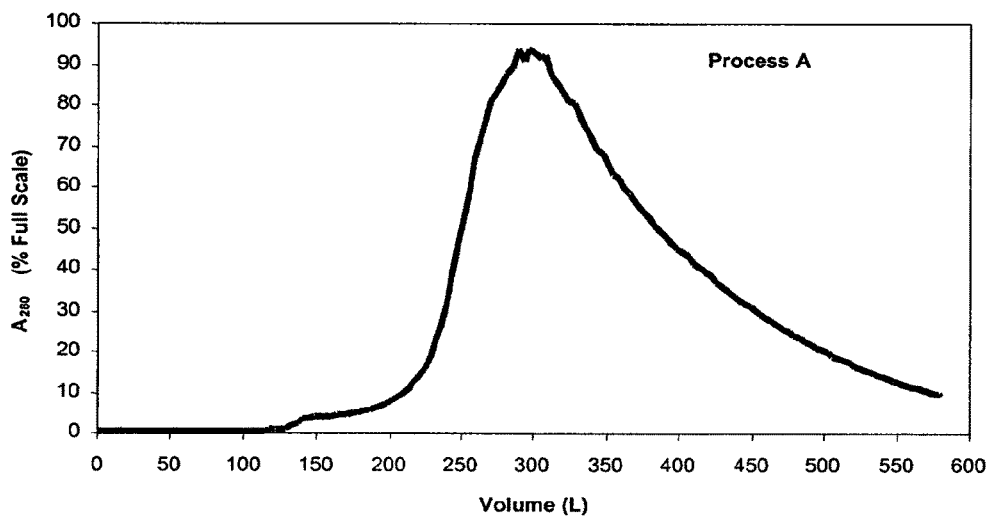
Figure 2A:
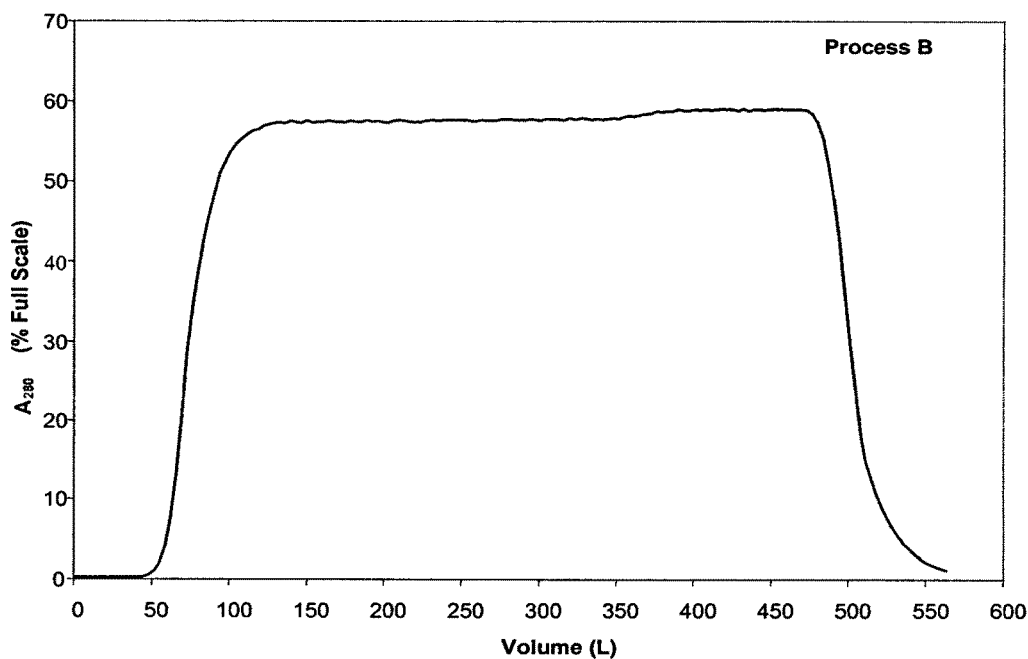
FIGS. 2A and 2B show a comparison of the flow-through wash profile of Q Sepharose FF chromatography step, including the process of the invention (FIG. 2A) and process A (FIG. 2B).
Figure 2B:
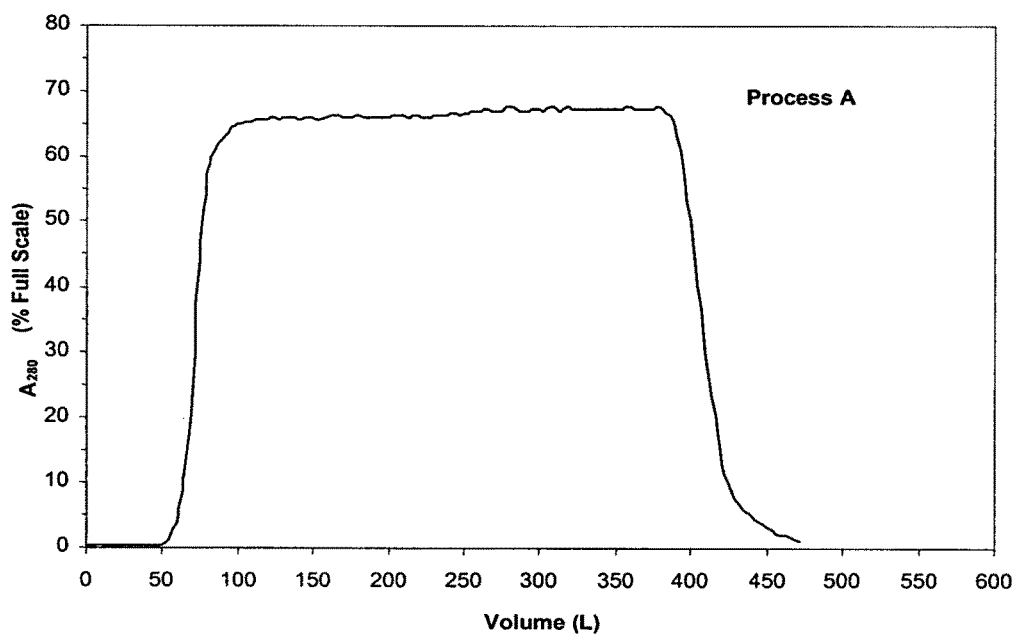

In yet another embodiment, the antibody or antigen-binding portion thereof preferably contains a light chain variable region (LCVR) having a CDR3 domain comprising the amino acid sequence of SEQ ID NO: 3, or modified from SEQ ID NO: 3 by a single alanine substitution at position 1, 4, 5, 7 or 8, and with a heavy chain variable region (HCVR) having a CDR3 domain comprising the amino acid sequence of SEQ ID NO: 4, or modified from SEQ ID NO: 4 by a single alanine substitution at position 2, 3, 4, 5, 6, 8, 9, 10 or 11. Preferably, the LCVR further has a CDR2 domain comprising the amino acid sequence of SEQ ID NO: 5 (i.e., the adalimumab VL CDR2) and the HCVR further has a CDR2 domain comprising the amino acid sequence of SEQ ID NO: 6 (i.e., the adalimumab VH CDR2). Even more preferably, the LCVR further has CDR1 domain comprising the amino acid sequence of SEQ ID NO: 7 (i.e., the adalimumab VL CDR1) and the HCVR has a CDR1 domain comprising the amino acid sequence of SEQ ID NO: 8 (i.e., the adalimumab VH CDR1). The framework regions for VL preferably are from the $V_\kappa I$ human germline family, more preferably from the A20 human germline Vk gene and most preferably from the adalimumab VL framework sequences shown in FIGS. 1A and 1B of U.S. Pat. No. 6,090,382. The framework regions for VH preferably are from the $V_H 3$ human germline family, more preferably from the DP-31 human germline VH gene and most preferably from the adalimumab VH framework sequences shown in FIGS. 2A and 2B of U.S. Pat. No. 6,090, 382.

Accordingly, in another embodiment, the antibody or antigen-binding portion thereof preferably contains a light chain variable region (LCVR) comprising the amino acid sequence of SEQ ID NO: 1 (i.e., the adalimumab VL) and a heavy chain variable region (HCVR) comprising the amino acid sequence of SEQ ID NO: 2 (i.e., the adalimumab VH). In certain embodiments, the antibody comprises a heavy chain constant region, such as an IgG1, IgG2, IgG3, IgG4, IgA, IgE, IgM or IgD constant region. Preferably, the heavy chain constant region is an IgG1 heavy chain constant region or an IgG4 heavy chain constant region. Furthermore, the antibody can comprise a light chain constant region, either a kappa light chain constant region or a lambda light chain constant region. Preferably, the antibody comprises a kappa light chain constant region. Alternatively, the antibody portion can be, for example, a Fab fragment or a single chain Fv fragment.

In still other embodiments, the antibody or antigen-binding portion thereof preferably contains adalimumab-related VL and VH CDR3 domains, for example, antibodies, or antigen-binding portions thereof, with a light chain variable region (LCVR) having a CDR3 domain comprising an amino acid sequence selected from the group consisting of SEQ ID NO: 3, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 and SEQ ID NO: 26 or with a heavy chain variable region (HCVR) having a CDR3 domain comprising an amino acid sequence selected from the group consisting of SEQ ID NO: 4, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34 and SEQ ID NO: 35.

The TNFα antibody used in the invention can be modified. In some embodiments, the TNFα antibody or antigen binding fragments thereof, is chemically modified to provide a desired effect. For example, pegylation of antibodies and antibody fragments of the invention may be carried out by any of the pegylation reactions known in the art, as described, for example, in the following references: *Focus on Growth Fac-* tors 3:4-10 (1992); EP 0 154 316; and EP 0 401 384 (each of which is incorporated by reference herein in its entirety). Preferably, the pegylation is carried out via an acylation reaction or an alkylation reaction with a reactive polyethylene glycol molecule (or an analogous reactive water-soluble polymer). A preferred water-soluble polymer for pegylation of the antibodies and antibody fragments of the invention is polyethylene glycol (PEG). As used herein, "polyethylene glycol" is meant to encompass any of the forms of PEG that have been used to derivatize other proteins, such as mono (C1—C10) alkoxy- or aryloxy-polyethylene glycol.

Methods for preparing pegylated antibodies and antibody fragments of the invention will generally comprise the steps of (a) reacting the antibody or antibody fragment with polyethylene glycol, such as a reactive ester or aldehyde derivative of PEG, under conditions whereby the antibody or antibody fragment becomes attached to one or more PEG groups, and (b) obtaining the reaction products. It will be apparent to one of ordinary skill in the art to select the optimal reaction conditions or the acylation reactions based on known parameters and the desired result.

Pegylated antibodies and antibody fragments may generally be used to treat TNFα-related disorders of the invention by administration of the TNFα antibodies and antibody fragments described herein. Generally the pegylated antibodies and antibody fragments have increased half-life, as compared to the nonpegylated antibodies and antibody fragments. The pegylated antibodies and antibody fragments may be employed alone, together, or in combination with other pharmaceutical compositions.

In yet another embodiment of the invention, TNFα antibodies or fragments thereof can be altered wherein the constant region of the antibody is modified to reduce at least one constant region-mediated biological effector function relative to an unmodified antibody. To modify an antibody of the invention such that it exhibits reduced binding to the Fc receptor, the immunoglobulin constant region segment of the antibody can be mutated at particular regions necessary for Fc receptor (FcR) interactions (see e.g., Canfield and Morrison (1991) *J. Exp. Med.* 173:1483-1491; and Lund et al. (1991) *J. of Immunol.* 147:2657-2662). Reduction in FcR binding ability of the antibody may also reduce other effector functions which rely on FcR interactions, such as opsonization and phagocytosis and antigen-dependent cellular cytotoxicity.

An antibody or antibody portion of the invention can be derivatized or linked to another functional molecule (e.g., another peptide or protein). Accordingly, the antibodies and antibody portions of the invention are intended to include derivatized and otherwise modified forms of the human anti-hTNFα antibodies described herein, including immunoadhesion molecules. For example, an antibody or antibody portion of the invention can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate associate of the antibody or antibody portion with another molecule (such as a streptavidin core region or a polyhistidine tag).

One type of derivatized antibody is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which an antibody or antibody portion of the invention may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with biotin, and detected through indirect measurement of avidin or streptavidin binding.

An antibody, or antibody portion, of the invention can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, preferably, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Sambrook, Fritsch and Maniatis (eds), *Molecular Cloning; A Laboratory Manual, Second Edition*, Cold Spring Harbor, N.Y., (1989), Ausubel et al. (eds.) *Current Protocols in Molecular Biology*, Greene Publishing Associates, (1989) and in U.S. Pat. No. 4,816,397 by Boss et al.

To express adalimumab or a adalimumab-related antibody, DNA fragments encoding the light and heavy chain variable regions are first obtained. These DNAs can be obtained by amplification and modification of germline light and heavy chain variable sequences using the polymerase chain reaction (PCR). Germline DNA sequences for human heavy and light chain variable region genes are known in the art (see e.g., the "Vbase" human germline sequence database; see also Kabat et al. (1991) *Sequences of Proteins of Immunological Interest, Fifth Edition*, U.S. Department of Health and Human Services, NIH Publication No. 91-3242; Tomlinson et al. (1992) "The Repertoire of Human Germline $V_H$ Sequences Reveals about Fifty Groups of $V_H$ Segments with Different Hypervariable Loops" *J. Mol. Biol.* 227:776-798; and Cox et al. (1994) "A Directory of Human Germ-line $V_{78}$ Segments Reveals a Strong Bias in their Usage" *Eur. J. Immunol.* 24:827-836; the contents of each of which are expressly incorporated herein by reference). To obtain a DNA fragment encoding the heavy chain variable region of adalimumab, or a adalimumab-related antibody, a member of the $V_H3$ family of human germline VH genes is amplified by standard PCR. Most preferably, the DP-31 VH germline sequence is amplified. To obtain a DNA fragment encoding the light chain variable region of adalimumab, or a adalimumab-related antibody, a member of the $V_\kappa I$ family of human germline VL genes is amplified by standard PCR. Most preferably, the A20 VL germline sequence is amplified. PCR primers suitable for use in amplifying the DP-31 germline VH and A20 germline VL sequences can be designed based on the nucleotide sequences disclosed in the references cited supra, using standard methods.

Once the germline VH and VL fragments are obtained, these sequences can be mutated to encode the adalimumab or adalimumab-related amino acid sequences disclosed herein. The amino acid sequences encoded by the germline VH and VL DNA sequences are first compared to the adalimumab or adalimumab-related VH and VL amino acid sequences to identify amino acid residues in the adalimumab or adalimumab-related sequence that differ from germline. Then, the appropriate nucleotides of the germline DNA sequences are mutated such that the mutated germline sequence encodes the adalimumab or adalimumab-related amino acid sequence, using the genetic code to determine which nucleotide changes should be made. Mutagenesis of the germline sequences is carried out by standard methods, such as PCR-mediated mutagenesis (in which the mutated nucleotides are incorporated into the PCR primers such that the PCR product contains the mutations) or site-directed mutagenesis.

Once DNA fragments encoding adalimumab or adalimumab-related VH and VL segments are obtained (by amplification and mutagenesis of germline VH and VL genes, as described above), these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat et al. (1991) *Sequences of Proteins of Immunological Interest, Fifth Edition*, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat et al. (1991) *Sequences of Proteins of Immunological Interest, Fifth Edition*, U.S. Department of Health and Human Services, NIH Publication No. 91-3242) and DNA fragments encompassing these regions can be obtained by standard PCR amplification. The light chain constant region can be a kappa or lambda constant region, but most preferably is a kappa constant region.

To create a scFv gene, the VH- and VL-encoding DNA fragments are operatively linked to another fragment encoding a flexible linker, e.g., encoding the amino acid sequence $(Gly_4\text{-}Ser)_3$, such that the VH and VL sequences can be expressed as a contiguous single-chain protein, with the VL and VH regions joined by the flexible linker (see e.g., Bird et al. (1988) *Science* 242:423-426; Huston et al. (1988) *Proc. Natl. Acad. Sci. USA* 85:5879-5883; McCafferty et al., *Nature* (1990) 348:552-554).

To express the antibodies, or antibody portions of the invention, DNAs encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). Prior to insertion of the adalimumab or adalimumab-related light or heavy chain sequences, the expression vector may already carry antibody constant region sequences. For example, one approach to converting the adalimumab or adalimumab-related VH and VL sequences to full-length antibody genes is to insert them into expression vectors already encoding heavy chain constant and light chain constant regions, respectively, such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel; *Gene Expression Technology: Methods in Enzymology* 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner et al.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr⁻ host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss and Wood (1985) *Immunology Today* 6:12-13).

Preferred mammalian host cells for expressing the recombinant antibodies of the invention include Chinese Hamster Ovary (CHO cells) (including dhfr− CHO cells, described in Urlaub and Chasin, (1980) *PNAS USA* 77:4216-4220, used with a DHFR selectable marker, e.g., as described in Kaufman and Sharp (1982) *Mol. Biol.* 159:601-621), NSO myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using protein purification methods.

Host cells can also be used to produce portions of intact antibodies, such as Fab fragments or scFv molecules. It is understood that variations on the above procedure are within the scope of the present invention. For example, it may be desirable to transfect a host cell with DNA encoding either the light chain or the heavy chain (but not both) of an antibody of this invention. Recombinant DNA technology may also be used to remove some or all of the DNA encoding either or both of the light and heavy chains that is not necessary for binding to hTNFα. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than hTNFα by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are culture to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium.

Recombinant human antibodies of the invention in addition to adalimumab or an antigen binding portion thereof, or adalimumab-related antibodies disclosed herein can be isolated by screening of a recombinant combinatorial antibody library, preferably a scFv phage display library, prepared using human VL and VH cDNAs prepared from mRNA derived from human lymphocytes. Methodologies for preparing and screening such libraries are known in the art. In addition to commercially available kits for generating phage display libraries (e.g., the Pharmacia *Recombinant Phage Antibody System*, catalog no. 27-9400-01; and the Stratagene SurfZAP™ phage display kit, catalog no. 240612), examples of methods and reagents particularly amenable for use in generating and screening antibody display libraries can be found in, for example, Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) *Bio/Technology* 9:1370-1372; Hay et al. (1992) *Hum Antibod Hybridomas* 3:81-85; Huse et al. (1989) *Science* 246:1275-1281; McCafferty et al., *Nature* (1990) 348:552-554; Griffiths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrard et al. (1991) *Bio/Technology* 9:1373-1377; Hoogenboom et al. (1991) *Nuc Acid Res* 19:4133-4137; and Barbas et al. (1991) *PNAS* 88:7978-7982.

In a preferred embodiment, to isolate human antibodies with high affinity and a low off rate constant for hTNFα, a murine anti-hTNFα antibody having high affinity and a low off rate constant for hTNFα (e.g., MAK 195, the hybridoma for which has deposit number ECACC 87 050801) is first used to select human heavy and light chain sequences having similar binding activity toward hTNFα, using the epitope imprinting methods described in Hoogenboom et al., PCT Publication No. WO 93/06213. The antibody libraries used in this method are preferably scFv libraries prepared and screened as described in McCafferty et al., PCT Publication No. WO 92/01047, McCafferty et al. *Nature* (1990) 348:552-554; and Griffiths et al. (1993) *EMBO J* 12:725-734. The scFv antibody libraries preferably are screened using recombinant human TNFα as the antigen.

Once initial human VL and VH segments are selected, "mix and match" experiments, in which different pairs of the initially selected VL and VH segments are screened for hTNFα binding, are performed to select preferred VL/VH pair combinations. Additionally, to further improve the affinity and/or lower the off rate constant for hTNFα binding, the VL and VH segments of the preferred VL/VH pair(s) can be randomly mutated, preferably within the CDR3 region of VH and/or VL, in a process analogous to the in vivo somatic mutation process responsible for affinity maturation of antibodies during a natural immune response. This in vitro affinity maturation can be accomplished by amplifying VH and VL regions using PCR primers complimentary to the VH CDR3 or VL CDR3, respectively, which primers have been "spiked" with a random mixture of the four nucleotide bases at certain positions such that the resultant PCR products encode VH and VL segments into which random mutations have been introduced into the VH and/or VL CDR3 regions. These randomly mutated VH and VL segments can be rescreened for binding to hTNFα and sequences that exhibit high affinity and a low off rate for hTNFα binding can be selected.

Following screening and isolation of an anti-hTNFα antibody of the invention from a recombinant immunoglobulin display library, nucleic acid encoding the selected antibody can be recovered from the display package (e.g., from the phage genome) and subcloned into other expression vectors by standard recombinant DNA techniques. If desired, the nucleic acid can be further manipulated to create other antibody forms of the invention (e.g., linked to nucleic acid encoding additional immunoglobulin domains, such as additional constant regions). To express a recombinant human antibody isolated by screening of a combinatorial library, the DNA encoding the antibody is cloned into a recombinant expression vector and introduced into a mammalian host cells, as described in further detail in above.

Methods of isolating human antibodies with high affinity and a low off rate constant for hTNFα are also described in U.S. Pat. Nos. 6,090,382, 6,258,562, and 6,509,015, each of which is incorporated by reference herein.

III. Antibody purification

The invention provides an method for producing an HCP-reduced antibody preparation from a mixture comprising an antibody and at least one HCP. The invention also provides a method for producing a procathepsin L-reduced antibody preparation from a mixture comprising an antibody and at least one procathepsin L. The purification process of the invention begins at the separation step when the antibody has been produced using methods described in Section II and conventional methods in the art. Typically in the art, antibody-HCP mixtures are subjected to protein A capture (e.g., a protein A column) as an initial purification step, since the antibody binds to protein A whereas HCP will flow through. The purification methods of the invention have the advantage that it is not necessary to subject the mixture comprising an antibody and at least one HCP to protein A capture (e.g., a protein A column) as an initial step, or as any step in the purification method.

Once a clarified solution or mixture comprising the antibody has been obtained, separation of the antibody from the other proteins produced by the cell, such as HCPs, is performed using a combination of different purification techniques, including ion exchange separation step(s) and hydrophobic interaction separation step(s). The separation steps separate mixtures of proteins on the basis of their charge, degree of hydrophobicity, and/or size. In one embodiment of the invention, separation is performed using chromatography, including cationic, anionic, and hydrophobic. Several different chromatography resins are available for each of these techniques, allowing accurate tailoring of the purification scheme to the particular protein involved. The essence of each of the separation methods is that proteins can be caused either to move at different rates down a long column, achieving a physical separation that increases as they pass further down the column, or to adhere selectively to the separation medium, being then differentially eluted by different solvents. In some cases, the antibody is separated from impurities when the impurities specifically adhere to the column, and the antibody does not, that is, the antibody is present in the flowthrough.

Methods of purifying antibodies from undesired proteins are provided below, e.g., process A. In one embodiment, the invention includes the steps, individually or in combination, described below in Process A. Process A provides a method of purifying a mixture comprising an antibody using ion exchange separation (cation exchange chromatography and anion exchange chromatography) and hydrophobic interaction separation, resulting in an antibody preparation suitable for use in a pharmaceutical composition. Process A has the advantage that it can be carried out without the need to perform protein A capture as an initial step in antibody purification. In one embodiment, the antibody purified using process A is adalimumab. Process A generally comprises the following:

A mixture comprising an antibody and impurities, e.g., HCP(s), is loaded onto an ion exchange column, such as a cation exchange column. The mixture may be loaded at a load of about ≦30 g antibody/L per cycle. The mixture loaded onto the cation column is subsequently washed with wash buffer (equilibration buffer). The antibody is then eluted from the column, and a first eluate is obtained.

The first eluate is then often virally inactivated and pH adjusted in preparation for anion exchange chromatography. The first eluate is virally inactivated by adjusting the pH to a low pH relative to the elution buffer (described further in section IIIC). The pH of the virally inactivated eluate is subsequently adjusted in more than one step to a final pH of about 7.6, which is the pH of the anion exchange column which follows in sequence.

Following viral inactivation, the first eluate is often subjected to a second ion exchange separation step, where the first eluate is loaded onto an anion exchange column (e.g., a Q Sepharose column). The column is washed with a wash buffer, and a first flowthrough comprising the antibody is obtained.

The flowthrough is further purified by loading it onto a hydrophobic interaction column (phenyl sepharose). The column is washed, and the antibody is eluted from the column such that a second eluate is obtained.

Process B is described below and provides an improved method for producing a host cell protein-(HCP) reduced antibody preparation from a mixture comprising an antibody. The language "reduced" when referring to HCP or procathepsin L, includes improvements over levels, e.g., concentration or activity, of HCP or procathepsin L at comparable points in process A. In one embodiment, the first eluate of process B comprises a reduced level of HCP or procathepsin L in comparison to the first eluate of process A. In one embodiment, the first flowthrough of process B comprises a reduced level of HCP or procathepsin L in comparison to the first flowthrough of process A. In one embodiment, the second eluate of process B comprises a reduced level of HCP or procathepsin L in comparison to the second eluate of process A. In another embodiment, the antibody preparation resulting from process B comprises a reduced level of HCP or procathepsin L in comparison the antibody preparation resulting from process A.

Process B generally comprises the following:

A mixture comprising an antibody and impurities, e.g., HCP(s), is loaded onto an ion exchange column, such as a cation exchange column The mixture may be loaded at a load of about ≦35 g antibody/L per cycle at pH 7 or at a load of about ≦70 g antibody/L per cycle at pH 5. The mixture loaded onto the cation column is subsequently washed with wash buffer (equilibration buffer). Following the equilibration wash buffer, an intermediate wash step is performed, wherein the column is washed with an intermediate buffer which has similar conductivity to the elution buffer. This intermediate wash step improves clearance of process-related impurities. The antibody is then eluted from the column using elution buffer, and a first eluate is obtained.

The first eluate is then virally inactivated and pH adjusted in preparation for anion exchange chromatography. The first eluate is virally inactivated by adjusting the pH to a low pH relative to the elution buffer. The pH and conductivity of the virally inactivated eluate is subsequently adjusted in one step to a final pH of about 7.8-8.2, which is the pH of the equilibrated anion exchange column which follows in sequence.

Following viral inactivation, the first eluate is subjected to a second ion exchange separation step, where the first eluate is loaded onto an anion exchange column (e.g., a Q Sepharose column). The column is washed with a wash buffer, and a first flowthrough comprising the antibody is obtained.

The flowthrough is further purified by loading it onto a hydrophobic interaction column (phenyl sepharose). The column is washed, and the antibody is eluted from the column such that a second eluate is obtained. The result of process B is a preparation having reduced HCPs, including procathepsin L. Further results of process B include the removal of process bottlenecks, e.g., higher productivity created in cell culture scale-up, by moving HCP clearance to the front part of the process and an overall improvement in antibody yield. Additional details regarding the improved process of the invention are provided below.

IIIA. Ion Exchange Separation

The present invention features methods for producing a HCP-reduced antibody preparation from a mixture comprising an antibody and at least one HCP by subjecting the mixture to at least one ion exchange separation step such that a first eluate comprising the antibody is obtained. Ion exchange separation includes any method by which two substances are separated based on the difference in their respective ionic charges.

In performing the separation, the antibody mixture may be contacted with the ion exchange material, e.g., using a batch purification technique or chromatography. For example, for batch purification, ion exchange material is prepared in or equilibrated to the desired starting buffer. A slurry of the ion exchange material is obtained. The antibody solution is contacted with the slurry to adsorb the antibody to be separated to the ion exchange material. The solution comprising the HCP(s) that do not bind to the ion exchange material is separated from the slurry, e.g., by allowing the slurry to settle and removing the supernatant. The slurry can be subjected to one or more wash steps. If desired, the slurry can be contacted with a solution of higher conductivity to desorb HCPs that have bound to the ion exchange material. In order to elute bound polypeptides, the salt concentration may be increased.

Ion exchange chromatography may also be used as an ion exchange separation technique. Ion exchange chromatography separates molecules based on differences between the overall charge of the molecules. For the purification of an antibody, the antibody must have a charge opposite to that of the functional group attached to the ion exchange material, e.g., resin, in order to bind. For example, antibodies, which generally have an overall positive charge in the buffer pH below its pI, will bind well to cation exchange material, which contain negatively charged functional groups.

In ion exchange chromatography, charged patches on the surface of the solute are attracted by opposite charges attached to a chromatography matrix, provided the ionic strength of the surrounding buffer is low. Elution is generally achieved by increasing the ionic strength (i.e., conductivity) of the buffer to compete with the solute for the charged sites of the ion exchange matrix. Changing the pH and thereby altering the charge of the solute is another way to achieve elution of the solute. The change in conductivity or pH may be gradual (gradient elution) or stepwise (step elution).

Anionic or cationic substituents may be attached to matrices in order to form anionic or cationic supports for chromatography. Anionic exchange substituents include diethylaminoethyl (DEAE), quaternary aminoethyl (QAE) and quaternary amine (Q) groups. Cationic substitutents include carboxymethyl (CM), sulfoethyl (SE), sulfopropyl (SP), phosphate (P) and sulfonate (S). Cellulose ion exchange resins such as DE23, DE32, DE52, CM-23, CM-32 and CM-52 are available from Whatman Ltd. Maidstone, Kent, U.K. SEPHADEX®-based and -locross-linked ion exchangers are also known. For example, DEAE-, QAE-, CM-, and SP-SEPHADEX® and DEAE-, Q-, CM-and S-SEPHAROSE® and SEPHAROSE® Fast Flow are all available from Pharmacia AB. Further, both DEAE and CM derivitized ethylene glycol-methacrylate copolymer such as TOYOPEARL DEAE-650S or M and TOYOPEARL CM-650S or M are available from Toso Haas Co., Philadelphia, Pa.

In one embodiment of the invention, the mixture comprising an antibody and at least one HCP is loaded onto a cation exchange (CEX) chromatography column The mixture is loaded onto the CEX column in a loading buffer which may be the same as the equilibration buffer used to equilibrate the column. As the HCP-comprising mixture passes over the CEX column, the target protein is adsorbed to the CEX resin and various HCPs (such as host cell proteins, where the target protein is produced in a recombinant host cell, or other process-derived impurities) flowthrough or bind weakly or non-specifically to the CEX resin. In various embodiments, the CEX resin is a synthetic methacrylate based polymeric resin attached to a sulfonate group (Fractogel $SO_3$__ (Fractogel S)). In one embodiment, the equilibration buffer comprises 20 mM $Na_2PO_4$, 25 mM NaCl, pH 6.8. Other suitable equilibration buffers include, for example, BIS and HEPES at physiological concentrations, for example, concentrations in the range between about 0.5 mM and about 100 mM (e.g., 10 mM, 20 mM, 50 mM, etc.), and physiological salt concentrations (e.g., about 0.15 mM NaCl), and at pH from 5.0-9.0.

In exemplary embodiments, the CEX chromatography is a Fractogel S column In one embodiment, about 30 gram (g) antibody per liter (L) resin to about 40 g antibody per L resin is loaded onto the Fractogel S column. In another embodiment, about 35 g antibody per L resin is loaded onto the Fractogel S column at pH 7. It has been discovered that a loading amount of about 35 g antibody per L resin at pH 7 increases the clearance of impurities, e.g., HCP(s) and procathepsin L. The acceptable operating ranges of a Fractogel S column to be used in the method of the invention are described in Table 1 below.

TABLE 1

Acceptable operating ranges for Fractogel S chromatography at pH 7

| Operating parameter | AOR |
| --- | --- |
| Resin capacity | ≦35 g protein/L resin |
| Load sample pH | 6.5-7.5 |
| Effective load dilution | 1:1-1:2 |
| Wash 2 elution buffer concentrate to WFI ratio | 1:3-1:4 |
| Linear velocity | 75-300 cm/hr |

It further has been discovered that the loading capacity of the column can be increased by carrying out the chromatography at pH 5. In particular, it has been discovered that a loading amount of about 70 g antibody per L resin at pH 5 increases the clearance of impurities, e.g., HCP(s) and procathepsin L. Accordingly, in a pH range of about pH 5 to about pH 7, a loading amount of about 35 g to about 70 g antibody per L of resin can be used.

Following the loading of the antibody mixture onto the column, the CEX resin is then washed with a wash buffer. In particular, it has been discovered that a plurality of wash steps with different wash buffers results in a further HCP-reduced antibody preparation. Specifically, it has been discovered that procathepsin L levels can be reduced by the use of a first wash step and an intermediate wash step using a wash buffer and an intermediate wash buffer, respectively. In one embodiment, the CEX resin is first washed with a wash buffer which is the same as the equilibration buffer. In certain embodiments, the wash buffer is 20 mM $Na_2PO_4$, 25 mM NaCl, pH 6.8. Other suitable wash buffers include, for example, BIS and HEPES at physiological concentrations, for example, concentration in the range between about 0.5 mM and about 100 mM (e.g., 10 mM, 20 mM, 50 mM, etc.), and physiological salt concentrations (e.g., about 0.15 mM NaCl), and at pH from 5.0-9.0.

In a preferred embodiment of the invention, an intermediate wash step is performed. It has been discovered that reduced levels of HCP in general, and in particular, procathepsin L, can be achieved by using an intermediate wash buffer comprising, in part, the same buffer as the CEX elution buffer. The improved reduction of HCP in general, and in particular procathepsin L, results in part, from the increased conductivity in the intermediate wash buffer. Increasing the conductivity of the intermediate wash buffer causes charge displacement of the HCP(s), which has a lower pI relative to the that of the antibody, thus causing the weaker binding HCP(s) to wash through the column. Increased clearance of the weaker binding impurities, e.g., HCP(s) including procathepsin L, in turn provides more binding area for the target substance, e.g., the antibody. In other embodiments, the intermediate wash buffer contains from about 40% to about 50% elution buffer and from about 50% to about 60% water for injection. In further embodiments, the intermediate wash buffer contains 45% elution buffer and 55% water for injection. In one embodiment, the wash buffer used in the intermediate wash is 20 mM $Na_2PO_4$, 150 mM sodium chloride, pH 7.

Following a plurality of washes, the antibody is eluted from the first cationic exchange material such that a first eluate having a reduced level of HCP is obtained. The first eluate also has a reduced level of procathepsin L in view of the intermediate wash step. In one embodiment, the first eluate obtained using the method of the invention comprises an about 3 to an about 5 fold decrease in HCP levels in comparison to a comparable step of process A. In another embodiment, the first eluate obtained using the method of the invention comprises an about 2 to an about 3 fold decrease in cathepsin L activity in comparison to a comparable step of process A. In one embodiment, the first eluate comprises a range of about 90 to about 100 fold less HCP than the mixture as determined by a HCP ELISA. In another embodiment, the first eluate comprises cathepsin L activity ranging from between about 25 to about 60 RFU/s/mg of antibody as measured by a cathepsin L kinetic assay In a preferred embodiment, the initial eluate comprising the antibody is passed over a second IE material and a flowthrough comprising a further reduced level of HCP is obtained. In some embodiments, the second IE step may be batch purification as described infra. In other embodiments, the second IE step comprises loading the first eluate onto a second ion exchange chromatography column, washing the column and obtaining a first flowthrough. The second IE material may be anion exchange (AEX) resin, e.g., Q sepharose column In some embodiments, between about 30 g antibody per L resin and about 40 g antibody per L or resin is loaded onto the anion exchange column Increasing the loading amount between about 40 g antibody per L resin and about 50 g antibody per L resin causes a decrease in clearance of impurities, e.g., HCP(s). As the HCP-comprising mixture passes over the AEX column, the various HCP(s) bind to the AEX resin, and the antibody passes through or binds nonspecifically to the AEX resin. In certain embodiments, the anion exchange resin is Q Sepharose.

Often, the antibody mixture to be purified will be present in a buffer from the previous purification step. Many buffers are available and can be selected by routine experimentation. For example, an equilibration buffer of 25 mM trolamine, 40 mM NaCl, pH 8 may be used. In one embodiment, prior to passing the initial eluate over the second IE material, the second IE material may be equilibrated with equilibration buffer. This may be done, for example, by altering the pH and conductivity of the first eluate such that the pH and conductivity of the first eluate is substantially similar or corresponds to the pH and conductivity of the equilibrated second IE material, i.e., altering the pH and conductivity of the first eluate such that it corresponds to that of the equilibrated second ion exchange material. In some embodiments, the pH of the AEX material (e.g. Q Sepharose) is adjusted with equilibration buffer to range from about 7.7 to about 8.3. In further embodiments, the pH of the CEX eluate (e.g., initial eluate) is adjusted to range about 7.7 to about 8.3. In certain embodiments, the pH of both the AEX material and the initial eluate is about 8. In some embodiments, the conductivity of the AEX material ranges from about 3.5 mS/cm to about 4.9 mS/cm. In further embodiments, the conductivity of the initial eluate ranges from about 3.5 mS/cm to about 4.9 mS/cm. It has been discovered that adjustment of the load conductivity and pH to that of the conductivity and pH of the second ion exchange material enhances impurity clearance. In relation to process A, it has been discovered that an overall decrease in conductivity and/or an increase in pH of the first eluate and/or equilibrated second ion exchange material results in increased HCP(s) clearance.

Following the loading of the antibody mixture onto the column, the AEX resin is then washed with a wash buffer. The wash buffer may be the same as the equilibration buffer, e.g., 25 mM trolamine, 40 mM NaCl, pH 8. In one embodiment, the wash may be pooled with the flowthrough such that a first flowthrough comprising the antibody and having a reduced level of HCP is obtained. In further embodiments, the first flowthrough has a reduced level of procathepsin L. In one embodiment, the first flowthrough obtained using the method of the invention comprises an about 7 to an about 700 fold decrease in HCP levels in comparison to a comparable step of process A. In another embodiment, the first flowthrough obtained using the method of the invention comprises an about 6 to an about 25 fold decrease in cathepsin L activity in comparison to a comparable step of process A. In other embodiments, the first flowthrough comprises a range of about 840 to about 850 fold less HCP than the first eluate as determined by a HCP ELISA. In yet another embodiment, the first flowthrough comprises cathepsin L activity ranging from between about 0.4 to about 4 RFU/s/mg of antibody as measured by a cathepsin L kinetic assay Acceptable operating ranges for Q sepharose chromatography to be used in the method of the invention are described below in Table 2:

TABLE 2

Acceptable operating ranges for Q Sepharose FF chromatography

| Parameter | AOR |
|---|---|
| Load conductivity | 4.0-5.5 mS/cm |
| Load pH | 7.8-8.2 |
| Column loading | ≦40 g/L |
| Linear velocity | 150-300 cm/hr |

The use of a cationic exchange material versus an anionic exchange material is based on the overall charge of the protein as discussed supra. Therefore, it is within the scope of this invention to employ an anionic exchange material prior to the use of a cationic exchange material. Furthermore, it is within the scope of this invention to employ only a cationic exchange material or only an anionic exchange material.

The methods of the present invention can optionally include further purification steps. Examples of additional purification procedures which may be performed prior to, during, or following the ion exchange chromatography method include fractionation on a hydrophobic interaction chromatography (e.g. on phenyl sepharose), ethanol precipitation, isoelectric focusing, Reverse Phase HPLC, chromatography on silica, chromatography on heparin sepharose, further anion exchange chromatography and/or further cation exchange chromatography, chromatofocusing, SDS-PAGE, ammonium sulfate precipitation, hydroxylapatite chromatography, gel electrophoresis, dialysis, and affinity chromatography (e.g. using protein A, protein G, an antibody, a specific substrate, ligand or antigen as the capture reagent).

III.B. Hydrophobic Interaction Separation

The present invention also features methods for producing a HCP-reduced antibody preparation from a mixture comprising an antibody and at least one HCP further comprising a hydrophobic interaction separation step wherein the first flowthrough is subjected to a first hydrophobic interaction material such that a second eluate having a reduced level of HCP is obtained.

In performing the separation, the polypeptide mixture may be contacted with the HIC material, e.g., using a batch purification technique or using a column. Prior to HIC purification it may be desirable to remove any chaotropic agents or very hydrophobic substances, e.g., by passing the mixture through a precolumn.

For example, for batch purification, HIC material is prepared in or equilibrated to the desired equilibration buffer. A slurry of the HIC material is obtained. The antibody solution is contacted with the slurry to adsorb the antibody to be separated to the HIC material. The solution comprising the HCPs that do not bind to the HIC material is separated from the slurry, e.g., by allowing the slurry to settle and removing the supernatant. The slurry can be subjected to one or more washing steps. If desired, the slurry can be contacted with a solution of lower conductivity to desorb antibodies that have bound to the HIC material. In order to elute bound antibodies, the salt concentration can be decreased.

In other embodiments, the hydrophobic interaction separation step comprises loading the first flowthrough onto a column comprising a first hydrophobic interaction material and washing the first hydrophobic interaction material such that a second eluate is obtained.

The hydrophobic interaction separation step may include a hydrophobic interaction chromatography (HIC) step. Whereas ion exchange chromatography relies on the charges of proteins, e.g., antibodies, to isolate them, hydrophobic interaction chromatography uses the hydrophobic properties of some proteins, e.g., antibodies. Hydrophobic groups on the antibody bind to hydrophobic groups on the column. The more hydrophobic a protein is, the stronger it will bind to the column. The HIC step removes, for example, host cell derived impurities (e.g., DNA and other high and low molecular weight product-related species).

Hydrophobic interactions are strongest at high ionic strength, therefore, this form of separation is conveniently performed following salt precipitations or ion exchange procedures. Adsorption of the antibody to a HIC column is favored by high salt concentrations, but the actual concentrations can vary over a wide range depending on the nature of the antibody and the particular HIC ligand chosen. Various ions can be arranged in a so-called soluphobic series depending on whether they promote hydrophobic interactions (salting-out effects) or disrupt the structure of water (chaotropic effect) and lead to the weakening of the hydrophobic interaction. Cations are ranked in terms of increasing salting out effect as $Ba^{++} <; Ca^{++} <; Mg^{++} <; Li^+ <; Cs^+ <; Na^+ <; K^+ <; Rb^+ <; NH_4^+$, while anions may be ranked in terms of increasing chaotropic effect as $PO^{---} <; SO_4^{--} <; CH_3COO^- <; Cl^- <; Br^- <; NO_3^- <; ClO_4^- <; I^- <; SCN^-$ In general, Na, K or $NH_4$ sulfates effectively promote ligand-protein interaction in HIC. Salts may be formulated that influence the strength of the interaction as given by the following relationship: $(NH_4)_2SO_4 >; Na_2SO_4 >; NaCl >; NH_4Cl >; NaBr >; NaSCN$. In general, salt concentrations of between about 0.75 and about 2M ammonium sulfate or between about 1 and 4M NaCl are useful.

HIC columns normally comprise a base matrix (e.g. cross-linked agarose or synthetic copolymer material) to which hydrobobic ligands (e.g. alkyl or aryl groups) are coupled. The preferred HIC column comprises an agarose resin substituted with phenyl groups (e.g. a Phenyl Sepharose™ column). Many HIC columns are available commercially. Examples include, but are not limited to, Phenyl Sepharose™ 6 Fast Flow column with low or high substitution (Pharmacia LKB Biotechnology, AB, Sweden); Phenyl Sepharose™ High Performance column (Pharmacia LKB Biotechnology, AB, Sweden); Octyl Sepharose™ High Performance column (Pharmacia LKB Biotechnology, AB, Sweden); Fractogel™ EMD Propyl or Fractogel™ EMD Phenyl columns (E. Merck, Germany); Macro-Prep™ Methyl or Macro-Prep™ t-Butyl Supports (Bio-Rad, California); WP HI-Propyl (C.sub.3)™ column (J. T. Baker, New Jersey); and Toyopearl™ ether, phenyl or butyl columns (TosoHaas, PA).

Following any preliminary purification step(s), the mixture comprising the antibody of interest and HCP(s) may be subjected to HIC. Often, the antibody composition to be purified will be present in a buffer from the previous purification step. However, it may be necessary to add a buffer to the antibody composition prior to the HIC step. Many buffers are available and can be selected by routine experimentation. In one embodiment, the pH of the mixture comprising the antibody to be purified and at least one HCP in a loading buffer is adjusted to a pH of about 7 using either an acid or base, depending on the starting pH, and a conductivity of about 136 to about 158 mS/cm. In one embodiment, the antibody mixture is diluted with a buffer comprising 40 mM sodium phosphate, 2.2 M $(NH_4)_2SO_4$, pH 7.

Prior to loading the antibody mixture, the column may be equilibrated with equilibration buffer. In some embodiments, the equilibration buffer is 20 mM sodium phosphate, 1.1 M $(NH_4)_2SO_4$, pH 7.

In one embodiment, the mixture, e.g., first flowthrough comprising the antibody, is loaded onto a phenyl sepharose HIC column. In certain embodiments, the protein loading for this step ranges between about 20 and about 40 g protein per L of resin. In other embodiments, the protein loading for this step is about 35 g protein per L of resin. In some embodiments, two or three chromatography cycles may be required to process the entire quantity of available material.

Following binding of the protein to the hydrophobic interaction column, the column may be washed with a wash buffer that may be the same as the equilibration buffer, e.g., 1.1 M $(NH_4)_2SO_4$, pH 7.

The antibody is eluted from the column using an elution buffer such that a second eluate is obtained. The elution buffer can be selected using routine experimentation. The pH of the elution buffer ranges between about 6 and about 8 and has a low ammonium sulfate concentration (i.e., less than about 1 M $(NH_4)_2SO_4$). The conductivity of the elution buffer ranges from about 87 to about 101 mS/cm. In one embodiment, the elution buffer contains 11 mM sodium phosphate, 0.625 M $(NH_4)_2SO_4$, pH 7. It has been discovered that lower salt concentrations result in less adalimumab binding to the resin. The antibody is eluted from the second ion exchange material such that a second eluate having a reduced level of HCP is obtained. The second eluate also has a reduced level of procathepsin L. In one embodiment, the second obtained using the method of the invention comprises an about 10 to an about 96 fold decrease in HCP levels in comparison to a comparable step of process A. In another embodiment, the second eluate obtained using the method of the invention comprises an about 5 to an about 15 fold decrease in cathepsin L activity in comparison to a comparable step of process A. In one embodiment, the second eluate comprises a range of about 3 to about 5 fold less HCP than the first flowthrough as determined by a HCP ELISA. In another embodiment, the second eluate comprises cathepsin L activity ranging from between about 0.5 to about 1.5 RFU/s/mg of antibody as measured by a cathepsin L kinetic assay.

Acceptable operating ranges for the phenyl sepharose chromatography column used in the methods of the invention are shown below in Table 3.

TABLE 3

Acceptable operating ranges for Phenyl Sepharose HP chromatography

| Operating parameter | AOR |
|---|---|
| Column loading | 20-40 g/L |
| Load sample dilution | 0.9:1 to 1.1:1 |
| Linear velocity | 25-125 cm/hr |

Further purification steps can include virus removing steps as well as nanofiltration, ultrafiltration and/or diafiltration steps, as described herein.

III.C. Viral Inactivation

In order to provide a margin of safety, potential undetected viruses are inactivated during the purification process. Methods of viral inactivation are known in the art and include heat inactivation (pasteurization), pH inactivation, solvent/detergent treatment, UV and gamma ray irradiation and the addition of certain chemical inactivating agents such as β-propiolactone or e.g. copper phenanthroline as in U.S. Pat. No. 4,534,972, etc. In some embodiments, subjecting the mixture to viral inactivation can include pH viral inactivation. Methods of pH viral inactivation techniques are also well known in the art. For instance, typical methods of viral inactivation include incubating the mixture for a period of time at low pH, subsequently neutralizing the pH and removing particulates by filtration. The choice of pH level largely depends on the stability profile of the antibody product and buffer components. It is known that the quality of the target antibody during low pH virus inactivation is affected by pH and the duration of the low pH incubation. Virus inactivation is dependent on these same parameters in addition to protein concentration, which may reduce inactivation at high concentrations. Thus, the proper parameters of protein concentration, pH and duration of inactivation may be selected by routine experimentation.

The pH of the mixture may be lowered by any suitable acid including, but not limited to, citric acid, acetic acid, caprylic acid, or other suitable acids. In preferred embodiments, the pH of the mixture is adjusted with 1 M citric acid.

In some embodiments, the mixture is incubated at pH from about 2.9 to about 3.9 for about 15 minutes to about 180 minutes. In further embodiments, the mixture is incubated at about pH 3.5 for about 60 minutes to about 120 minutes. In still further embodiments, the mixture is incubated at about pH 3.5 for about 60 minutes to about 180 minutes.

In one embodiment, the mixture comprising the antibody and HCPs is subjected to viral inactivation prior to IE separation. In other embodiments, the initial eluate is subjected to viral inactivation prior to IE separation. In certain embodiments, the initial eluate is subjected to viral inactivation prior to anion exchange chromatography.

Following viral inactivation, the mixture is adjusted as needed for further purification steps. For example, the pH-adjusted pool may be subjected to filtration. In one embodiment, following low pH viral inactivation and/or filtration, the pH of the mixture is typically adjusted to a more neutral pH, e.g., from about 6.5 to about 8.5. For example, the mixture may be flushed with water for injection (WFI) to obtain the desired pH.

The low pH virus inactivation parameters used in the method of the invention are shown in Table 4 below.

TABLE 4

Acceptable operating parameters for low pH virus inactivation

| Operating parameter | AOR |
|---|---|
| Incubation pH | 3.0-3.7 |
| Incubation time | 60-180 min |
| Protein concentration | ≦33 g/L |

The invention includes a method where the first eluate from the ion exchange column is subjected to viral inactivation prior to the second ion exchange chromatography step. In one embodiment, viral inactivation is achieved through pH viral inactivation.

IV. Method for Determining Host Cell Protein (HCP) Levels

The present invention also provides methods for determining the residual levels of Host Cell Protein (HCP) concentration in the purified antibody composition. As described above, HCPs are desirably excluded from the final target substance product, e.g., the antibody. Exemplary HCPs include proteins originating from the source of the antibody production. Failure to identify and sufficiently remove HCPs from the target antibody may lead to reduced efficacy and/or adverse patient reactions.

As used herein, the term "HCP ELISA" refers to an ELISA where the second antibody used in the assay is specific to the HCPs produced from cells, e.g., CHO cells, used to generate the antibody, e.g., adalimumab. The second antibody may be produced according to conventional methods known to those of skill in the art. For example, the second antibody may be produced using HCPs obtained by sham production and purification runs, i.e., the same cell line used to produce the antibody of interest is used, but the cell line is not transfected with antibody DNA. In an exemplary embodiment, the second antibody is produced using HPCs similar to those expressed in the cell expression system of choice, i.e., the cell expression system used to produce the target antibody.

Generally, HCP ELISA comprises sandwiching a liquid sample comprising HCPs between two layers of antibodies, i.e., a first antibody and a second antibody. The sample is incubated during which time the HCPs in the sample are captured by the first antibody, e.g., goat anti-CHO, affinity purified (Cygnus). A labeled second antibody specific to the HCPs produced from the cells used to generate the antibody, e.g., anti-CHO HCP Biotinylated, is added, and binds to the HCPs within the sample. The amount of HCP contained in the sample is determined using the appropriate test based on the label of the second antibody.

HCP ELISA may be used for determining the level of HCPs in an antibody composition, such as an eluate or flowthrough obtained using the process described in section III above. The present invention also provides a composition comprising an antibody, wherein the composition has no detectable level of HCPs as determined by an HCP Enzyme Linked Immunosorbent Assay ("ELISA"). In one embodiment, the first eluate comprises between about 12,000 to about 19,500 ng/mg of HCP. In one embodiment, the second eluate comprises between about 1.0 and about 0.0 ng/mg of HCP.

V. Method for Determining Procathepsin L Levels

The invention provides a kinetic assay (or cathepsin L kinetic assay) for determining the amount of procathepsin L in a sample. Procathepsin L is a host cell protein derived from certain expression systems and, upon activation to cathepsin L, is known to cause fragmentation of proteins, including antibodies such as adalimumab. Studies have demonstrated that procathepsin L is synthesized as an inactive zymogen and later processed to the active cathepsin L form. Activation of procathepsin L occurs by proteolytic removal of the N-terminal pro-peptide region by either other proteases such as cathepsin D or by autocatalytic activation within the acidic conditions of the lysosome (Turk et al. (1999) *Eur J Biochem* 259:929). Furthermore, Mason et al. (see Mason et al. (1992) *Biochem Biophysical Res Comm* 189: 1659) report the activation of cathepsin L can be achieved to a higher degree at pH 5.5 with the addition of negatively charged molecules, such as dextran sulfate, at lower pH conditions.

Previous methods of detecting levels of procathepsin L (or the active form cathepsin L) included analytical methods such as weak anion exchange chromatography. Such methods are limited, however, when testing in-process samples, i.e., samples obtained from the process described above in section III, due to buffer system interference and matrix effects. Thus, the invention provides a high throughput fluorescent enzymatic method to better monitor procathepsin L, for example, for the purpose of process monitoring.

The kinetic assay of the invention provides a method of determining procathepsin L at levels which cannot be readily detected by standard end point assays. The kinetic assay also provides a means of determining whether the level of procathepsin L is reproducibly low. In one embodiment, samples may be obtained from any point in the process described in Section III, in order to confirm or determine that the level of procathepsin L is being reduced in the overall process. Procathepsin L is activated by removing the amino terminal from the protein. In one embodiment, activation is achieved using a peptidase, such as, but not limited to, cathepsin D. Once activated, cathepsin L can selectively hydrolyze substrates. A substrate is contacted with the sample and monitored for cathepsin L activity based on changes to the substrate.

In a preferred embodiment, the substrate for cathepsin L comprises a label. The label may include any agent which allows the cathepsin activity to be determined. Examples of labeled substrates which cathepsin L can selectively hydrolyze include synthetic substrates such as Z-leucine-arginine-AMC (R & D Systems). The peptide substrate may contain a fluorescent 7-amino-4-methyl coumarin (AMC) group that is quenched by the amide bond between the amino group of the AMC and the carboxyl group of the arginine Upon cleavage of the amide bond by cathepsin L, the released AMC group is fluorescent and can be measured by excitation and emission wavelengths of 380 nm and 460 nm respectively. This excitation may be measured and used to determine the level of cathepsin L activity. The rate of substrate turnover is directly proportional to the amount of cathepsin L present in the sample. This measurement is used in combination with a reference sample having known cathepsin L activity and known amount of cathepsin L. The cathepsin L activity in the sample is then correlated to the amount of antibody present in the sample. In one embodiment, the first eluate comprises cathepsin L activity ranging from between about 25 to about 60 RFU/s/mg antibody. In another embodiment, the first flowthrough comprises cathepsin L activity ranging from between about 0.4 to about 4 RFU/s/mg antibody. In one embodiment, the second eluate comprises cathepsin L activity ranging from between about 0.5 to about 1.5 RFU/s/mg antibody.

In one embodiment, the kinetic assay comprises determining the amount of procathepsin L in a material derived from a mammalian cell expression system comprising by contacting the material with an enzyme to process procathepsin L to the active cathepsin L form, such that a cathepsin L sample is obtained. Once activated, cathepsin L can selectively hydrolyze substrates, including synthetic substrates such as Z-leucine-arginine-AMC. A substrate is then added to the sample, including, for example Z-leucine-arginine-AMC, which contains a fluorescent 7-amino-4-methyl coumarin (AMC) group that is quenched by the amide bond between the amino group of the AMC and the carboxyl group of the arginine. Upon cleavage of the amide bond by cathepsin L, the released AMC group is fluorescent and can be measured by excitation and emission wavelengths of 380 nm and 460 nm respectively. The determined cathepsin L activity is used as an indication of the amount of procathepsin L in the material derived from the mammalian cell expression system, e.g., Chinese Hamster Ovary (CHO) cells.

In one embodiment, the first eluate comprises cathepsin L activity ranging from between about 25 to about 60 RFU/s/ mg antibody. In another embodiment, the first flowthrough comprises cathepsin L activity ranging from between about 0.4 to about 4 RFU/s/mg antibody. In one embodiment, the second eluate comprises cathepsin L activity ranging from between about 0.5 to about 1.5 RFU/s/mg antibody.

The invention also encompasses ranges intermediate to the above recited amounts are also intended to be part of this invention. For example, ranges of values using a combination of any of the above recited values as upper and/or lower limits are intended to be included, as well as any number between the described range.

The invention includes any of the above-mentioned modifications, alone or in combination with one another.

VI. Pharmaceutical Compositions

Antibodies obtained using the process of the invention may be incorporated into pharmaceutical compositions suitable for administration to a subject. Typically, the pharmaceutical composition comprises an antibody, or antigen-binding portion thereof, and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it is preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of antibody, or antigen-binding portion thereof.

Pharmaceutical compositions comprising antibodies, or antigen-binding portions thereof, purified using the methods of the invention may be found in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies or other TNFα inhibitors. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody, or antigen-binding portion thereof) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

Supplementary active compounds can also be incorporated into the compositions. In certain embodiments, an antibody, or antigen-binding portion thereof, for use in the methods of the invention is coformulated with and/or coadministered with one or more additional therapeutic agents. For example, an anti-hTNFα antibody or antibody portion of the invention may be coformulated and/or coadministered with one or more DMARD or one or more NSAID or one or more additional antibodies that bind other targets (e.g., antibodies that bind other cytokines or that bind cell surface molecules), one or more cytokines, soluble TNFα receptor (see e.g., PCT Publication No. WO 94/06476) and/or one or more chemical agents that inhibit hTNFα production or activity (such as cyclohexane-ylidene derivatives as described in PCT Publication No. WO 93/19751) or any combination thereof. Furthermore, one or more antibodies of the invention may be used in combination with two or more of the foregoing therapeutic agents. Such combination therapies may advantageously utilize lower dosages of the administered therapeutic agents, thus avoiding possible side effects, complications or low level of response by the patient associated with the various monotherapies.

In one embodiment, the invention includes pharmaceutical compositions comprising an effective amount of a TNFα antibody, or antigen-binding portion thereof, and a pharmaceutically acceptable carrier, wherein the effective amount of the TNFα antibody may be effective to treat a TNFα-related disorder, including, for example, Crohn's disease. In one embodiment, the antibody or antibody portion is incorporated into a pharmaceutical formulation as described in PCT/IB03/04502 and U.S. application Ser. No. 10/222,140, incorporated by reference herein. This formulation includes a concentration 50 mg/ml of the antibody adalimumab, wherein one pre-filled syringe contains 40 mg of antibody for subcutaneous injection.

The antibodies, or antibody-portions, obtained using the methods of the present invention can be administered by a variety of methods known in the art, although for many therapeutic applications, the preferred route/mode of administration is subcutaneous injection. In another embodiment, administration is via intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

The antibodies, or antigen-binding portion thereof, obtained using the methods of the invention can also be administered in the form of protein crystal formulations which include a combination of protein crystals encapsulated within a polymeric carrier to form coated particles. The coated particles of the protein crystal formulation may have a spherical morphology and be microspheres of up to 500 micro meters in diameter or they may have some other morphology and be microparticulates. The enhanced concentration of protein crystals allows the antibody of the invention to be delivered subcutaneously. In one embodiment, the antibodies of the invention are delivered via a protein delivery system, wherein one or more of a protein crystal formulation or composition, is administered to a subject with a TNFα-related disorder. Compositions and methods of preparing stabilized formulations of whole antibody crystals or antibody fragment crystals are also described in WO 02/072636, which is incorporated by reference herein. In one embodiment, a formulation comprising the crystallized antibody fragments described in PCT/IB03/04502 and U.S. application Ser. No. 10/222,140, incorporated by reference herein, are used to treat a TNFα-related disorder using the multiple-variable dose methods of the invention.

In certain embodiments, an antibodies, or antigen-binding portion thereof, obtained using the methods of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

The pharmaceutical compositions of the invention may include a "therapeutically effective amount" or a "prophylactically effective amount" of an antibody or or antigen-binding portion thereof of the invention. A "therapeutically effective amount" refers to an amount effective, at dosages and for periods of time necessary, to achieve the desired therapeutic result. A therapeutically effective amount of the antibody, or antigen-binding portion thereof, may vary according to factors such as the disease state, age, sex, and weight of the individual, and the ability of the antibody, antibody portion, other TNFα inhibitor to elicit a desired response in the individual. A therapeutically effective amount is also one in which any toxic or detrimental effects of the antibody, or antigen-binding portion thereof, are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit comprising a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an antibody, or antigen-binding portion thereof, is 10 to 200 mg, more preferably 20 to 160 mg, more preferably 40 to 80 mg, and most preferably 80 mg. In one embodiment, the therapeutically effective amount of an antibody or, antigen-binding portion thereof, is about 20 mg. In another embodiment, the therapeutically effective amount of an antibody or portion thereof is about 40 mg. In still another embodiment, the therapeutically effective amount of an antibody or, antigen-binding portion thereof, is about 80 mg. In one embodiment, the therapeutically effective amount of an antibody or portion thereof for use in the methods of the invention is about 120 mg. In yet another embodiment, the therapeutically effective amount of an antibody, or antigen-binding portion thereof, is about 160 mg. Ranges intermediate to the above recited dosages, e.g. about 78.5 to about 81.5; about 15 to about 25; about 30 to about 50; about 60 to about 100; about 90 to about 150; about 120 to about 200, are also intended to be part of this invention. For example, ranges of values using a combination of any of the above recited values as upper and/or lower limits are intended to be included.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Antibodies, or antibody-portions thereof, obtained using the methods of the invention may be administered on a biweekly dosing regimen as described in WO 02/100330, a low dose regimen as described in WO 04/037205, and a multiple variable dosing regimen as described in WO 05/110452, each of which is incorporated by reference herein.

The invention also pertains to packaged pharmaceutical compositions, articles of manufacture, or kits comprising the antibody, or antigen-binding portion thereof, obtained using the process of the invention. The article of manufacture may comprise an antibody, or antigen-binging portion thereof, obtained using the method of the invention and packaging material. The article of manufacture may also comprise label or package insert indicating the formulation or composition comprising the antibody, or antigen-binding portion thereof, has a reduced level of HCP and/or procathepsin L. The article of manufacture may comprise a label or package insert contained within the packaging material indicating that the adalimumab formulation comprises no greater than about 70 ng/mg of HCP or a label or package insert contained within the packaging material indicating that the adalimumab formulation comprises no greater than about 13 ng/mg. The article of manufacture may comprise a label or package insert contained within the packaging material indicating that the adalimumab formulation comprises no greater than about 5 ng HCP/mg adalimumab. The article of manufacture may also comprise packaging material indicating that the adalimumab formulation comprises no greater a level of procathepsin L than that indicated by a cathepsin L activity of about 3.0 RFU/s/mg adalimumab.

VII. Methods of Treatment

The invention a method of producing an HCP- or procathepsin L-reduced antibody preparation which can be used for inhibiting TNFα activity in a subject suffering from a disorder in which TNFα activity is detrimental. TNFα has been implicated in the pathophysiology of a wide variety of disorders (see e.g., Moeller, A., et al. (1990) Cytokine 2:162-169; U.S. Pat. No. 5,231,024 to Moeller et al.; European Patent Publication No. 260 610 B1 by Moeller, A.). TNFα has been implicated in the pathophysiology of a wide variety of a TNFα-related disorders including sepsis, infections, autoimmune diseases, transplant rejection and graft-versus-host disease (see e.g., Moeller, A., et al. (1990) Cytokine 2:162-169; U.S. Pat. No. 5,231,024 to Moeller et al.; European Patent Publication No. 260 610 B1 by Moeller, A., et al. Vasilli, P. (1992) Annu. Rev. Immunol. 10:411-452; Tracey, K. J. and Cerami, A. (1994) Annu. Rev. Med. 45:491-503). The invention a method of producing an HCP- or procathepsin L-reduced antibody preparation methods which are beneficial for inhibiting TNFα activity in a subject suffering from a TNFα-related disorder, which method comprises administering to a subject an initial induction dose and subsequently administering a treatment dose of an antibody, or antigen-binding fragment thereof, such that TNFα activity is inhibited. Preferably, the TNFα is human TNFα and the subject is a human subject. In one embodiment, the TNFα inhibitor is adalimumab, also referred to as HUMIRA® (D2E7).

As used herein, the term "a disorder in which TNFα activity is detrimental" is intended to include diseases and other disorders in which the presence of TNFα in a subject suffering from the disorder has been shown to be or is suspected of being either responsible for the pathophysiology of the disorder or a factor that contributes to a worsening of the disorder. Accordingly, a disorder in which TNFα activity is detrimental is a disorder in which inhibition of TNFα activity is expected to alleviate the symptoms and/or progression of the disorder. Such disorders may be evidenced, for example, by an increase in the concentration of TNFα in a biological fluid of a subject suffering from the disorder (e.g., an increase in the concentration of TNFα in serum, plasma, synovial fluid, etc. of the subject), which can be detected, for example, using an anti-TNFα antibody as described above. There are numerous examples of disorders in which TNFα activity is detrimental. The use of TNFα antibodies and antibody portions obtained using methods of the invention for the treatment of specific disorders is discussed further below:

A. Sepsis

Tumor necrosis factor has an established role in the pathophysiology of sepsis, with biological effects that include hypotension, myocardial suppression, vascular leakage syndrome, organ necrosis, stimulation of the release of toxic secondary mediators and activation of the clotting cascade (see e.g., Moeller, A., et al. (1990) Cytokine 2:162-169; U.S. Pat. No. 5,231,024 to Moeller et al.; European Patent Publication No. 260 610 B1 by Moeller, A.; Tracey, K. J. and Cerami, A. (1994) Annu. Rev. Med. 45:491-503; Russell, D and Thompson, R. C. (1993) Curr. Opin. Biotech. 4:714-721). The multiple-variable dose methods of the invention can be used to treat sepsis in any of its clinical settings, including septic shock, endotoxic shock, gram negative sepsis and toxic shock syndrome.

Furthermore, to treat sepsis, an anti-hTNFα antibody, or antibody portion, obtained using the process of the invention can be coadministered with one or more additional therapeutic agents that may further alleviate sepsis, such as an interleukin-1 inhibitor (such as those described in PCT Publication Nos. WO 92/16221 and WO 92/17583), the cytokine interleukin-6 (see e.g., PCT Publication No. WO 93/11793) or an antagonist of platelet activating factor (see e.g., European Patent Application Publication No. EP 374 510). In a preferred embodiment, an anti-TNFα antibody or antibody portion is administered to a human subject within a subgroup of sepsis patients having a serum or plasma concentration of IL-6 above 500 pg/ml, and more preferably 1000 pg/ml, at the time of treatment (see PCT Publication No. WO 95/20978 by Daum, L., et al.).

B. Autoimmune Diseases

Tumor necrosis factor has been implicated in playing a role in the pathophysiology of a variety of autoimmune diseases. For example, TNFα has been implicated in activating tissue inflammation and causing joint destruction in rheumatoid arthritis (see e.g., Moeller, A., et al. (1990) Cytokine 2:162-169; U.S. Pat. No. 5,231,024 to Moeller et al.; European Patent Publication No. 260 610 B1 by Moeller, A.; Tracey and Cerami, supra; Arend, W. P. and Dayer, J-M. (1995) Arth. Rheum. 38:151-160; Fava, R. A., et al. (1993) Clin. Exp. Immunol. 94:261-266). TNFα also has been implicated in promoting the death of islet cells and in mediating insulin resistance in diabetes (see e.g., Tracey and Cerami, supra; PCT Publication No. WO 94/08609). TNFα also has been implicated in mediating cytotoxicity to oligodendrocytes and induction of inflammatory plaques in multiple sclerosis (see e.g., Tracey and Cerami, supra). TNFα also has been implicated in mediating cytotoxicity to oligodendrocytes and induction of inflammatory plaques in multiple sclerosis (see e.g., Tracey and Cerami, supra). Chimeric and humanized murine anti-hTNFα antibodies have undergone clinical testing for treatment of rheumatoid arthritis (see e.g., Elliott, M. J., et al. (1994) Lancet 344:1125-1127; Elliot, M. J., et al. (1994) Lancet 344:1105-1110; Rankin, E. C., et al. (1995) Br. J. Rheumatol. 34:334-342).

TNFα antibodies, such as adalimumab, may be used to treat autoimmune diseases, in particular those associated with inflammation. Examples of such autoimmune conditions include rheumatoid arthritis, rheumatoid spondylitis, osteoarthritis and gouty arthritis, allergy, multiple sclerosis, autoimmune diabetes, autoimmune uveitis and nephrotic syndrome. Other examples of autoimmune conditions include multisystem autoimmune diseases and autoimmune hearing loss.

Typically, the antibody, or antibody portion, is administered systemically, although for certain disorders, local administration of the antibody or antibody portion at a site of inflammation may be beneficial (e.g., local administration in the joints in rheumatoid arthritis or topical application to diabetic ulcers, alone or in combination with a cyclohexaneylidene derivative as described in PCT Publication No. WO 93/19751). TNFα inhibitors, including human antibodies, and antibody portions such as D2E7, also can be administered with one or more additional therapeutic agents useful in the multiple-variable dose treatment of autoimmune diseases, as discussed further below.

In one embodiment of the invention, a TNFα antibody obtained using the methods of the invention is used to treat autoimmune disorders such as lupus. Lupus is has been shown to be associated with TNF activity (Shvidel et al. (2002) Hematol J. 3:32; Studnicka-Benke et al. (1996) Br J Rheumatol. 35:1067). The term "lupus" as used herein refers to a chronic, inflammatory autoimmune disorder called lupus erythematosus that may affect many organ systems including the skin, joints and internal organs. Lupus is a general term which includes a number of specific types of lupus, including systemic lupus, lupus nephritis, and lupus cerebritis. In systemic lupus (SLE), the body's natural defenses are turned against the body and rogue immune cells attack the body's tissues. Antibodies may be produced that can react against the body's blood cells, organs, and tissues. This reaction leads to immune cells attacking the affected systems, producing a chronic disease. Lupus nephritis, also referred to as lupus glomerular disease, is kidney disorder that is usually a complication of SLE, and is characterized by damage to the glomerulus and progressive loss of kidney function. Lupus cerebritis refers to another complication of SLE, which is inflammation of the brain and/or central nervous system.

Another autoimmune disease which can be treated using a TNFα antibody is Crohn's disease, which is described in more detail below in the Intestinal Disorders Section.

C. Infectious Diseases

Tumor necrosis factor has been implicated in mediating biological effects observed in a variety of infectious diseases. For example, TNFα has been implicated in mediating brain inflammation and capillary thrombosis and infarction in malaria. TNFα also has been implicated in mediating brain inflammation, inducing breakdown of the blood-brain barrier, triggering septic shock syndrome and activating venous infarction in meningitis. TNFα also has been implicated in inducing cachexia, stimulating viral proliferation and mediating central nervous system injury in acquired immune deficiency syndrome (AIDS). Accordingly, antibodies, and antibody portions, directed against TNF, can be used for treatment of infectious diseases, including bacterial meningitis (see e.g., European Patent Application Publication No. EP 585 705), cerebral malaria, AIDS and AIDS-related complex (ARC) (see e.g., European Patent Application Publication No. EP 230 574), as well as cytomegalovirus infection secondary to transplantation (see e.g., Fietze et al. (1994) *Transplantation* 58:675). The antibodies, and antibody portions, of the invention, also can be used to alleviate symptoms associated with infectious diseases, including fever and myalgias due to infection (such as influenza) and cachexia secondary to infection (e.g., secondary to AIDS or ARC).

D. Transplantation

Tumor necrosis factor has been implicated as a key mediator of allograft rejection and graft versus host disease (GVHD) and in mediating an adverse reaction that has been observed when the rat antibody OKT3, directed against the T cell receptor CD3 complex, is used to inhibit rejection of renal transplants (see e.g., Eason et al. (1995) *Transplantation* 59:300; Suthanthiran and Strom (1994) *New Engl. J. Med.* 331:365). Accordingly, the antibodies, and antibody portions, of the invention, can be used to inhibit transplant rejection using multiple-variable dose treatment, including rejections of allografts and xenografts and to inhibit GVHD. Although the antibody or antibody portion may be used alone, more preferably it is used in combination with one or more other agents that inhibit the immune response against the allograft or inhibit GVHD. For example, in one embodiment, an antibody or antibody portion of the invention is used in combination with OKT3 to inhibit OKT3-induced reactions. In another embodiment, an antibody or antibody portion of the invention is used in combination with one or more antibodies directed at other targets involved in regulating immune responses, such as the cell surface molecules CD25 (interleukin-2 receptor-α), CD11a (LFA-1), CD54 (ICAM-1), CD4, CD45, CD28/CTLA4, CD80 (B7-1) and/or CD86 (B7-2). In yet another embodiment, an antibody or antibody portion of the invention is used in combination with one or more general immunosuppressive agents, such as cyclosporin A or FK506.

E. Malignancy

Tumor necrosis factor has been implicated in inducing cachexia, stimulating tumor growth, enhancing metastatic potential and mediating cytotoxicity in malignancies. Accordingly, antibodies, and antibody portions, which directed against TNF, can be used in the treatment of malignancies, wherein treatment inhibits tumor growth or metastasis and/or alleviates cachexia secondary to malignancy. The antibody, or antibody portion, may be administered systemically or locally to the tumor site.

F. Pulmonary Disorders

Tumor necrosis factor has been implicated in the pathophysiology of adult respiratory distress syndrome (ARDS), including stimulating leukocyte-endothelial activation, directing cytotoxicity to pneumocytes and inducing vascular leakage syndrome. The antibody obtained using the methods of the invention may be used to treat various pulmonary disorders, including adult respiratory distress syndrome (see e.g., PCT Publication No. WO 91/04054), shock lung, chronic pulmonary inflammatory disease, pulmonary sarcoidosis, pulmonary fibrosis and silicosis. The antibody, or antibody portion, may be administered systemically or locally to the lung surface, for example as an aerosol. An antibody, or antibody portion, also can be administered with one or more additional therapeutic agents useful in the treatment of pulmonary disorders, as discussed further below.

Other examples of pulmonary disorders in which TNFα has been implicated in the pathophysiology include idiopathic interstitial lung disease and chronic obstructive airway disorders (see e.g., Piquet et al. (1989) *J Exp Med.* 170:655; Whyte et al. (2000) *Am J Respir Crit Care Med.* 162:755; Anticevich et al. (1995) *Eur J Pharmacol.* 284:221). The invention further provides methods for treating TNFα activity in a subject suffering from such a pulmonary disorder, which method comprises administering to the subject an antibody, or antibody portion, such that TNFα activity in the subject suffering from idiopathic interstitial lung disease or a chronic obstructive airway disorder is inhibited. Examples of idiopathic interstitial lung diseases and chronic obstructive airway disorders in which TNFα activity is detrimental are discussed further below.

1. Idiopathic Interstitial Lung Disease

In one embodiment, the TNFα antibody obtained using the method of the invention is used to treat subjects who have an idiopathic interstitial lung disease. The term "idiopathic pulmonary fibrosis" or "IPF" refers to a group of disorders characterized by inflammation and eventually scarring of the deep lung tissues, leading to shortness of breath. The scarring of the alveoli (air sacs) and their supporting structures (the interstitium) in IPF eventually leads to a loss of the functional alveolar units and a reduction of the transfer of oxygen from air to blood. IPF is also referred to as diffuse parenchymal lung disease; alveolitis; cryptogenic fibrosing alveolitis (CFA); idiopathic pulmonary pneumonitis (IPP); and usual interstitial pneumonitis (UIP). IPF is often used synonymously with UIP ("IPF/UIP") because UIP is the most common cellular pattern seen in the pathologic diagnosis of IPF.

Idiopathic interstitial lung diseases affect the lungs in three ways: first, the lung tissue is damaged in some known or unknown way; second, the walls of the air sacs in the lung become inflamed; and finally, scarring (or fibrosis) begins in the interstitium (or tissue between the air sacs), and the lung becomes stiff. Examples of idiopathic interstitial lung diseases include idiopathic pulmonary fibrosis (IPF). Tumor necrosis factor has been implicated in the pathophysiology of idiopathic pulmonary fibrosis (IPF) (see Piquet et al. (1989) *J Exp Med.* 170:655; Whyte et al. (2000) *Am J Respir Crit Care*

Med 162:755 Corbett et al. (2002) *Am J Respir Crit Care Med.* 165:690). For example, it has been found that IPF patients have increased levels of TNF expressiojn in macrophages and in type II epithelial cells (Piquet et al. (1993) *Am J Pathol* 143:651; Nash et al. (1993) *Histopathology* 22:343; Zhang et al. (1993) *J Immunol* 150:4188). Certain genetic polymorphisms are also associated with increased TNF expression, and are implicated in playing a role in IPF and silicosis (Whyte et al., supra; Corbett et al., supra).

Patients with IPF often exhibit certain symptoms, including a dry cough, chest pain, and/or shortness of breath. Commonly used drugs for the treatment of IPF are prednisone and cytoxan, although only a fraction of patients improve with continued use of these drugs (American Thoracic Society (2000) *Am. J. Respir. Crit. Care Med.* 161:646). Oxygen administration and transplantation of the lung are other choices for treatment. In one embodiment, antibodies obtained through the methods of the invention may be used in combination with another therapeutic agent, for example oxygen, for the treatment of idiopathic pulmonary fibrosis.

Examples of animal models used to study idiopathic interstitial lung disease and chronic obstructive airway disorders include ovalbumin (OVA) induced allergic asthma mice and cigarette smoke induced chronic obstructive pulmonary disease mice (see Hessel et al. (1995) *Eur J Pharmacol.* 293:401; Keast et al. (1981) *J. Pathol.* 135:249).

2. Chronic Obstructive Airway Disorder

In one embodiment, a TNFα antibody is used to treat a subject who has a chronic obstructive airflow disorder. In these diseases, airflow obstruction may be chronic and persistent or episodic and recurrent. Airflow obstruction is usually determined by forced expiratory spirometry, which is the recording of exhaled volume against time during a maximal expiration. In a subject who does not have an obstructed airflow, a full forced expiration usually takes between 3 and 4 seconds. In a patient with chronic obstructive airflow disorder, wherein airflow is obstructed, it usually takes up to 15 to 20 seconds and may be limited by breath-holding time. The normal forced expiratory volume in the first second of expiration ($FEV_1$) is easily measured and accurately predicted on the basis of age, sex, and height. The ratio of $FEV_1$ to forced vital capacity ($FEV_1/FVC$) normally exceeds 0.75. Recording airflow against volume during forced expiration and a subsequent forced inspiration—the flow-volume loop—is also useful, mainly for distinguishing upper from lower airway narrowing. Examples of chronic obstructive airway disorders are described below.

a. Asthma

Tumor necrosis factor has been implicated in the pathophysiology of asthma, (Anticevich et al. (1995) *Eur J Pharmacol.* 284:221; Thomas et al. 1995. *Am J Respir Crit Care Med.* 152:76; Thomas and Heywood (2002) *Thorax.* 57:774). For example, acute asthma attacks have been found to be associated with pulmonary neutrophilia and elevated BAL TNF levels (Ordonez et al. (2000) *Am J Respir Crit Care Med* 161:1185). It has been found that the severity of asthma symptoms correlates with endotoxin levels in house dust. In rats, anti-TNF antibodies reduced endotoxin-induced airway changes (Kips et al. (1992) *Am Rev Respir Dis* 145:332).

The term "asthma" as used herein, refers to a disorder in which inflammation of the airways causes airflow into and out of the lungs to be restricted. Asthma is also referred to as bronchial asthma, exercise induced asthma—bronchial, and reactive airways disease (RAD). In some instances, asthma is associated with allergies and/or is familial. Asthma includes a condition which is characterized by widespread fluctuations in the diameter or caliber of bronchial airways over short periods of time, resulting in changes in lung function. The resulting increased resistance to air flow produces symptoms in the affected subject, including breathlessness (dyspnea), chest constriction or "tightness," and wheezing.

Patients with asthma are characterized according to NIH guidelines, are described as mild intermittent, mild persistent, moderate persistent, and severe persistent (see NAEPP Expert Panel Report Guidelines for the Diagnosis and Management of Asthma-Update on Selected Topics 2002. JACI 2002; 110: S141-S209; Guidelines for the Diagnosis and Management of Asthma. NIH Publication 97-4051, July 1997). Patients diagnosed with moderate persistent asthma are often treated with inhaled corticosteroids. Patients diagnosed with severe persistent asthma are often treated with high dose inhaled corticosteroids and p.o. corticosteroids.

b. Chronic Obstructive Pulmonary Disease (COPD)

Tumor necrosis factor has been implicated in the pathophysiology of chronic obstructive pulmonary disease, (Keatings (2000) *Chest.* 118:971; Sakao et al.(2001) *Am J Respir Crit Care Med.* 163:420; Sakao et al. (2002) *Chest.* 122:416). The term "chronic obstructive pulmonary disease" or "COPD" as used interchangeably herein, refers to a group of lung diseases characterized by limited airflow with variable degrees of air sack enlargement and lung tissue destruction. The term COPD includes chronic bronchitis (mucous hypersecretion with goblet cell submucosal gland hyperplasia), chronic obstructive bronchitis, or emphysema (destruction of airway parenchyma), or combinations of these conditions. Emphysema and chronic bronchitis are the most common forms of chronic obstructive pulmonary disease. COPD is defined by irreversible airflow obstruction.

In COPD, chronic inflammation leads to fixed narrowing of small airways and lung parenchyma and alveolar wall destruction (emphysema). This is characterized by increased numbers of alveolar macrophages, neutrophils, and cytotoxic T lymphocytes, and the release of multiple inflammatory mediators (lipids, chemokines, cytokines, growth factors). This inflammation leads to fibrosis with a narrowing of the small airways and lung parenchymal destruction. There is also a high level of oxidative stress, which may amplify this inflammation.

G. Intestinal Disorders

Tumor necrosis factor has been implicated in the pathophysiology of inflammatory bowel disorders including Crohn's disease (see e.g., Tracy et al. (1986) *Science* 234:470; Sun et al. (1988) *J. Clin. Invest.* 81:1328; MacDonald et al. (1990) *Clin. Exp. Immunol.* 81:301). Chimeric murine anti-hTNFα antibodies have undergone clinical testing for treatment of Crohn's disease (van Dullemen et al. (1995) *Gastroenterology* 109:129). The invention includes treatment comprising administering a TNFα antibody obtained using the method of the invention to treat intestinal disorders, such as idiopathic inflammatory bowel disease, using human antibodies, or antigen-binding fragments thereof. Idiopathic inflammatory bowel disease includes two syndromes, Crohn's disease and ulcerative colitis. In one embodiment, an antibody obtained using the method of the invention is also used to treat disorders often associated with IBD and Crohn's disease. The term "inflammatory bowel disorder (IBD)-related disorder" or "Crohn's disease-related disorder," as used interchangeably herein, is used to describe conditions and complications commonly associated with IBD and Crohn's disease.

The invention includes a multiple-variable dose regimen comprising administering a TNFα antibody to treat Crohn's disease. The treatment of Crohn's disease is based on location, extent, and severity of disease. Pharmacologic interventions include anti-inflammatory agents (aminosalicylates and corticosteroids) and immunomodulatory agents (azathioprine and 6-mercaptopurine [6-MP], cyclosporine, methotrexate [MTX], antibiotic agents, and biologic agents). C-reactive protein (CRP) and erythrocyte sedimentation rate (ESR) levels reflect non-specific acute phase reactions. Endoscopy is a primary means of diagnosing Crohn's disease. Radiologic features of Crohn's disease are shown by barium examination includes mucosal edema, aphthous and linear ulcerations, asymmetrical narrowing and strictures, and separation of adjacent loops of bowel caused by mesenteric thickening. Abnormalities are focal and asymmetric. The primary histologic lesion is an aphthous ulcer. Subjects with Crohn's disease can be evaluated using the Crohn's Disease Activity Index (CDAI), which is a standard measure of the severity of the disease with higher scores indicating more severe disease activity.

Examples of Crohn's disease-related disorders which can be treated using the methods of the invention include fistulas in the bladder, vagina, and skin; bowel obstructions; abscesses; nutritional deficiencies; complications from corticosteroid use; inflammation of the joints; erythem nodosum; pyoderma gangrenosum; and lesions of the eye. Other disorders commonly associated with Crohn's disease include Crohn's-related arthralgias, fistulizing Crohn's, indeterminant colitis, and pouchitis.

H. Cardiac Disorders

An antibody, or antigen-binding fragment thereof, obtained using the method of the invention also can be used to treat in of various cardiac or coronary disorders, including ischemia of the heart (see e.g., European Patent Application Publication No. EP 453 898) and heart insufficiency (weakness of the heart muscle) (see e.g., PCT Publication No. WO 94/20139). TNFα has also been implicated in the pathophysiology of restenosis (see e.g., Clausell et al. (1994), supra; Medall et al. (1997) Heart 78:273).

As used herein, the term "a cardiac disorder in which TNFα activity is detrimental" is intended to include coronary and cardiovascular diseases in which the presence of TNFα in a subject suffering from the disorder has been shown to be or is suspected of being either responsible for the pathophysiology of the disorder or a factor that contributes to a worsening of the disorder, including cardiovascular disorders, e.g., restenosis. The term "cardiovascular disorder" or "coronary disorder" as used interchangeably herein, refers to any disease, disorder, or state involving the cardiovascular system, e.g., the heart, the blood vessels, and/or the blood. A coronary disorder is generally characterized by a narrowing of the blood vessels that supply blood and oxygen to the heart (coronary arteries). Coronary disease may result from the build up of fatty material and plaque. As the coronary arteries narrow, the flow of blood to the heart can slow or stop. Coronary disorders of the invention can apply to any abnormality of an artery, whether structural, histological, biochemical or any other abnormality. An example of coronary heart disease is restenosis. In one embodiment, a coronary disorder refers to any disease, disorder, or state involving the cardiovascular system excluding ischemia of the heart and heart insufficiency.

Coronary disorders in which TNFα activity is detrimental often result from a blockage in an artery. Such a blockage can be caused by a clot, which usually forms in a coronary artery that has been previously narrowed from changes usually related to atherosclerosis. For example, if the atherosclerotic plaque inside the arterial wall cracks, it can trigger the formation of a thrombus, or clot. Such disorders may be evidenced, for example, by an increase in the concentration of TNFα in a biological fluid of a subject suffering from the disorder (e.g., an increase in the concentration of TNFα in serum, plasma, synovial fluid, etc. of the subject), which can be detected, for example, using an anti-TNFα antibody as described above. A coronary disorder can be also caused by an imbalance in arterial pressure, a malfunction of the heart, or an occlusion of a blood vessel, e.g., by a thrombus. Coronary disorders includes both coronary artery disease and peripheral vascular disease.

There are numerous examples of cardiac disorders in which TNFα activity is detrimental, including restenosis. The use of the antibodies, antibody portions, for treatment of specific coronary disorders is discussed further below. In certain embodiments, an antibody, antibody portion, is administered to the subject in combination with another therapeutic agent, as described below.

Antibodies obtained using methods of the invention may also be used for inhibiting TNFα activity in a subject with a cardiac disorder. The invention provides methods for inhibiting or decreasing TNFα activity in a subject with a coronary disorder, comprising administering to the subject an antibody, or antibody portion, or other TNFα inhibitor of the invention such that TNFα activity in the subject is inhibited or decreased. Preferably, the TNFα is human TNFα and the subject is a human subject. Alternatively, the subject can be a mammal expressing a TNFα with which an antibody of the invention cross-reacts. Still further the subject can be a mammal into which has been introduced hTNFα (e.g., by administration of hTNFα or by expression of an hTNFα transgene). An antibody of the invention can be administered to a human subject for therapeutic purposes.

Moreover, an antibody of the invention can be administered to a non-human mammal expressing a TNFα with which the antibody cross-reacts (e.g., a primate, pig or mouse) for veterinary purposes or as an animal model of human disease. Regarding the latter, such animal models may be useful for evaluating the multiple-variable dose therapeutic efficacy (e.g., testing of dosages and time courses of administration). Commonly used animal models for studying coronary disorders, including restenosis, include the rat or mouse carotid artery ligation model and the carotid artery injury model (Ferns et al. (1991) Science 253:1129; Clowes et al. (1983) Lab. Invest. 49:208; Lindner et al. (1993) Circ Res. 73:792). In the carotid artery ligation model, arterial blood flow is disrupted by ligation of the vessel near the distal bifurnation. As described in Clowes et al., the carotid artery injury model is performed such that the common carotid artery is denuded of endothelium by the intraluminal passage of a balloon catheter introduced through the external carotid artery. At 2 weeks, the carotid artery is markedly narrowed due to smooth muscle cell constriction, but between 2 and 12 weeks the intimal doubles in thickness leading to a decrease in luminal size. Any of these models can be used to determine the potential therapeutic action of the TNFα antibodies of the invention in the prevention and treatment of restenosis in humans.

The invention includes treatment of cardiovascular disorders in which TNFα activity is detrimental, wherein inhibition of TNFα activity is expected to alleviate the symptoms and/or progression of the coronary disease or to prevent the coronary disease. Subjects suffering from or at risk of developing coronary disorders can be identified through clinical symptoms. Clinical symptoms in coronary disease often include chest pain, shortness of breath, weakness, fainting spells, alterations in consciousness, extremity pain, paroxysmal nocturnal dyspnea, transient ischemic attacks and other such phenomena experienced by the patient. Clinical signs of coronary disease can also include EKG abnormalities, altered peripheral pulses, arterial bruits, abnormal heart sounds, rates and wheezes, jugular venous distention, neurological alterations and other such findings discerned by the clinician. Coronary disorders may also be evidenced, for example, by an increase in the concentration of TNFα in a biological fluid of a subject suffering from the disorder (e.g., an increase in the concentration of TNFα in serum, plasma, synovial fluid, etc. of the subject).

Examples of a cardiovascular disorder include, but are not limited to, coronary artery disease, angina pectoris, myocardial infarction, cardiovascular tissue damage caused by cardiac arrest, cardiovascular tissue damage caused by cardiac bypass, cardiogenic shock, and hypertension, atherosclerosis, coronary artery spasm, coronary artery disease, valvular disease, arrhythmias, and cardiomyopathies. The use of the antibodies, antibody portions, for treatment of specific cardiovascular diseases are discussed further below. In certain embodiments, the antibody, antibody portion, is administered to the subject in combination with another therapeutic agent, as described below.

1. Restenosis

The term "restenosis" as used herein refers to the recurrence of stenosis, which is the narrowing or constriction of an artery. Restenosis often occurs as a preocclusive lesion that develops following a reconstructive procedure in a diseased blood vessel. The term is not only applied to the recurrence of a pre-existing stenosis, but also to previously normal vessels that become partially occluded following vascular bypass. In another embodiment, the invention provides a method of treating restenosis comprising administering the antibody, or antigen binding portion thereof, obtained using the invention to a subject who has or is at risk of developing restenosis.

TNFα has been implicated in the pathophysiology of restenosis (see Zhou et al. (2002) Atherosclerosis. 161:153; Javed et al. (2002) Exp and Mol Pathol 73:104). For example, in the murine wire carotid model, TNF −/− mice demonstrated a seven-fold reduction in initial hyperplasia compared to wild type mice (Zimmerman et al. (2002) Am J Phsiol Regul Integr Comp Physiol 283:R505). Restenosis can occur as the result of any type of vascular reconstruction, whether in the coronary vasculature or in the periphery (Colburn and Moore (1998) Myointimal Hyperplasia pp. 690-709 in Vascular Surgery: A Comprehensive Review Philadelphia: Saunders). For example, studies have reported symptomatic restenosis rates of 30-50% following coronary angioplasties (see Berk and Harris (1995) Adv. Intern. Med. 40:455). After carotid endarterectomies, as a further example, 20% of patients studied had a luminal narrowing greater than 50% (Clagett et al. (1986) J. Vasc. Surg. 3:10). Restenosis is evidenced in different degrees of symptomatology which accompany preocclusive lesions in different anatomical locations, due to a combination of factors including the nature of the vessels involved, the extent of residual disease, and local hemodynamics.

"Stenosis," as used herein refers to a narrowing of an artery as seen in occlusive disorder or in restenosis. Stenosis can be accompanied by those symptoms reflecting a decrease in blood flow past the narrowed arterial segment, in which case the disorder giving rise to the stenosis is termed a disease (i.e., occlusive disease or restenosis disease). Stenosis can exist asymptomatically in a vessel, to be detected only by a diagnostic intervention such as an angiography or a vascular lab study.

The antibodies obtained using the method of the invention may be used to treat a subject suffering from or at risk of developing restenosis. A subject at risk of developing restenosis includes a subject who has undergone PTCA. The subject may have also had a stent inserted to prevent restenosis. The TNFα antibody can be used alone or in combination with a stent to prevent the re-occurrence of stenosis in a subject suffering from cardiovascular disease.

2. Congestive Heart Failure

TNFα has been implicated in the pathophysiology of congestive heart failure (see Zhou et al. (2002) Atherosclerosis 161:153). Serum levels of TNFα are elevated in patients with congestive heart failure in a manner which is directly proportional to the severity of the disease (Levine et al. (1990) N Engl J Med 323:236; Torre-Amione et al. (1996) J Am Coll Cardiol 27:1201). In addition, inhibitors of TNFα have also been shown to improve congestive heart failure symptoms (Chung et al. (2003) Circulation 107:3133).

As used herein, the term "congestive heart failure" includes a condition characterized by a diminished capacity of the heart to supply the oxygen demands of the body. Symptoms and signs of congestive heart failure include diminished blood flow to the various tissues of the body, accumulation of excess blood in the various organs, e.g., when the heart is unable to pump out the blood returned to it by the great veins, exertional dyspnea, fatigue, and/or peripheral edema, e.g., peripheral edema resulting from left ventricular dysfunction. Congestive heart failure may be acute or chronic. The manifestation of congestive heart failure usually occurs secondary to a variety of cardiac or systemic disorders that share a temporal or permanent loss of cardiac function. Examples of such disorders include hypertension, coronary artery disease, valvular disease, and cardiomyopathies, e.g., hypertrophic, dilative, or restrictive cardiomyopathies.

A "subject who has or is suffering from congestive heart failure" is a subject who has a disorder involving a clinical syndrome of diverse etiologies linked by the common denominator of impaired heart pumping in which the heart cannot pump blood commensurate with the requirements of the metabolizing tissues, or can do so only from an elevated filling pressure. A "subject at risk of developing congestive heart failure" is a subject who has a propensity of developing congestive heart failure because of certain factors affecting the cardiovascular system of the subject. It is desirable to reduce the risk of or prevent the development of congestive heart failure in these subjects. The phrase "with congestive heart failure" includes patients who are at risk of suffering from this condition relative to the general population, even though they may not have suffered from it yet, by virtue of exhibiting risk factors. For example, a patient with untreated hypertension may not have suffered from congestive heart failure, but is at risk because of his or her hypertensive condition. In one embodiment of the invention, the antibody adalimumab is used to treat a subject at risk of developing congestive heart failure.

3. Acute Coronary Syndromes

TNFα has been implicated in the pathophysiology of acute coronary syndromes (see Libby (1995) Circulation 91:2844). Acute coronary syndromes include those disorders wherein the subject experiences pain due to a blood flow restriction resulting in not enough oxygen reaching the heart. Studies have found that TNFα plays a role in acute coronary syndromes. For example, in a novel rat heterotropic cardiac transplantation-coronary ligation model capable of inducing myocardial infarction in the absence of downstream hemodynamic effects, administration of chimeric soluble TNF receptor (sTNFR) abolished transient LV remodeling and dysfunction (Nakamura, et al. (2003) J. Cardiol. 41:41). It was also found that direct injection of an sTNFR expression plasmid to the myocardium, resulted in a reduction in the infarction size in acute myocardial infarction (AMI) experimental rats (Sugano et al. (2002) *FASEB J* 16:1421).

In one embodiment, a TNFα antibody is used for the treatment or prevention of an acute coronary syndrome in a subject, wherein the acute coronary syndrome is a myocardial infarction or angina.

As used herein, the term "myocardial infarction" or "MI" refers to a heart attack. A myocardial infarction involves the necrosis or permanent damage of a region of the heart due to an inadequate supply of oxygen to that area. This necrosis is typically caused by an obstruction in a coronary artery from either atherosclerosis or an embolis. MIs which are treated by the TNFα antibody obtained using the methods of the invention include both Q-wave and non-Q-wave myocardial infarction. Most heart attacks are caused by a clot that blocks one of the coronary arteries (the blood vessels that bring blood and oxygen to the heart muscle). For example, a clot in the coronary artery interrupts the flow of blood and oxygen to the heart muscle, leading to the death of heart cells in that area. The damaged heart muscle permanently loses its ability to contract, and the remaining heart muscle needs to compensate for it. An MI can also be caused by overwhelming stress in the individual.

The term "angina" refers to spasmodic, choking, or suffocative pain, and especially as denoting angina pectoris which is a paroxysmal thoracic pain due, most often, to anoxia of the myocardium. Angina includes both variant angina and exertional angina. A subject having angina has ischemic heart disease which is manifested by sudden, severe, pressing substemal pain that often radiates to the left shoulder and along the left arm. TNFα has been implicated in angina, as TNFα levels are upregulated in patients with both MI and stable angina (Balbay et al. (2001) *Angiology* 52109).

4. Artherosclerosis

"Atherosclerosis" as used herein refers to a condition in which fatty material is deposited along the walls of arteries. This fatty material thickens, hardens, and may eventually block the arteries. Atherosclerosis is also referred to arteriosclerosis, hardening of the arteries, and arterial plaque buildup. Polyclonal antibodies directed against TNFα have been shown to be effective at neutralizing TNFα activity resulting in inflammation and restenosis in the rabbit atherosclerotic model (Zhou et al., supra). Accordingly, a TNFα antibody may be used to treat or prevent subjects afflicted with or at risk of having atherosclerosis.

5. Cardiomyopathy

The term "cardiomyopathy" as used herein is used to define diseases of the myocardium wherein the heart muscle or myocardium is weakened, usually resulting in inadequate heart pumping. Cardiomyopathy can be caused by viral infections, heart attacks, alcoholism, long-term, severe hypertension (high blood pressure), or by autoimmune causes.

In approximately 75-80% of heart failure patients coronary artery disease is the underlying cause of the cardiomyopathy and is designated "ischemic cardiomyopathy." Ischemic cardiomyopathy is caused by heart attacks, which leave scars in the heart muscle or myocardium. The affected myocardium is then unable to contribute to the heart pumping function. The larger the scars or the more numerous the heart attacks, the higher the chance there is of developing ischemic cardiomyopathy.

Cardiomyopathies that are not attributed to underlying coronary artery disease, and are designated "non-ischemic cardiomyopathies." Non-ischemic cardiomyopathies include, but are not limited to idiopathic cardiomyopathy, hypertrophic cardiomyopathy, alcoholic cardiomyopathy, dilated cardiomyopathy, peripartum cardiomyopathy, and restrictive cardiomyopathy.

I. Spondyloarthropathies

TNFα has been implicated in the pathophysiology of a wide variety of disorders, including inflammatory diseases such as spondyloarthopathies (see e.g., Moeller et al. (1990) *Cytokine* 2:162; U.S. Pat. No. 5,231,024; European Patent Publication No. 260 610). The invention provides multiple-variable dose methods for inhibiting TNFα activity in a subject suffering from a spondyloarthropathy, which method comprises administering to the subject an antibody, antibody portion, such that TNFα activity in the subject suffering from a spondyloarthropathy is inhibited.

As used herein, the term "spondyloarthropathy" or "spondyloarthropathies" is used to refer to any one of several diseases affecting the joints of the spine, wherein such diseases share common clinical, radiological, and histological features. A number of spondyloarthropathies share genetic characteristics, i.e. they are associated with the HLA-B27 allele. In one embodiment, the term spondyloarthropathy is used to refer to any one of several diseases affecting the joints of the spine, excluding ankylosing spondylitis, wherein such diseases share common clinical, radiological, and histological features. Examples of spondyloarthropathies include ankylosing spondylitis, psoriatic arthritis/spondylitis, enteropathic arthritis, reactive arthritis or Reiter's syndrome, and undifferentiated spondyloarthropathies. Examples of animal models used to study spondyloarthropathies include ank/ank transgenic mice, HLA-B27 transgenic rats (see Taurog et al. (1998) *The Spondylarthritides*. Oxford:Oxford University Press).

The multiple-variable dose methods of the invention can also be used to treat subjects who are at risk of developing a spondyloarthropathy using multiple-variable dose methods. Examples of subjects who are at risk of having spondyloarthropathies include humans suffering from arthritis. Spondyloarthropathies can be associated with other forms of arthritis, including rheumatoid arthritis. In one embodiment of the invention, antibodies are used in multiple-variable dose methods to treat a subject who suffers from a spondyloarthropathy associated with rheumatoid arthritis. Examples of spondyloarthropathies which can be treated with a TNFα antibody are described below:

1. Ankylosing Spondylitis (AS)

Tumor necrosis factor has been implicated in the pathophysiology of ankylosing spondylitis (see Verjans et al. (1991) *Arthritis Rheum.* 34:486; Verjans et al. (1994) *Clin Exp Immunol.* 97:45; Kaijtzel et al. (1999) *Hum Immunol.* 60:140). Ankylosing spondylitis (AS) is an inflammatory disorder involving inflammation of one or more vertebrae. AS is a chronic inflammatory disease that affects the axial skeleton and/or peripheral joints, including joints between the vertebrae of the spine and sacroiliac joints and the joints between the spine and the pelvis. AS can eventually cause the affected vertebrae to fuse or grow together. Spondyarthropathies, including AS, can be associated with psoriatic arthritis (PsA) and/or inflammatory bowel disease (IBD), including ulcerative colitis and Crohn's disease.

Early manifestations of AS can be determined by radiographic tests, including CT scans and MRI scans. Early manifestations of AS often include scroiliitis and changes in the sacroliac joints as evidenced by the blurring of the cortical margins of the subchrondral bone, followed by erosions and sclerosis. Fatigue has also been noted as a common symptom of AS (Duffy et al. (2002) *ACR 66th Annual Scientific Meeting* Abstract). Accordingly, multiple-variable dose methods comprising administering an antibody, or antigen-binding fragment thereof, of the invention can be used to treat AS.

In one embodiment, the multiple-variable dose method of the invention is used to treat a spondyloarthropathy associated with IBD, including AS. AS is often treated with non-steroidal anti-inflammatory medications (NSAIDs), such as aspirin or indomethacin. Accordingly, a TNFα antibody used in the multiple-variable dose method of the invention may also be administered in combination with agents commonly used to reduce inflammation and pain commonly associated with ankylosing spondylitis.

2. Psoriatic Arthritis

Tumor necrosis factor has been implicated in the pathophysiology of psoriatic arthritis (PsA) (Partsch et al. (1998) *Ann Rheum Dis.* 57:691; Ritchlin et al. (1998) *J Rheumatol.* 25:1544). As referred to herein, psoriatic arthritis or psoriasis associated with the skin, refers to chronic inflammatory arthritis which is associated with psoriasis, which is a common chronic skin condition that causes red patches on the body. About 1 in 20 individuals with psoriasis will develop arthritis along with the skin condition, and in about 75% of cases, psoriasis precedes the arthritis. PsA exhibits itself in a variety of ways, ranging from mild to severe arthritis, wherein the arthritis usually affects the fingers and the spine. When the spine is affected, the symptoms are similar to those of ankylosing spondylitis, as described above. The TNFα antibody, or antigen-binding fragment thereof, obtained using the invention can be used for treatment of PsA.

PsA is sometimes associated with arthritis mutilans. Arthritis mutilans refers to a disorder which is characterized by excessive bone erosion resulting in a gross, erosive deformity which mutilates the joint. In one embodiment, antibodies obtained using the method of the invention are used to treat arthritis mutilans.

3. Reactive Arthritis/Reiter's Syndrome

Tumor necrosis factor has been implicated in the pathophysiology of reactive arthritis, which is also referred to as Reiter's syndrome (Braun et al. (1999) *Arthritis Rheum.* 42(10):2039). Reactive arthritis (ReA) refers to arthritis which complicates an infection elsewhere in the body, often following enteric or urogenital infections. ReA is often characterized by certain clinical symptoms, including inflammation of the joints (arthritis), urethritis, conjunctivitis, and lesions of the skin and mucous membranes. In addition, ReA can occurs following infection with a sexually transmitted disease or dysenteric infection, including chlamydia, *campylobacter, salmonella,* or *yersinia.* Accordingly, antibodies obtained using the method of the invention may be used to treat ReA.

4. Undifferentiated Spondyloarthropathies

In one embodiment, antibodies obtained using methods of the invention are used to treat subjects suffering from undifferentiated spondyloarthropathies (see Zeidler et al. (1992) *Rheum Dis Clin North Am.* 18:187). Other terms used to describe undifferentiated spondyloarthropathies include seronegative oligoarthritis and undifferentiated oligoarthritis. Undifferentiated spondyloarthropathies, as used herein, refers to a disorder wherein the subject demonstrates only some of the symptoms associated with a spondyloarthropathy. This condition is usually observed in young adults who do not have IBD, psoriasis, or the classic symptoms of AS or Reiter's syndrome. In some instances, undifferentiated spondyloarthropathies may be an early indication of AS. In one embodiment, the invention comprises administering a TNFα antibody, or antigen-binding fragment thereof, obtained using the claimed process to treat undifferentiated spondyloarthropathies.

J. Metabolic Disorders

TNFα has been implicated in the pathophysiology of a wide variety of disorders, including metabolic disorders, such as diabetes and obesity (Spiegelman and Hotamisligil (1993) *Cell* 73:625; Chu et al. (2000) *Int J Obes Relat Metab Disord.* 24:1085; Ishii et al. (2000) *Metabolism.* 49:1616). The term "metabolic disorder," as used herein, refers to diseases or disorders which affect how the body processes substances needed to carry out physiological functions. Examples of metabolic disorders include, but are not limited to, diabetes and obesity. In one embodiment of the invention, the term "metabolic disorder" is used to refer to disorders which affect how the body processes substances needed to carry out physiological functions, excluding autoimmune diabetes.

The invention provides methods for inhibiting TNFα activity in a subject suffering from such a metabolic disorder, which method comprises administering to the subject an antibody, antibody portion, such that TNFα activity in the subject suffering from a metabolic disorder is inhibited. TNFα antibodies can also be used to treat subjects who are at risk of developing a metabolic disorder.

Metabolic disorders are often associated with arthritis, including rheumatoid arthritis. In one embodiment, a TNFα inhibitor, such as an antibody, is used in a multiple-variable dose regimen in a subject who suffers from a metabolic disorder associated with rheumatoid arthritis. In another embodiment, the invention comprises administering a TNFα antibody to treat disorders associated with diabetes or obesity.

Examples of animal models for evaluating the efficacy of a TNFα antibody for the treatment of a metabolic disorder include NOD transgenic mice, Akita mice, NSY transgenic mice and ob/ob mice (see Baeder et al. (1992) *Clin Exp Immunol.* 89:174; Haseyama et al. (2002) *Tohoku J Exp Med.* 198:233; Makino et al. (1980): *Exp.Anim.* 29:1; Kolb (1987) *Diabetes/Metabolism Reviews* 3:751; Hamada et al. (2001) *Metabolism.* 50:1282; Coleman, (1978) *Diabetologia,* 14:141; Bailey et al. (1982) *Int. J. Obesity* 6:11). Examples of animal models used to study vasculitis includes the mouse HSV model (Behcet's disease), the mouse *L. casei* model (Kawasaki's disease), and the mouse ANCA model (Kawasaki's disease). Other models of vasculitis include the McH5-lpr/lpr strain (Nose et al. (1996) *Am. J. Path.* 149:1763) and the SCG/Kj strain of mice (Kinjoh et al. (1993) *Proc. Natl. Acad. Sci., USA* 90:3413). These mice strains spontaneously develop crescentic glomerulonephritis and necrotizing vasculitis of the small arteries and arterioles of the spleen, stomach, heart, uterus and ovaries. These animals develop hypergammaglobulinemia and ANCA autoantibodies that react with myeloperoxidase (MPO). Additionally, immunization of rats with human MPO results in ANCA-associated necrotizing crescentic glomerulonephritis (Brouwer et al. (1993) *J. Exp. Med.* 177:905).

Metabolic disorders affect how the body processes substances needed to carry out physiological functions. A number of metabolic disorders of the invention share certain characteristics, i.e. they are associated the insulin resistance, lack of ability to regulate blood sugar, weight gain, and increase in body mass index. Examples of metabolic disorders include diabetes and obesity. Examples of diabetes include type 1 diabetes mellitus, type 2 diabetes mellitus, diabetic neuropathy, peripheral neuropathy, diabetic retinopathy, diabetic ulcerations, retinopathy ulcerations, diabetic macrovasculopathy, and obesity. Examples of metabolic disorders which can be treated using multiple-variable dose methods comprising administration of a TNFα antibody are described in more detail below:

1. Diabetes

Tumor necrosis factor has been implicated in the pathophysiology of diabetes. (see e.g., Navarro et al . (2003) *Am J Kidney Dis.* 42:53; Daimon et al. (2003) *Diabetes Care.* 26:2015; Zhang et al. (1999) *J Tongji Med Univ.* 19:203; Barbieri et al. (2003) *Am J Hypertens.* 16:537) For example, TNFα is implicated in the pathophysiology for insulin resistance. It has been found that serum TNF levels in patients with gastrointestinal cancer correlates with insulin resistance (see e.g., McCall et al. (1992) *Br. J. Surg.* 79:1361).

The term "diabetes" or "diabetic disorder" or "diabetes mellitus," as used interchangeably herein, refers to a disease which is marked by elevated levels of sugar (glucose) in the blood. Diabetes can be caused by too little insulin (a chemical produced by the pancreas to regulate blood sugar), resistance to insulin, or both. Diabetes includes the two most common types of the disorder, namely type I diabetes and type II diabetes, which both result from the body's inability to regulate insulin. Insulin is a hormone released by the pancreas in response to increased levels of blood sugar (glucose) in the blood.

The term "type 1 diabetes," as used herein, refers to a chronic disease that occurs when the pancreas produces too little insulin to regulate blood sugar levels appropriately. Type 1 diabetes is also referred to as insulin-dependent diabetes mellitus, IDMM, juvenile onset diabetes, and diabetes—type I. Type 1 diabetes represents is the result of a progressive autoimmune destruction of the pancreatic β-cells with subsequent insulin deficiency.

The term "type 2 diabetes," refers to a chronic disease that occurs when the pancreas does not make enough insulin to keep blood glucose levels normal, often because the body does not respond well to the insulin. Type 2 diabetes is also referred to as noninsulin-dependent diabetes mellitus, NDDM, and diabetes—type II Diabetes is can be diagnosed by the administration of a glucose tolerance test. Clinically, diabetes is often divided into several basic categories. Primary examples of these categories include, autoimmune diabetes mellitus, non-insulin-dependent diabetes mellitus (type 1 NDDM), insulin-dependant diabetes mellitus (type 2 IDDM), non-autoimmune diabetes mellitus, non-insulin-dependant diabetes mellitus (type 2 NIDDM), and maturity-onset diabetes of the young (MODY). A further category, often referred to as secondary, refers to diabetes brought about by some identifiable condition which causes or allows a diabetic syndrome to develop. Examples of secondary categories include, diabetes caused by pancreatic disease, hormonal abnormalities, drug- or chemical-induced diabetes, diabetes caused by insulin receptor abnormalities, diabetes associated with genetic syndromes, and diabetes of other causes. (see e.g., Harrison's (1996) 14th ed., New York, McGraw-Hill).

Diabetes is often treated with diet, insulin dosages, and various medications described herein. Accordingly, a TNFα antibody may also be administered in combination with agents commonly used to treat metabolic disorders and pain commonly associated with diabetes.

In addition, the phrase "disorders associated with diabetes," as used herein, refers to conditions and other diseases which are commonly associated with or related to diabetes. Example of disorders associated with diabetes include, for example, hyperglycemia, hyperinsulinaemia, hyperlipidaemia, insulin resistance, impaired glucose metabolism, obesity, diabetic retinopathy, macular degeneration, cataracts, diabetic nephropathy, glomerulosclerosis, diabetic neuropathy, erectile dysfunction, premenstrual syndrome, vascular restenosis, ulcerative colitis, coronary heart disease, hypertension, angina pectoris, myocardial infarction, stroke, skin and connective tissue disorders, foot ulcerations, metabolic acidosis, arthritis, and osteoporosis.

Diabetes manifests itself in the foregoing categories and can cause several complications that are discussed in the following sections. Accordingly, the antibody, or antigen-binding fragment thereof, of the invention can be used to treat diabetes. In one embodiment, a TNFα antibody, or antigen-binding fragment thereof, is used to treat diabetes associated with the above identified catagories. In another embodiment, the invention includes administering a TNFα antibody to treat disorders associated with diabetes. Diabetes manifests itself in many complications and conditions associated with diabetes, including the following catagories:

a. Diabetic Neuropathy and Peripheral Neuropathy

Tumor necrosis factor has been implicated in the pathophysiology of diabetic neuropathy and peripheral neuropathy. (See Benjafield et al. (2001) *Diabetes Care.* 24:753; Qiang et al. (1998) *Diabetologia.*41:1321; Pfeiffer et al. (1997) *Horm Metab Res.* 29:111).

The term "neuropathy," also referred to as nerve damage-diabetic, as used herein, refers to a common complication of diabetes in which nerves are damaged as a result of hyperglycemia (high blood sugar levels). A variety of diabetic neuropathies are recognized, such as distal sensorimotror polyneuropathy, focal motor neuropathy, and autonomic neuropathy.

The term "peripheral neuropathy," also known as peripheral neuritis and diabetic neuropathy, as used herein, refers to the failure of the nerves to carry information to and from the brain and spinal cord. Peripheral neuropathy produces symptoms such as pain, loss of sensation, and the inability to control muscles. In some cases, the failure of nerves to control blood vessels, intestinal function, and other organs results in abnormal blood pressure, digestion, and loss of other basic involuntary processes. Peripheral neuropathy may involve damage to a single nerve or nerve group (mononeuropathy) or may affect multiple nerves (polyneuropathy).

Neuropathies that affect small myelinated and unmyelinated fibers of the sympathetic and parasympathetic nerves are known as "peripheral neuropathies." Furthermore, the related disorder of peripheral neuropathy, also known as peripheral neuritis and diabetic neuropathy, refers to the failure of the nerves to carry information to and from the brain and spinal cord. This produces symptoms such as pain, loss of sensation, and the inability to control muscles. In some cases, failure of nerves controlling blood vessels, intestinal function, and other organs results in abnormal blood pressure, digestion, and loss of other basic involuntary processes. Peripheral neuropathy may involve damage to a single nerve or nerve group (mononeuropathy) or may affect multiple nerves (polyneuropathy).

The term "diabetic neuropathy" refers to a common complication of diabetes in which nerves are damaged as a result of hyperglycemia (high blood sugar levels). Diabetic neuropathy is also referred to as neuropathy and nerve damage-diabetic. A variety of diabetic neuropathies are recognized, such as distal sensorimotror polyneuropathy, focal motor neuropathy, and autonomic neuropathy.

b. Diabetic Retinopathy

Tumor necrosis factor has been implicated in the pathophysiology of diabetic retinopthy (Scholz et al. (2003) *Trends Microbiol.* 11:171). The term "diabetic retinopathy" as used herein, refers to progressive damage to the eye's retina caused by long-term diabetes. Diabetic retinopathy, includes proliferative retinopathy. Proliferative neuropathy in turn includes includes neovascularization, pertinal hemmorrhave and retinal detachement.

In advanced retinopathy, small vessels proliferate on the surface of the retina. These blood vessels are fragile, tend to bleed and can cause peretinal hemorrhages. The hemorrhage can obscure vision, and as the hemorrhage is resorbed fibrous tissue forms predisposing to retinal detachments and loss of vision. In addition, diabetic retinopathy includes prolferative retinopathy which includes neovascularization, pertinal hemmorrhave and retinal detachement. Daibetic retinopathy also includes "background retinopathy" which involves changes occuring with the layers of the retina.

c. Diabetic Ulcerations and Retinopathy Ulcerations

Tumor necrosis factor has been implicated in the pathophysiology of diabetic ulcerations, (see Lee et al. (2003) *Hum Immunol.* 64:614; Navarro et al. (2003) *Am J Kidney Dis.* 42:53; Daimon et al (2003) *Diabetes Care.* 26:2015; Zhang et al. (1999) *J Tongji Med Univ.* 19:203; Barbieri et al. (2003) *Am J Hypertens.* 16:537; Venn et al. (1993) *Arthritis Rheum.* 36:819; Westacott et al. (1994) *J Rheumatol.* 21:1710).

The term "diabetic ulcerations," as used herein, refers to an ulcer which results as a complication of diabetes. An ulcer is a crater-like lesion on the skin or mucous membrane caused by an inflammatory, infectious, malignant condition, or metabolic disorder. Typically diabetic ulcers can be found on limbs and extremeties, more typically the feet. These ulcers, caused by diabetic conditions, such as neuropathy and a vacualr insuffciency, can lead to ischemia and poor wound healing. More extensive ulcerations may progress to ostemyelitis. Once ostemyelitis develops, it may be dificult to eradicate with antibotics alone and amputation maybe necessary.

The term "retinopathy ulcerations," as used herein refers to an ulcer which causes or results in damages to the eye and the eye's retina. Retinopathy ulcerations may include conditions such has retinoathic hemmorages.

d. Diabetic Macrovasculopathy

Tumor necrosis factor has been implicated in the pathophysiology of diabetic macrovasculopathy (Devaraj et al. (2000) *Circulation.* 102:191; Hattori et al. (2000) *Cardiovasc Res.* 46:188; Clausell et al. (1999) *Cardiovasc Pathol.* 8:145). The term "diabetic macrovasculopathy," also referred to as "macrovascular disease," as used herein, refers to a disease of the blood vessels that results from diabetes. Diabetic macrovasculopathy complication occurs when, for example, fat and blood clots build up in the large blood vessels and stick to the vessel walls. Diabetic macrovasculopathies include diseases such as coronary disease, cerebrovascular disease, and peripheral vascular disease, hyperglycaemia and cardiovascular disease, and strokes.

2. Obesity

Tumor necrosis factor has been implicated in the pathophysiology of obesity (see e.g., Pihlajamaki J et al. (2003) *Obes Res.* 11:912; Barbieri et al. (2003) *Am J Hypertens.* 16:537; Tsuda et al. (2003) *J Nutr.* 133:2125). The term "obesity" as used herein, refers to a condition in which the subject has an excess of body fat relative to lean body mass. In one embodiment, obesity refers to a condition in which an individual weighs at least about 20% or more over the maximum desirable for their height. When an adult is more than 100 pounds overweight, he or she is considered to be "morbidly obese." In another embodiment, obesity is defined as a BMI (body mass index) over 30 kg/m2. Obesity increases a person's risk of illness and death due to diabetes, stroke, coronary artery disease, hypertension, high cholesterol, and kidney and gallbladder disorders. Obesity may also increase the risk for some types of cancer, and may be a risk factor for the development of osteoarthritis and sleep apnea.

K. Anemia

TNFα has been implicated in the pathophysiology of a wide variety of anemias (see e.g., Jongen-Lavrencic et al. (1997) *J. Rheumatol.* 24:1504; Demeter et al. (2002) *Ann Hematol.* 81:566; DiCato (2003) *The Oncologist* 8 (suppl 1):19). The invention provides a method for inhibiting TNFα activity in a subject suffering from anemia, which method comprises administering to the subject an antibody, antibody portion, such that TNFα activity in the subject suffering from anemia is inhibited. In one embodiment, the anemia is associated with rheumatoid arthritis.

The term "anemia" as used herein, refers to an abnormally low number of circulating red cells or a decreased concentration of hemoglobin in the blood. Examples of anemia related to rheumatoid arthritis include, for example, anemia of chronic disease, iron deficiency anemia, and autoimmune hemolytic anemia. In one embodiment, the invention provides a method of treating anemias related to, for example, anemias related to rheumatoid arthritis, anemias of infection and chronic inflammatory diseases, iron deficiency anemia, autoimmune hemolytic anemia, myelophthisic anemia, aplastic anemia, hypoplastic anemia, pure red cell aplasia and anemia associated with renal failure or endocrine disorders, megaloblastic anemias, defects in heme or globin synthesis, anemia caused by a structural defect in red blood cells, e.g., sickle-cell anemia, and anemias of unknown origins such as sideroblastic anemia, anemia associated with chronic infections such as malaria, trypanosomiasis, HIV, hepatitis virus or other viruses, and myelophthisic anemias caused by marrow deficiencies.

Examples of animal models used to study anemia include rats inoculated with peptidolglycan-polysaccharide polymers (see Coccia et al., (2001) *Exp Hematology.* 29:1201-1209). Examples of animal models used to study pain are well known in the art, and include the rat sciatic nerve ligation model, and the rat segmental spinal nerve ligation model (see Bennett and Zie, (1988) *Pain.* 33:87-107; Kim and Chung, (1992) *Pain* 50:355-363).

L. Pain

TNFα has been implicated in the pathophysiology of a wide variety of pain syndromes (see e.g., Sorkin et al. (1997) *Neuroscience.* 81:255; Huygen et al. (2002) *Mediators Inflamm.* 11:47; Parada et al. (2003) *Eur J Neurosci.* 17:1847). The term "pain" as used herein, refers to all types of pain. The term shall refer to acute and chronic pains, such as neuropathic pain and post-operative pain, chronic lower back pain, cluster headaches, herpes neuralgia, phantom limb pain, central pain, dental pain, opioid-resistant pain, visceral pain, surgical pain, bone injury pain, pain during labor and delivery, pain resulting from burns, including sunburn, post partum pain, migraine, angina pain, and genitourinary tract-related pain including cystitis. The term also includes nociceptive pain or nociception.

The invention provides methods for inhibiting TNFα activity in a subject suffering from such a pain disorder, which method comprises administering to the subject an antibody, antibody portion, such that TNFα activity in the subject suffering from pain is inhibited. Pain has been defined in a variety of ways, including nociceptive pain and neuropathic pain. The most commonly experienced form of pain may be defined as the effect of a stimulus on nerve endings, which results in the transmission of impulses to the cerebrum. Pain is also commonly associated with inflammatory disorders, including, for example, rheumatoid arthritis. In one embodiment, the antibody of the invention is used to treat a subject who suffers from pain associated with rheumatoid arthritis.

Examples of pain disorders in which TNFα activity is detrimental are discussed further below.

1. Neuropathic Pain

Tumor necrosis factor has been implicated in the pathophysiology of neuropathic pain (see Sommer (1999) *Schmerz*. 13:315; Empl et al., (2001) *Neurology*. 56:1371; Schafers et al. (2003) *J Neurosci*. 23:3028). As used herein the term "neuropathic pain" refers to pain that results from injury to a nerve, spinal cord, or brain, and often involves neural supersensitivity. Examples of neuropathic pain include chronic lower back pain, pain associated with arthritis, cancer-associated pain, herpes neuralgia, phantom limb pain, central pain, opioid resistant neuropathic pain, bone injury pain, and pain during labor and delivery. Other examples of neuropathic pain include post-operative pain, cluster headaches, dental pain, surgical pain, pain resulting from severe, for example third degree, burns, post partum pain, angina pain, genitourinary tract related pain, and including cystitis.

Neuropathic pain is distinguished from nociceptive pain. Pain involving a nociceptive mechanism usually is limited in duration to the period of tissue repair and generally is alleviated by available analgesic agents or opioids (Myers (1995) *Regional Anesthesia* 20:173). Neuropathic pain typically is long-lasting or chronic and often develops days or months following an initial acute tissue injury. Neuropathic pain can involve persistent, spontaneous pain as well as allodynia, which is a painful response to a stimulus that normally is not painful. Neuropathic pain also can be characterized by hyperalgesia, in which there is an accentuated response to a painful stimulus that usually is trivial, such as a pin prick. Unlike nociceptive pain, neuropathic pain generally is resistant to opioid therapy (Myers, supra, 1995). Accordingly, antibodies obtained using methods of the invention can be used to treat neuropathic pain.

2. Nociceptive Pain

As used herein the term "nociceptive pain" refers to pain that is transmitted across intact neuronal pathways, i.e., pain caused by injury to the body. Nociceptive pain includes somatic sensation and normal function of pain, and informs the subject of impending tissue damage. The nociceptive pathway exists for protection of the subject, e.g., the pain experienced in response to a burn). Nociceptive pain includes bone pain, visceral pain, and pain associated with soft tissue.

Tumor necrosis factor has been implicated in the pathophysiology of visceral pain (see Coelho et al. (2000) *Am J Physiol Gastrointest Liver Physiol*. 279:G781; Coelho et al. (2000) *Brain Res Bull*. 52:223). Visceral pain is used to refer to nociceptive pain that is mediated by receptors on A-delta and C nerve fibers. A-delta and C-nerve fibers are which are located in skin, bone, connective tissue, muscle and viscera. Visceral pain can be vague in distribution, spasmodic in nature and is usually described as deep, aching, squeezing and colicky in nature. Examples of visceral pain include pain associated with a heart attack, wherein the visceral pain can be felt in the arm, neck and/or back, and liver capsule pain, wherein the visceral pain can be felt in the back and/or right shoulder. Accordingly, antibodies obtained using the invention can be used to treat visceral pain.

M. Hepatic Disorders

TNFα has been implicated in the pathophysiology of a wide variety of hepatic disorders (see e.g., Colletti et al. (1990) *J Clin Invest*. 85:1936; Tiegs (1997) *Acta Gastroenterol Belg*. 60:176; Fernandez et al. (2000) *J Endotoxin Res*. 6:321). The invention provides methods for inhibiting TNFα activity in a subject suffering from such a hepatic disorder.

As used herein, the term "a hepatic disorder in which TNFα activity is detrimental" is intended to include diseases and other disorders of the liver or conditions associated with hepatocellular injury or a biliary tract disorders in which the presence of TNFα in a subject suffering from the disorder has been shown to be or is suspected of being either responsible for the pathophysiology of the disorder or a factor that contributes to a worsening of the disorder. Accordingly, a hepatic disorder in which TNFα activity is detrimental is a disorder in which inhibition of TNFα activity is expected to alleviate the symptoms and/or progression of the hepatic disorder. In one embodiment, hepatic disorders refers to a human liver disease or condition associated with hepatocellular injury or a biliary tract disorder excluding hepatitis, alcoholic hepatitis, and viral hepatitis.

Examples of animal models used for evaluating the therapeutic efficacy of an agent for treating a hepatic disorder using multiple-variable dose methods include the chimpanzee hepatitis C virus model (see Shimizu et al. (1990) *Proc Natl Acad Sci. USA* 87:6441). Examples of animal models used to study skin and nail disorder disorders include, for example, the severe combined immunodeficient (SCID) mouse model (psoriasis) and the Smith line (SL) chicken and depigmenting mouse (vitiligo) (see Nickoloff (2000) *Investig Dermatol Symp Proc*. 5:67; Austin et al. (1995) *Am J Pathol*. 146:1529; Lerner et al. (1986) *J Invest Dermatol*. 87:299).

Hepatic disorders include many diseases and disorders wherein the liver functions improperly or ceases to function. Hepatocellular injuries can include alcoholic cirrhosis, cd antitypsin deficiency, autoimmune cirrhosis, cryptogenic cirrhosis, fulminant hepatitis, hepatitis B and C, and steatohepatitis. Examples of biliary tract disorders include cystic fibrosis, primary biliary cirrhosis, sclerosing cholangitis and biliary obstruction (Wiesner (1996) "Current Indications, Contra Indications and Timing for Liver Transplantation" in *Transplantation of the Liver*, Saunders (publ.); Busuttil and Klintmalm (eds.) Chapter 6; Klein (1998) Partial Hypertension: The Role of Liver Transplantation, Musby (publ.) in *Current Surgical Therapy* 6.sup.th Ed. Cameron, J. (ed).

The term "hepatitis" refers to inflammation of the liver. Hepatitis can be caused by infections with various organisms, including bacteria, viruses (Hepatitis A, B, C, etc.), or parasites. Chemical toxins such as alcohol, drugs, or poisonous mushrooms can also damage the liver and cause it to become inflamed. A rare but extremely dangerous cause of hepatitis results from overdose of acetaminophen (Tylenol), which can be deadly. In addition, immune cells in the body may attack the liver and cause autoimmune hepatitis. Hepatitis may resolve quickly (acute hepatitis), or cause long-term disease (chronic hepatitis). In some instances, progressive liver damage or liver failure may result. The incidence and severity of hepatitis vary depending on many factors, including the cause of the liver damage and any underlying illnesses in a patient.

In one embodiment, the invention features methods for treating a hepatic disorder in which TNFα activity is detrimental, comprising administering to a subject an effective amount of a TNFα inhibitor in an induction dose and subsequently in a treatment dose, such that said disorder is treated. In one embodiment, the hepatic disorder is selected from the group consisting of hepatitis C virus, autoimmune hepatitis, fatty-liver disease, hepatitis B virus, hepatotoxicity, and non-alcoholic hepatitis, including non-alcoholic steatohepatitis (NASH). Examples of hepatic disorders are further described below.

1. Hepatitis C Virus (HCV)

Tumor necrosis factor has been implicated in the pathophysiology of the hepatitis C virus (see Gonzalez-Amaro, (1994) *J Exp Med.* 179:841; Nelson et al. (1997) *Dig Dis Sci* 42:2487; Kallinowski et al. (1998) *Clin Exp Immunol.* 111:269). The term "hepatitis C virus" or "HCV" is used to describe the hepatitis virus which is the causative agent of non-A, non-B hepatitis. Hepatitis C virus causes an inflammation of the liver. HCV infection causes hepatitis C. Hepatitis C in the acute stage is, in general, milder than hepatitis B, but a greater proportion of such infections become chronic. HCV is a major cause of acute hepatitis and chronic liver disease, including cirrhosis and liver cancer. HCV is one of the viruses (A, B, C, D, and E), which together account for the vast majority of cases of viral hepatitis. It is an enveloped RNA virus in the flaviviridae family which appears to have a narrow host range. An important feature of the virus is the relative mutability of its genome, which in turn is probably related to the high propensity (80%) of inducing chronic infection. HCV is clustered into several distinct genotypes which may be important in determining the severity of the disease and the response to treatment. In one embodiment, the invention provides a multiple-variable dose method for treating HCV.

2. Autoimmune Hepatitis (AIH)

Tumor necrosis factor has been implicated in the pathophysiology of autoimmune hepatitis (see Cookson et al., (1999) *Hepatology* 30:851; Jazrawi et al., (2003) *Liver Transpl.* 9:377). As used herein, "autoimmune hepatitis" refers to a hepatic disorder characterized by inflammation of the liver caused by rogue immune cells that mistake the liver's normal cells for a foreign tissue or pathogen (disease-causing agent). Autoimmune hepatitis is often responsible for a progressive destruction of the hepatic parenchyma with a high mortality if left untreated (Johnson et al. (1993) *Hepatology,* 18:998). One of the characteristics of autoimmune hepatitis is the presence of circulating autoantibodies in almost 90% of patients' sera. Such antibodies can be used to identify subjects who have autoimmune hepatitis.

Clinical and serological differences between patients have lead to the classification of AIH into two types. Type 1 is characterized by the presence of anti-smooth muscle (SMA) and/or anti-nuclear antibodies (ANA) in patients' sera, while sera from Type II patients show anti-liver kidney microsomal antibodies type 1 (LKM1) (Homberg et al., (1987) *Hepatology,* 7:1333; Maggiore et al. (1993) *J. Pediatr. Gastroenterol Nutr.* 17:376). A serological marker, anti-liver cytosol type I antibodies (LC1), has been identified in 30% of patients with an AIH type II. In addition, LC1 proved to be the only serological marker in 10% of patients tested (Martini et al. (1988) *Hepatology,* 8:1662). In one embodiment, the method of the invention is used to treat AIH.

3. Fatty-Liver Disease

Tumor necrosis factor has been implicated in the pathophysiology of fatty-liver disease (see Valenti et al., (2002) Gastroenerology 122:274; Li et al., (2003) *Hepatology* 37:343). Fatty-liver disease refers to a disease wherein fat (hepatocytes) is excessively accumulated in the liver. Fatty liver disease is believed to be caused by supernutrition, hyperingestion of alcohol, diabetes and side effects due to administration of pharmaceuticals. Fatty liver disease can cause severe diseases such as chronic hepatitis and hepatic cirrhosis. In patients with fatty liver disease, lipids, particularly neutral fat, accumulate in hepatocytes to the extent that the amount exceeds the physiologically permissible range. From a biochemical point of view, a standard for judgment of fatty liver is that the weight of neutral fat is about 10% (100 mg/g wet weight) or more of the wet weight of hepatic tissue. In one embodiment, the method of the invention is used to treat fatty liver disease.

4. Hepatitis B Virus (HBV)

Tumor necrosis factor has been implicated in the pathophysiology of hepatitis B virus (see Kasahara et al., (2003) *J Virol.* 77:2469; Wang (2003) *World J Gastroenterol.* 9:641; Biermer et al. (2003) *J Virol.* 77:4033). The term "hepatitis B virus" (HBV) is used to describe the virus (serum hepatitis virus) which produces viral hepatitis type B in humans. This is a viral disease with a long incubation period (about 50 to 160 days) in contrast to hepatitis A virus (infectious hepatitis virus) which has a short incubation period. The hepatitis B virus is usually transmitted by injection of infected blood or blood derivatives or merely by use of contaminated needles, lancets or other instruments. Clinically and pathologically, the disease is similar to viral hepatitis type A; however, there is no cross-protective immunity. Viral antigen (HBAg) is found in the serum after infection.

Hepatitis B virus infects humans at a very high rate. Most people who become infected with Hepatitis B get rid of the virus within 6 months, wherein a short infection is known as an "acute" case of Hepatitis B. It is estimated that at least about 300 million people are chronic carriers of HBV. Infection with the virus results in a range of clinical symptoms including minor flu-like symptoms to death. In one embodiment, the multiple-variable dose method of the invention is used to treat HBV infection.

5. Hepatotoxicity

Tumor necrosis factor has been implicated in the pathophysiology of hepatotoxicity (see Bruccoleri et al. (1997) *Hepatology* 25:133; Luster et al. (2000) *Ann NY Acad Sci.* 919:214; Simeonova et al. (2001) *Toxicol Appl Pharmacol.* 177:112). The term hepatotoxicity refers to liver damage caused by medications and other chemicals or drugs. The best indicator for identifying liver toxicity in a subject is the elevation of certain enzyme measurements in the blood, such as AST (aspartate aminotransferase), ALT (alanine aminotransferase), and GOT (glutamate oxalacetate transaminase).

Hepatotoxicity can cause permanent injury and death. Initial symptoms of hepatotoxicity can include acute gastrointestinal symptoms, e.g., severe diarrhea. The second phase of hepatotoxicity is characterized by abatement of symptoms. During this apparent subsidence, biochemical evidence of hepatic injury appears. Oliguria (decreased urine output) is usual during the second phase. The third phase, that of overt hepatic damage, becomes clinically apparent 3 to 5 days after ingestion of the chemical, with the appearance of jaundice. Renal failure may also occur. The symptoms of chemically-induced (drug-induced) hepatitis are similar to that of infectious hepatitis. In one embodiment, the method of the invention is used to treat hepatotoxicity.

6. Liver Failure (e.g. Chronic Liver Failure)

Tumor necrosis factor has been implicated in the pathophysiology of liver failure (e.g. chronic liver failure) (see Takenaka et al., (1998) *Dig Dis Sci.* 43:887; Nagaki et al. (1999) *J Hepatol.* 31:997; Streetz et al., (2000) *Gastroenterology.* 119:446. Liver failure, including chronic liver failure, usually develops over a period of years and is caused by a repeated insult to the liver (such as alcohol abuse or infection with hepatitis virus) which slowly damages the organ. Less commonly, liver failure is acute, and occurs over a period of days or weeks. Causes of acute liver failure include hepatitis virus infections, drugs, pregnancy, autoimmune disease, and sudden low blood flow to the liver. In one embodiment, the method of the invention is used to treat liver failure.

7. Non-Alcoholic Hepatitis, Including NASH

Tumor necrosis factor has been implicated in the pathophysiology of non-alcoholic hepatitis, including nonalcoholic steatohepatitis (see Crespo et al., (2001) *Hepatology.*

34:1158;Pessayre et al. (2002) 282(2):G193). The term "nonalcoholic steatohepatitis" or "NASH" refers to the development of histologic changes in the liver that are comparable to those induced by excessive alcohol intake, but in the absence of alcohol abuse. NASH is characterized by macrovesicular and/or microvesicular steatosis, lobular and portal inflammation, and occasionally Mallory bodies with fibrosis and cirrhosis. NASH is also commonly associated with hyperlipidemia, obesity, and type II diabetes mellitus.

Additional clinical conditions which characterize hepatic steatosis and inflammation include excessive fasting, jejunoileal bypass, total parental nutrition, chronic hepatitis C, Wilson's disease, and adverse drug effects such as those from corticosteroids, calcium channel blockers, high dose synthetic estrogens, methotrexate and amiodarone. Thus, the term "nonalcoholic steatohepatitis" can be used to describe those patients who exhibit these biopsy findings, coupled with the absence of (a) significant alcohol consumption, (b) previous surgery for weight loss, (c) history of drug use associated with steatohepatitis, (d) evidence of genetic liver disease or (e) chronic hepatitis C infection (see, e.g., Ludwig et al., (1980) *Mayo Clin. Proc.* 55:434; Powell et al. (1990) *Hepatol.* 11:74). In one embodiment, the antibodies obtained using the method of the invention are used to treat NASH.

N. Skin and Nail Disorders

Tumor necrosis factor has been implicated in the pathophysiology of skin and nail disorders. In one embodiment, antibodies obtained using the method of the invention are administered to treat skin and nail disorders. The term "skin disorder" or "skin disease" as used interchangeably herein, refers to abnormalities, other than injury wounds, of the skin which have induced a state of inflammation. In one embodiment, the skin disorder of the invention is an inflammatory skin disorder, wherein the skin is characterized by capillary dilatation, leukocytic infiltration, redness, heat, and/or pain. Examples of skin disorders include, but are not limited to, psoriasis, pemphigus vulgaris, scleroderma, atopic dermatitis, sarcoidosis, erythema nodosum, hidradenitis suppurative, lichen planus, Sweet's syndrome, and vitiligo. As used herein, the term "skin and nail disorder in which TNFα activity is detrimental" is intended to include skin and/or nail disorders and other disorders in which the presence of TNFα in a subject suffering from the disorder has been shown to be or is suspected of being either responsible for the pathophysiology of the disorder or a factor that contributes to a worsening of the disorder, e.g., psoriasis. Accordingly, skin and nail disorders in which TNFα activity is detrimental are disorders in which inhibition of TNFα activity is expected to alleviate the symptoms and/or progression of the disorder. The use of the antibodies, antibody portions, and other TNFα inhibitors of the invention in the treatment of specific skin and nail disorders is discussed further below. In certain embodiments, the treatment method of the invention is performed in combination with another therapeutic agent, as described below. In one embodiment, the antibodies obtained using the method of the invention comprising administering a TNFα antibody in combination with another therapeutic agent is used for the treatment of psoriasis and the treatment of psoriasis associated with arthritis.

1. Psoriasis

Tumor necrosis factor has been implicated in the pathophysiology of psoriasis (Takematsu et al. (1989) *Arch Dermatol Res.* 281:398; Victor and Gottlieb (2002) *J Drugs Dermatol.* 1:264). The term "psoriasis" as used herein, refers to skin disorders associated with epidermal hyperplasia. Example of psoriasis include, but are not limited to, chronic plaque psoriasis, guttate psoriasis, inverse psoriasis, pustular psoriasis, psoriasis vulgaris, and erythrodermic psoriasis. Psoriasis can also be associated with other inflammatory disorders, including inflammatory bowel disease (IBD) and rheumatoid arthritis (RA).

Psoriasis is described as a skin inflammation (irritation and redness) characterized by frequent episodes of redness, itching, and thick, dry, silvery scales on the skin. In particular, lesions are formed which involve primary and secondary alterations in epidermal proliferation, inflammatory responses of the skin, and an expression of regulatory molecules such as lymphokines and inflammatory factors. Psoriatic skin is morphologically characterized by an increased turnover of epidermal cells, thickened epidermis, abnormal keratinization, inflammatory cell infiltrates into the epidermis and polymorphonuclear leukocyte and lymphocyte infiltration into the epidermis layer resulting in an increase in the basal cell cycle. Psoriasis often involves the nails, which frequently exhibit pitting, separation of the nail, thickening, and discoloration. Psoriasis is often associated with other inflammatory disorders, for example arthritis, including rheumatoid arthritis, inflammatory bowel disease (IBD), and Crohn's disease. Approximately one thrid of subjects with psoriasis also have psoriatic arthritis (PsA) which, as described above, causes stiffness, swelling of the joints, pain, and reducd range of motion (Greaves et al. (1995) *N. Eng. J. Med.* 332:581).

Evidence of psoriasis is most commonly seen on the trunk, elbows, knees, scalp, skin folds, or fingernails, but it may affect any or all parts of the skin. Normally, it takes about a month for new skin cells to move up from the lower layers to the surface. In psoriasis, this process takes only a few days, resulting in a build-up of dead skin cells and formation of thick scales. Symptoms of psoriasis include: skin patches, that are dry or red, covered with silvery scales, raised patches of skin, accompanied by red borders, that may crack and become painful, and that are usually located on the elbows, knees, trunk, scalp, and hands; skin lesions, including pustules, cracking of the skin, and skin redness; joint pain or aching which may be associated with of arthritis, e.g., psoriatic arthritis.

Treatment for psoriasis often includes a topical corticosteroids, vitamin D analogs, and topical or oral retinoids, or combinations thereof. In one embodiment, the TNFα antibody of the invention is administered in combination with or the presence of one of these common treatments. Additional therapeutic agents which can be combined with the TNFα antibody obtained using the methods of the invention for treatment of psoriasis are described in more detail below.

The diagnosis of psoriasis is usually based on the appearance of the skin. Additionally a skin biopsy, or scraping and culture of skin patches may be needed to rule out other skin disorders. An x-ray may be used to check for psoriatic arthritis if joint pain is present and persistent.

Improvements in psoriasis in a subject can be monitored by the subject's Psoriasis Area and Severity Index Score (PASI). The method for determining the PASI has been described in Fredriksson and Pettersson (1978) *Dermatologica* 157:238 and Marks et al. (1989) *Arch Dermatol* 125:235. Briefly, the index is based on evaluation of four anatomic sites, including the head, upper extremities, trunk, and lower extremities, for erythema, induration, and desquamation using a 5 point scale (0=no symptoms; 1=slight; 2=moderate; 3=marked; 4=very marked). Based on the extent of lesions in a given anatomic site, the area affected is assigned a numerical value (0=0; 1=<10%; 2=10-29%; 3=30-49%; 4=50-69%; 5=70-89%; 6=90-100%). The PASI score is then calculated, wherein the possible range of PASI score is 0.0 to 72.0 with the highest score representing complete erythroderma of the severest degree.

In one embodiment of the invention, a TNFα antibody is used for the treatment of psoriasis, including chronic plaque psoriasis, guttate psoriasis, inverse psoriasis, pustular psoriasis, pemphigus vulgaris, erythrodermic psoriasis, psoriasis associated with inflammatory bowel disease (IBD), and psoriasis associated with rheumatoid arthritis (RA). In another embodiment, a TNFα antibody, such as adalimumab, is used to treat subjects who have psoriasis in combination with PsA. Specific types of psoriasis included in the treatment methods of the invention are described in detail below:

a. Chronic Plaque Psoriasis

Tumor necrosis factor has been implicated in the pathophysiology of chronic plaque psoriasis (Asadullah et al. (1999) *Br J Dermatol.* 141:94). Chronic plaque psoriasis (also referred to as psoriasis vulgaris) is the most common form of psoriasis. Chronic plaque psoriasis is characterized by raised reddened patches of skin, ranging from coin-sized to much larger. In chronic plaque psoriasis, the plaques may be single or multiple, they may vary in size from a few millimeters to several centimeters. The plaques are usually red with a scaly surface, and reflect light when gently scratched, creating a "silvery" effect. Lesions (which are often symmetrical) from chronic plaque psoriasis occur all over body, but with predilection for extensor surfaces, including the knees, elbows, lumbosacral regions, scalp, and nails. Occasionally chronic plaque psoriasis can occur on the penis, vulva and flexures, but scaling is usually absent. Diagnosis of patients with chronic plaque psoriasis is usually based on the clinical features described above. In particular, the distribution, color and typical silvery scaling of the lesion in chronic plaque psoriasis are characteristic of chronic plaque psoriasis.

b. Guttate Psoriasis

Guttate psoriasis refers to a form of psoriasis with characteristic water drop shaped scaly plaques. Flares of guttate psoriasis generally follow an infection, most notably a streptococcal throat infection. Diagnosis of guttate psoriasis is usually based on the appearance of the skin, and the fact that there is often a history of recent sore throat.

c. Inverse Psoriasis

Inverse psoriasis is a form of psoriasis in which the patient has smooth, usually moist areas of skin that are red and inflamed, which is unlike the scaling associated with plaque psoriasis. Inverse psoriasis is also referred to as intertiginous psoriasis or flexural psoriasis. Inverse psoriasis occurs mostly in the armpits, groin, under the breasts and in other skin folds around the genitals and buttocks, and, as a result of the locations of presentation, rubbing and sweating can irriate the affected areas.

d. Pustular Psoriasis

Pustular psoriasis, also referred to as palmar plantar psoriasis, is a form of psoriasis that causes pus-filled blisters that vary in size and location, but often occur on the hands and feet. The blisters may be localized, or spread over large areas of the body. Pustular psoriasis can be both tender and painful, can cause fevers.

e. Other Psoriasis Disorders

Other examples of psoriatic disorders which can be treated with the TNFα antibody obtained using the methods of the invention include erythrodermic psoriasis, vulgaris, psoriasis associated with IBD, and psoriasis associated with arthritis, including rheumatoid arthritis.

2. Pemphigus Vulgaris

Pemphigus vulgaris is a serious autoimmune systemic dermatologic disease that often affects the oral mucous membrane and skin. The pathogenesis of pemphigus vulgaris is thought to be an autoimmune process that is directed at skin and oral mucous membrane desmosomes. Consequentially, cells do not adhere to each other. The disorder manifests as large fluid-filled, rupture-prone bullae, and has a distinctive histologic appearance. Anti-inflammatory agents are the only effective therapy for this disease which has a high mortality rate. Complications that arise in patients suffering from pemphigus vulgaris are intractable pain, interference with nutrition and fluid loss, and infections.

3. Atopic Dermatitis/Eczema

Atopic dermatitis (also referred to as eczema) is a chronic skin disorder categorized by scaly and itching plaques. People with eczema often have a family history of allergic conditions like asthma, hay fever, or eczema. Atopic dermatitis is a hypersensitivity reaction (similar to an allergy) which occurs in the skin, causing chronic inflammation. The inflammation causes the skin to become itchy and scaly. Chronic irritation and scratching can cause the skin to thicken and become leathery-textured. Exposure to environmental irritants can worsen symptoms, as can dryness of the skin, exposure to water, temperature changes, and stress.

Subjects with atopic dermatitis can be identified by certain symptoms, which often include intense itching, blisters with oozing and crusting, skin redness or inflammation around the blisters, rash, dry, leathery skin areas, raw areas of the skin from scratching, and ear discharges/bleeding.

4. Sarcoidosis

Sarcoidosis is a disease in which granulomatous inflammation occurs in the lymph nodes, lungs, liver, eyes, skin, and/or other tissues. Sarcoidosis includes cutaneous sarcoidosis (sarcoidosis of the skin) and nodular sarcoidosis (sarcoidosis of the lymph nodes). Patients with sarcoidosis can be identified by the symptoms, which often include general discomfort, uneasiness, or an ill feeling; fever; skin lesions.

5. Erythema Nodosum

Erythema nodosum refers to an inflammatory disorder that is characterized by tender, red nodules under the skin, typically on the anterior lower legs. Lesions associated with erythema nodosum often begin as flat, but firm, hot red painful lumps (approximately an inch across). Within a few days the lesions may become purplish, and then over several weeks fade to a brownish flat patch.

In some instances, erythema nodosum may be associated with infections including, streptococcus, coccidioidomycosis, tuberculosis, hepatitis B, syphilis, cat scratch disease, tularemia, yersinia, leptospirosis psittacosis, histoplasmosis, mononucleosis (EBV). In other instances, erythema nodosum may be associated with sensitivity to certain medications including, oralcontraceptives, penicillin, sulfonamides, sulfones, barbiturates, hydantoin, phenacetin, salicylates, iodides, and progestin. Erythema nodosum is often associated with other disorders including, leukemia, sarcoidosis, rheumatic fever, and ulcerative colitis.

Symptoms of erythema nodosum usually present themselves on the shins, but lesions may also occur on other areas of the body, including the buttocks, calves, ankles, thighs and upper extremities. Other symptoms in subjects with erythema nodosum can include fever and malaise.

6. Hidradenitis Suppurative

Hidradenitis suppurativa refers to a skin disorder in which swollen, painful, inflamed lesions or lumps develop in the groin and sometimes under the arms and under the breasts. Hidradenitis suppurativa occurs when apocrine gland outlets become blocked by perspiration or are unable to drain normally because of incomplete gland development. Secretions trapped in the glands force perspiration and bacteria into surrounding tissue, causing subcutaneous induration, inflammation, and infection. Hidradenitis suppurativa is confined to areas of the body that contain apocrine glands. These areas are the axillae, areola of the nipple, groin, perineum, circumanal, and periumbilical regions.

7. Lichen Planus

Tumor necrosis factor has been implicated in the pathophysiology of lichen planus (Sklavounou et al. (2000) *J Oral Pathol Med.* 29:370). Lichen planus refers to a disorder of the skin and the mucous membranes resulting in inflammation, itching, and distinctive skin lesions. Lichen planus may be associated with hepatitis C or certain medications.

8. Sweet's Syndrome

Inflammatory cytokines, including tumor necrosis factor, have been implicated in the pathophysiology of Sweet's syndrome (Reuss-Borst et al. (1993) *Br J Haemaotol.* 84:356). Sweet's syndrome, which was described by R. D. Sweet in 1964, is characterized by the sudden onset of fever, leukocytosis, and cutaneous eruption. The eruption consists of tender, erythematous, well-demarcated papules and plaques which show dense neutrophilic infiltrates microscopically. The lesions may appear anywhere, but favor the upper body including the face. The individual lesions are often described as pseudovesicular or pseudopustular, but may be frankly pustular, bullous, or ulcerative. Oral and eye involvement (conjunctivitis or episcleritis) have also been frequently reported in patients with Sweet's syndrome. Leukemia has also been associated with Sweet's syndrome.

9. Vitiligo

Vitiligo refers to a skin condition in which there is loss of pigment from areas of skin resulting in irregular white patches with normal skin texture. Lesions characteristic of vitiligo appear as flat depigmented areas. The edges of the lesions are sharply defined but irregular. Frequently affected areas in subjects with vitiligo include the face, elbows and knees, hands and feet, and genitalia.

10. Scleroderma

Tumor necrosis factor has been implicated in the pathophysiology of scleroderma (Tutuncu et al. (2002) *Clin Exp Rheumatol.* 20(6 Suppl 28):S146; Mackiewicz et al. (2003) *Clin Exp Rheumatol.* 21:41; Murota et al. (2003) *Arthritis Rheum.* 48:1117). Scleroderma refers to a a diffuse connective tissue disease characterized by changes in the skin, blood vessels, skeletal muscles, and internal organs. Scleroderma is also referred to as CREST syndrome or progressive systemic sclerosis, and usually affects people between the ages 30-50. Women are affected more often than men.

The cause of scleroderma is unknown. The disease may produce local or systemic symptoms. The course and severity of the disease varies widely in those affected.Excess collagen deposits in the skin and other organs produce the symptoms. Damage to small blood vessels within the skin and affected organs also occurs. In the skin, ulceration, calcification, and changes in pigmentation may occur. Systemic features may include fibrosis and degeneration of the heart, lungs, kidneys and gastrointestinal tract.

Patients suffering from scleroderma exhibit certain clinical features, including, blanching, blueness, or redness of fingers and toes in response to heat and cold (Raynaud's phenomenon), pain, stiffness, and swelling of fingers and joints, skin thickening and shiny hands and forearm, esophageal reflux or heartburn, difficulty swallowing, and shortness of breath. Other clinical sypmtoms used to diagnose scleroderma include, an elevated erythrocyte sedimentaion rate (ESR), an elevated rheumatoid factor (RF), a positive antinuclear antibody test, urinalysis that shows protein and microscopic blood, a chest X-ray that may show fibrosis, and pulmonary funtion studies that show restricitive lung disease.

11. Nail Disorders

Nail disorders include any abnormality of the nail. The term "nail disorder" or "nail disease" as used herein, refers to conditions wherein the fingernails or toenails to abnormal color, shape, texture, or thickness. Specific nail disorders include, but are not limited to, pitting, koilonychia, Beau's lines, spoon nails, onycholysis, yellow nails, pterygium (seen in lichen planus), and leukonychia. Pitting is characterised by the presence of small depressions on the nail surface. Ridges or linear elevations can develop along the nail occurring in a "lengthwise" or "crosswise" direction. Beau's lines are linear depressions that occur "crosswise" (transverse) in the fingernail. Leukonychia describes white streaks or spots on the nails. Koilonychia is an abnormal shape of the fingernail where the nail has raised ridges and is thin and concave Koilonychia is often associated with iron deficiency.

Nail disorders which can be treated with the TNFα antibody of the invention also include psoriatic nails. Psoriatic nails include changes in nails which are attributable to psoriasis. In some instances psoriasis may occur only in the nails and nowhere else on the body. Psoriatic changes in nails range from mild to severe, generally reflecting the extent of psoriatic involvement of the nail plate, nail matrix, i.e., tissue from which the nail grows, nail bed, i.e., tissue under the nail, and skin at the base of the nail. Damage to the nail bed by the pustular type of psoriasis can result in loss of the nail. Nail changes in psoriasis fall into general categories that may occur singly or all together. In one category of psoriatic nails, the nail plate is deeply pitted, probably due to defects in nail growth caused by psoriasis. In another category, the nail has a yellow to yellow-pink discoloration, probably due to psoriatic involvement of the nail bed. A third subtype of psoriatic nails are characterized by white areas which appear under the nail plate. The white areas are actually air bubbles marking spots where the nail plate is becoming detached from the nail bed. There may also be reddened skin around the nail. A fourth category is evidenced by the nail plate crumbling in yellowish patches, i.e., onychodystrophy, probably due to psoriatic involvement in the nail matrix. A fifth category is characterized by the loss of the nail in its entirety due to psoriatic involvement of the nail matrix and nail bed.

Antbodies obtained using the method of the invention can also be used to treat nail disorders often associated with lichen planus. Nails in subjects with lichen planus often show thinning and surface roughness of the nail plate with longitudinal ridges or pterygium.

The antbodies obtained using the invention can be used to treat nail disorders, such as those described herein. Often nail disorders are associated with skin disorders. In one embodiment, the invention treatment for nail disorders using a TNFα antibody. In another embodiment, the nail disorder is associated with another disorder, including a skin disorder such as psoriasis. In another embodiment, the disorder associated with a nail disorder is arthritis, including psoriatic arthritis.

12. Other Skin and Nail Disorders

Antbodies obtained using the method of the invention can be used to treat other skin and nail disorders, such as chronic actinic dermatitis, bullous pemphigoid, and alopecia areata.

Chronic actinic dermatitis (CAD) is also referred to as photosensitivity dermatitis/actinic reticuloid syndrome (PD/AR). CAD is a condition in which the skin becomes inflamed, particularly in areas that have been exposed to sunlight or artificial light. Commonly, CAD patients have allergies to certain substances that come into contact with their skin, particularly various flowers, woods, perfumes, sunscreens and rubber compounds. Bullous pemphigoid refers to a skin disorder characterized by the formation of large blisters on the trunk and extremities. Alopecia areata refers to hair loss characterized by round patches of complete baldness in the scalp or beard.

O. Vasculitides

TNFα has been implicated in the pathophysiology of a variety of vasculitides, (see e.g., Deguchi et al. (1989) Lancet. 2:745). In one embodiment, the invention provides a multiple-variable dose method for inhibiting TNFα activity in a subject suffering from a vasculitis in which TNFα activity is detrimental.

The term "vasculitis" or "vasculitides" as used interchangeably herein, refers to a group of disorders which are characterized by the inflammation of blood vessels. Blood vessels of all sizes may be affected, from the largest vessel in the body (the aorta) to the smallest blood vessels in the skin (capillaries). The size of blood vessel affected varies according to the specific type of vasculitis. As used herein, the term "a vasculitis in which TNFα activity is detrimental" is intended to include vasculitis in which the presence of TNFα in a subject suffering from the disorder has been shown to be or is suspected of being either responsible for the pathophysiology of the disorder or a factor that contributes to a worsening of the disorder. Such disorders may be evidenced, for example, by an increase in the concentration of TNFα in a biological fluid of a subject suffering from the disorder (e.g., an increase in the concentration of TNFα in serum, plasma, synovial fluid, etc. of the subject), which can be detected, for example, using an anti-TNFα antibody as described above.

There are numerous examples of vasculitides in which TNFα activity is detrimental, including Behcet's disease. The use of the antibodies, or antigen-binding portions thereof, for treatment of specific vasculitides is discussed further below. In certain embodiments, the antibody, or antibody portion, obtained using the invention is administered to the subject in combination with another therapeutic agent, as described below.

The antibody, or antibody portion, obtained using the invention may also be used to treat vasculitis in which TNFα activity is detrimental, wherein inhibition of TNFα activity is expected to alleviate the symptoms and/or progression of the vasculitis or to prevent the vasculitis. Subjects suffering from or at risk of developing vasculitis can be identified through clinical symptoms and tests. For example, subjects with vasculitides often develop antibodies to certain proteins in the cytoplasm of neutrophils, antineutrophil cytoplasmic antibodies (ANCA). Thus, in some instances, vasculitides may be evidenced by tests (e.g., ELISA), which measure ANCA presence.

Vasculitis and its consequences may be the sole manifestation of disease or it may be a secondary component of another primary disease. Vasculitis may be confined to a single organ or it may simultaneously affect several organs, and depending on the syndrome, arteries and veins of all sizes can be affected. Vasculitis can affect any organ in the body.

In vasculitis, the vessel lumen is usually compromised, which is associated with ischemia of the tissues supplied by the involved vessel. The broad range of disorders that may result from this process is due to the fact that any type, size and location of vessel (e.g., artery, vein, arteriole, venule, capillary) can be involved. Vasculitides are generally classified according to the size of the affected vessels, as described below. It should be noted that some small and large vessel vasculitides may involve medium-sized arteries; but large and medium-sized vessel vasculitides do not involve vessels smaller than arteries. Large vessel disease includes, but is not limited to, giant cell arteritis, also known as temporal arteritis or cranial arteritis, polymyalgia rheumatica, and Takayasu's disease or arteritis, which is also known as aortic arch syndrome, young female arteritis and Pulseless disease. Medium vessel disease includes, but is not limited to, classic polyarteritis nodosa and Kawasaki's disease, also known as mucocutaneous lymph node syndrome. Non-limiting examples of small vessel disease are Behcet's Syndrome, Wegner's granulomatosis, microscopic polyangitis, hypersensitivity vasculitis, also known as cutaneous vasculitis, small vessel vasculitis, Henoch-Schonlein purpura, allergic granulamotosis and vasculitis, also known as Churg Strauss syndrome. Other vasculitides include, but are not limited to, isolated central nervous system vasculitis, and thromboangitis obliterans, also known as Buerger's disease. Classic Polyarteritis nodosa (PAN), microscopic PAN, and allergic granulamotosis are also often grouped together and are called the systemic necrotizing vasculitides. A further description of vasculitis is described below:

1. Large Vessel Vasculitis

In one embodiment, the TNFα antibody obtained using the invention may be used to treat subjects who have large vessel vasculitis. The term "large vessel(s)" as used herein, refers to the aorta and the largest branches directed toward major body regions. Large vessels include, for example, the aorta, and its branches and corresponding veins, e.g., the subclavian artery; the brachiocephalic artery; the common carotid artery; the innominate vein; internal and external jugular veins; the pulmonary arteries and veins; the venae cavae; the renal arteries and veins; the femoral arteries and veins; and the carotid arteries. Examples of large vessel vasculitides are described below.

a. Giant Cell Arteritis (GCA)

Tumor necrosis factor has been implicated in the pathophysiology of giant cell arteritis (Sneller (2002) Cleve. Clin. J. Med. 69:SII40; Schett et al. (2002) Ann. Rheum. Dis. 61:463). Giant cell arteritis (GCA), refers to a vasculitis involving inflammation and damage to blood vessels, particularly the large or medium arteries that branch from the external carotid artery of the neck. GCA is also referred to as temporal arteritis or cranial arteritis, and is the most common primary vasculitis in the elderly. It almost exclusively affects individuals over 50 years of age, however, there are well-documented cases of patients 40 years and younger. GCA usually affects extracranial arteries. GCA can affect the branches of the carotid arteries, including the temporal artery. GCA is also a systemic disease which can involve arteries in multiple locations.

Histopathologically, GCA is a panarteritis with inflammatory mononuclear cell infiltrates within the vessel wall with frequent Langhans type giant cell formation. There is proliferation of the intima, granulomatous inflammation and fragmentation of the internal elastic lamina. The pathological findings in organs is the result of ischemia related to the involved vessels.

Patients suffering from GCA exhibit certain clinical symptoms, including fever, headache, anemia and high erythrocyte sedimentation rate (ESR). Other typical indications of GCA include jaw or tongue claudication, scalp tenderness, constitutional symptoms, pale optic disc edema (particularly 'chalky white' disc edema), and vision disturbances. The diagnosis is confirmed by temporal artery biopsy.

b. Polymyalgia Rheumatica

Tumor necrosis factor has been implicated in the pathophysiology of polymyalgia rheumatica (Straub et al. (2002) *Rheumatology* (Oxford) 41:423; Uddhammar et al. (1998) *Br. J. Rheumatol.* 37:766). Polymyalgia rheumatica refers to a rheumatic disorder that is associated with moderate to severe muscle pain and stiffness in the neck, shoulder, and hip, most noticeable in the morning. IL-6 and IL-1β expression has also been detected in a majority of the circulating monocytes in patients with the polymyalgia rheumatica. Polymyalgia rheumatica may occur independently, or it may coexist with or precede GCA, which is an inflammation of blood vessels.

c. Takayasu's Arteritis

Tumor necrosis factor has been implicated in the pathophysiology of Takayasu's arteritis (Kobayashi and Numano (2002) *Intern. Med.* 41:44; Fraga and Medina (2002) *Curr. Rheumatol. Rep.* 4:30). Takayasu's arteritis refers to a vasculitis characterized by an inflammmation of the aorta and its major branches. Takayasu's arteritis (also known as Aortic arch syndrome, young female arteritis and Pulseless disease) affects the thoracic and abdominal aorta and its main branches or the pulmonary arteries. Fibrotic thickening of the aortic wall and its branches (e.g., carotid, inominate, and subclavian arteries) can lead to reduction of lumen size of vessels that arise from the aortic arch. This condition also typically affects the renal arteries.

Takayasu's arteritis primarily affects young women, usually aged 20-40 years old, particularly of Asian descent, and may be manifested by malaise, arthralgias and the gradual onset of extremity claudication. Most patients have asymmetrically reduced pulses, usually along with a blood pressure differential in the arms. Coronary and/or renal artery stenosis may occur.

The clinical features of Takayasu's arteritis may be divided into the features of the early inflammatory disease and the features of the later disease. The clinical features of the early inflammatory stage of Takayasu's disease are: malaise, low grade fever, weight loss, myalgia, arthralgia, and erythema multiforme. Later stages of Takayasu's disease are characterized by fibrotic stenosis of arteries and thrombosis. The main resulting clinical features are ischaemic phenomena, e.g. weak and asymmetrical arterial pulses, blood pressure discrepancy between the arms, visual disturbance, e.g. scotomata and hemianopia, other neurological features including vertigo and syncope, hemiparesis or stroke. The clinical features result from ischaemia due to arterial stenosis and thrombosis.

2. Medium Vessel Disease

In one embodiment, the TNFα antibody obtained using the invention may be used to treat subjects who have medium vessel vasculitis. The term "medium vessel(s)" is used to refer to those blood vessels which are the main visceral arteries. Examples of medium vessels include the mesenteric arteries and veins, the iliac arteries and veins, and the maxillary arteries and veins. Examples of medium vessel vasculitides are described below.

a. Polyarteritis Nodosa

Tumor necrosis factor has been implicated in the pathophysiology of polyarteritis nodosa (DiGirolamo et al. (1997) *J. Leukoc. Biol.* 61:667). Polyarteritis nodosa, or periarteritis nodosa refers to vasculitis which is a serious blood vessel disease in which small and medium-sized arteries become swollen and damaged because they are attacked by rogue immune cells. Polyarteritis nodosa usually affects adults more frequently than children. It damages the tissues supplied by the affected arteries because they don't receive enough oxygen and nourishment without a proper blood supply.

Symptoms which are exhibited in patients with polyarteritis nodosa generally result from damage to affected organs, often the skin, heart, kidneys, and nervous system. Generalized symptoms of polyarteritis nodosa include fever, fatigue, weakness, loss of appetite, and weight loss. Muscle aches (myalgia) and joint aches (arthralgia) are common. The skin of subjects with polyarteritis nodosa may also show rashes, swelling, ulcers, and lumps (nodular lesions).

Classic PAN (polyarteritis nodosa) is a systemic arteritis of small to medium muscular arteritis in which involvement of renal and visceral arteries is common Abdominal vessels have aneurysms or occlusions in 50% of PAN patients. Classic PAN does not involve the pulmonary arteries although the bronchial vessels may be involved. Granulomas, significant eosinophilia and an allergic diathesis are not part of the syndrome. Although any organ system may be involved, the most common manifestations include peripheral neuropathy, mononeuritis multiplex, intestinal ischemia, renal ischemia, testicular pain and livedo reticularis.

b. Kawasaki's Disease

Tumor necrosis factor has been implicated in the pathophysiology of Kawasaki's disease (Sundel (2002) *Curr. Rheumatol. Rep.* 4:474; Gedalia (2002) *Curr. Rheumatol. Rep.* 4:25). Although the cause of Kawasaki's disease is unknown, it is associated with acute inflammation of the coronary arteries, suggesting that the tissue damage associated with this disease may be mediated by proinflammatory agents such as TNFα. Kawasaki's disease refers to a vasculitis that affects the mucus membranes, lymph nodes, lining of the blood vessels, and the heart. Kawasaki's disease is also often referred to as mucocutaneous lymph node syndrome, mucocutaneous lymph node disease, and infantile polyarteritis. Subjects afflicted with Kawasaki's disease develop vasculitis often involving the coronary arteries which can lead to myocarditis and pericarditis. Often as the acute inflammation diminishes, the coronary arteries may develop aneurysm, thrombosis, and lead to myocardial infarction.

Kawasaki's disease is a febrile systemic vasculitis associated with edema in the palms and the soles of the feet, with enlargement of cervical lymph nodes, cracked lips and "strawberry tongue". Although the inflammatory response is found in vessels throughout the body, the most common site of end-organ damage is the coronary arteries. Kawasaki's Disease predominantly affects children under the age of 5. The highest incidence is in Japan but is becoming increasingly recognized in the West and is now the leading cause of acquired heart disease in US children. The most serious complication of Kawasaki disease is coronary arteritis and aneurysm formation that occurs in a third of untreated patients.

3. Small Vessel Disease

In one embodiment, a TNFα antibody is used to treat subjects who have small vessel vasculitis. The term "small vessel(s)" is used to refer to arterioles, venules and capillaries. Arterioles are arteries that contain only 1 or 2 layers of sooth muscle cells and are terminal to and continuous with the capillary network. Venules carry blood from the capillary network to veins and capillaries connect arterioles and venules. Examples of small vessel vasculitides are described below.

a. Behcet's Disease

Tumor necrosis factor has been implicated in the pathophysiology of Behcet's disease (Sfikakis (2002) *Ann. Rheum. Dis.* 61:ii51-3; Dogan and Farah (2002) *Oftalmologia.* 52:23). Behcet's disease is a chronic disorder that involves inflammation of blood vessels throughout the body. Behcet's disease may also cause various types of skin lesions, arthritis, bowel inflammation, and meningitis (inflammation of the membranes of the brain and spinal cord). As a result of Behcet's disease, the subject with the disorder may have inflammation in tissues and organs throughout the body, including the gastrointestinal tract, central nervous system, vascular system, lungs, and kidneys. Behcet's disease is three times more common in males than females and is more common in the eastern Mediterranean and Japan.

Subjects who have Behcet's disease may show clinical symptoms including recurrent oral ulcers (resembling canker sores), recurrent genital ulcers, and eye inflammation. Serum levels of TNFα, IL-8, IL-1, IL-6 INF-γ and IL-12 are elevated in Behcet's patients, and the production of these factors has been shown to be elevated in the monocytes of Behcet's patients (see, e.g., *Inflammatory Disease of Blood Vessels* (2001) Marcel Dekker, Inc., eds. G. S. Hoffman and C. M. Weyand, p. 473).

b. Wegener's Granulomatosis

Tumor necrosis factor has been implicated in the pathophysiology of Wegener's granulomatosis (Marquez et al. (2003) *Curr. Rheumatol. Rep.* 5:128; Harman and Margo (1998) *Surv. Ophthalmol.* 42:458). Wegener's granulomatosis refers to a vasculitis that causes inflammation of blood vessels in the upper respiratory tract (nose, sinuses, ears), lungs, and kidneys. Wegener's granulomatosis is also referred to as midline granulomatosis. Wegener's granulomatosis includes a granulomatous inflammation involving the respiratory tract, and necrotizing vasculitis affecting small to medium-sized vessels. Subjects who have Wegener's granulomatosis often also have arthritis (joint inflammation). Glomerulonephritis may also be present in affected subjects, but virtually any organ may be involved.

Patients affected with Wegener's granulomatosis typically show clinical symptoms comprising recurrent sinusitis or epistaxis, mucosal ulcerations, otitis media, cough, hemoptysis and dyspnea. The first symptoms of Wegener's granulomatosis frequently include upper respiratory tract symptoms, joint pains, weakness, and tiredness.

c. Churg-Strauss Syndrome

Tumor necrosis factor has been implicated in the pathophysiology of Churg-Strauss syndrome (Gross (2002) *Curr. Opin. Rheumatol.* 14:11; Churg (2001) *Mod. Pathol.* 14:1284). Churg-Strauss syndrome refers to a vasculitis that is systemic and shows early manifestation signs of asthma and eosinophilia. Churg-Strauss syndrome is also referred to as allergic granulomatosis and angiitis, and occurs in the setting of allergic rhinitis, asthma and eosinophilia. Sinusitis and pulmonary infiltrates also occur in Churg-Strauss syndrome, primarily affecting the lung and heart. Peripheral neuropathy, coronary arteritis and gastrointestinal involvement are common Patients afflicted with Churg-Strauss syndrome can be diagnosed according to criteria established by the American College of Rheumatology (ACR). These criteria were intended to distinguish CSS from other forms of vasculitis. Not all patients meet every criterion. Some, in fact, may have only 2 or 3 criteria, yet they are still classified as Churg-Strauss syndrome. The ACR selected 6 disease features (criteria) as being those that best distinguished Churg-Strauss syndrome from other vasculitides. These criteria include: 1) asthma; 2) eosinophilia [>10% on differential WBC count]; 3) mononeuropathy; 4) transient pulmonary infiltrates on chest X-rays; 5) paranasal sinus abnormalities; and 6) biopsy comprising a blood vessel with extravascular eosinophils.

P. Other TNF α-Related Disorders

In one embodiment, the invention features a multiple-variable dose method for treating a TNFα-related disorder in which TNFα activity is detrimental, comprising administering to a subject a TNFα antibody, such that said TNFα-related disorder is treated. Examples of TNFα-related disorders in which TNFα activity is detrimental, are discussed further below.

1. Juvenile Arthritis

Tumor necrosis factor has been implicated in the pathophysiology of juvenile arthritis, including juvenile rheumatoid arthritis (Grom et al. (1996) *Arthritis Rheum.* 39:1703; Mangge et al. (1995) *Arthritis Rheum.* 8:211). In one embodiment, the TNFα antibody of the invention is used to treat juvenile rheumatoid arthritis.

The term "juvenile rheumatoid arthritis" or "JRA" as used herein refers to a chronic, inflammatory disease which occurs before age 16 that may cause joint or connective tissue damage. JRA is also referred to as juvenile chronic polyarthritis and Still's disease.

JRA causes joint inflammation and stiffness for more than 6 weeks in a child of 16 years of age or less. Inflammation causes redness, swelling, warmth, and soreness in the joints. Any joint can be affected and inflammation may limit the mobility of affected joints. One type of JRA can also affect the internal organs.

JRA is often classified into three types by the number of joints involved, the symptoms, and the presence or absence of certain antibodies found by a blood test. These classifications help the physician determine how the disease will progress and whether the internal organs or skin is affected. The classifications of JRA include the following a. Pauciarticular JRA, wherein the patient has four or fewer joints are affected. Pauciarticular is the most common form of JRA, and typically affects large joints, such as the knees.

b. Polyarticular HRA, wherein five or more joints are affected. The small joints, such as those in the hands and feet, are most commonly involved, but the disease may also affect large joints.

c. Systemic JRA is characterized by joint swelling, fever, a light skin rash, and may also affect internal organs such as the heart, liver, spleen, and lymph nodes. Systemic JRA is also referred to as it Still's disease. A small percentage of these children develop arthritis in many joints and can have severe arthritis that continues into adulthood.

2. Endometriosis

Tumor necrosis factor has been implicated in the pathophysiology of endometriosis, as women with endometriosis have elevated peritoneal levels of TNF (Eisermann et al. (1988) *Fertil Steril* 50:573; Halme (1989) *Am J Obstet Gynecol* 161:1718; Mori et al. (1991) *Am J Reprod Immunol* 26:62; Taketani et al. (1992) *Am J Obstet Gynecol* 167:265; Overton et al. (1996) *Hum Reprod* 1996; 11:380). In one embodiment, the TNFα antibody may be used to treat endometriosis. The term "endometriosis" as used herein refers to a condition in which the tissue that normally lines the uterus (endometrium) grows in other areas of the body, causing pain, irregular bleeding, and frequently infertility.

3. Prostatitis

Tumor necrosis factor has been implicated in the pathophysiology of prostatitis, as men with chronic prostatitis and chronic pelvic pain have significantly higher levels of TNF and IL-1 in semen compared to controls (Alexander et al. (1998) *Urology* 52:744; Nadler et al. (2000) *J Urol* 164:214; Orhan et al. (2001) *Int J Urol* 8:495) Furthermore, in a rat model of prostatitis TNF levels were also increased in comparison to controls (Asakawa et al. (2001) *Hinyokika Kiyo*

47:459; Harris et al. (2000) *Prostate* 44:25). In one embodiment, the TNFα antibody of the invention is used to treat prostatitis.

The term "prostatitis" as used herein refers to an inflammation of the prostate. Prostatitis is also referred to as pelvic pain syndrome. Prostatitis manifests itself in a variety of forms, including nonbacterial prostatitis, acute prostatitis, bacterial prostatitis, and acute prostatitis. Acute prostatitis refers to an inflammation of the prostate gland that develops suddenly. Acute prostatitis is usually caused by a bacterial infection of the prostate gland. Chronic prostatitis is an inflammation of the prostate gland that develops gradually, continues for a prolonged period, and typically has subtle symptoms. Chronic prostatitis is also usually caused by a bacterial infection 4. Choroidal Neovascularization Tumor necrosis factor has been implicated in the pathophysiology of choroidal neovascularization. For example, in surgically excised choroidal neovascular membranes, neovascular vessels stained positive for both TNF and IL-1 (Oh H et al. (1999) *Invest Ophthalmol Vis Sci* 40:1891). In one embodiment, the TNFα antibody is used to treat choroidal neovascularization. The term "choroidal neovascularization" as used herein refers to the growth of new blood vessels that originate from the choroid through a break in the Bruch membrane into the sub-retinal pigment epithelium (sub-RPE) or subretinal space. Choroidal neovascularization (CNV) is a major cause of visual loss in patients with the condition.

5. Sciatica

Tumor necrosis factor has been implicated in the pathophysiology of sciatica (Ozaktay et al. (2002) *Eur Spine J.* 11:467; Brisby et al. (2002) *Eur Spine J.* 11:62). In one embodiment, the TNFα antibody of the invention is used to treat sciatica. The term "sciatica" as used herein refers to a condition involving impaired movement and/or sensation in the leg, caused by damage to the sciatic nerve. Sciatica is also commonly referred to as neuropathy of the sciatic nerve and sciatic nerve dysfunction. Sciatica is a form of peripheral neuropathy. It occurs when there is damage to the sciatic nerve, located in the back of the leg. The sciatic nerve controls the muscles of the back of the knee and lower leg and provides sensation to the back of the thigh, part of the lower leg and the sole of the foot. Sciatica can be indicative of another disorder, including a lumbar herniated disc, spinal stenosis, degenerative disc disease, isthmic spondyloisthesis and piniformis syndrome.

6. Sjogren's Syndrome

Tumor necrosis factor has been implicated in the pathophysiology of Sjogren's syndrome (Koski et al. (2001) *Clin Exp Rheumatol.* 19:131). In one embodiment, the TNFα antibody of the invention is used to treat Sjogren's syndrome. The term "Sjogren's syndrome" as used herein refers to a systemic inflammatory disorder characterized by dry mouth, decreased tearing, and other dry mucous membranes, and is often associated with autoimmune rheumatic disorders, such as rheumatoid arthritis. Dryness of the eyes and mouth are the most common symptoms of this syndrome. The symptoms may occur alone, or with symptoms associated with rheumatoid arthritis or other connective tissue diseases. There may be an associated enlargement of the salivary glands. Other organs may become affected. The syndrome may be associated with rheumatoid arthritis, systemic lupus erythematosus, scleroderma, polymyositis, and other diseases.

7. Uveitis

Tumor necrosis factor has been implicated in the pathophysiology of uveitis (Wakefield and Lloyd (1992) *Cytokine* 4:1; Woon et al. (1998) *Curr Eye Res.* 17:955). In one embodiment, the TNFα antibody of the invention is used to treat uveitis. The term "uveitis" as used herein refers to an inflammation of the the uvea, which is the layer between the sclera and the retina, which includes the iris, ciliary body, and the choroid. Uveitis is also commonly referred to as iritis, pars planitis, chroiditis, chorioretinitis, anterior uveitis, and posterior uveitis. The most common form of uveitis is anterior uveitis, which involves inflammation in the front part of the eye, which is usually isolated to the iris. This condition is often called iritis. In one embodiment, the term uveitis refers to an inflammation of the the uvea which excludes inflammation associated with an autoimmune disease, i.e., excludes autoimmune uveitis.

8. Wet Macular Degeneration

Tumor necrosis factor has been implicated in the pathophysiology of wet macular degeneration. In one embodiment, the TNFα antibody of the invention is used to treat wet macular degeneration. The term "wet macular degeneration" as used herein refers to a disorder that affects the macula (the central part of the retina of the eye) and causes decreased visual acuity and possible loss of central vision. Patients with wet macular degeneration develop new blood vessels under the retina, which causes hemorrhage, swelling, and scar tissue.

9. Osteoporosis

Tumor necrosis factor has been implicated in the pathophysiology of osteoporosis, (Tsutsumimoto et al. (1999) *J Bone Miner Res.* 14:1751). Osteoporosis is used to refer to a disorder characterized by the progressive loss of bone density and thinning of bone tissue. Osteoporosis occurs when the body fails to form enough new bone, or when too much old bone is reabsorbed by the body, or both. The TNFα antibody, or antigen-binding fragment thereof, of the invention can be used to treat osteoporosis.

10. Osteoarthritis

Tumor necrosis factor has been implicated in the pathophysiology of osteoarthritis, (Venn et al. (1993) *Arthritis Rheum.* 36:819; Westacott et al. (1994) *J Rheumatol.* 21:1710). Osteoarthritis (OA) is also referred to as hypertrophic osteoarthritis, osteoarthrosis, and degenerative joint disease. OA is a chronic degenerative disease of skeletal joints, which affects specific joints, commonly knees, hips, hand joints and spine, in adults of all ages. OA is characterized by a number of the following manifestations including degeneration and thinning of the articular cartilage with associated development of "ulcers" or craters, osteophyte formation, hypertrophy of bone at the margins, and changes in the snyovial membrane and enlargement of affected joints. Furthermore, osteoarthritis is accompanied by pain and stiffness, particularly after prolonged activity. The antibody, or antigen-binding fragment thereof, of the invention can be used to treat osteoarthritis. Characteristic radiographic features of osteoarthritis include joint space narrowing, subchondral sclerosis, osteophytosis, subchondral cyst formation, loose osseous body (or "joint mouse").

Medications used to treat osteoarthritis include a variety of nonsteroidal, anti-inflammatory drugs (NSAIDs). In addition, COX 2 inhibitors, including Celebrex, Vioxx, and Bextra, aand Etoricoxib, are also used to treat OA. Steroids, which are injected directly into the joint, may also be used to reduce inflammation and pain. In one embodiment of the invention, TNFα antibodies of the invention are administered in combination with a NSAIDs, a COX2 inhibitor, and/or steroids.

11. Other

The methods of the invention, also can be used to treat various other disorders in which TNFα activity is detrimental. Examples of other diseases and disorders in which TNFα activity has been implicated in the pathophysiology, and thus which can be treated using an antibody, or antibody portion, of the invention, include inflammatory bone disorders, bone resorption disease, coagulation disturbances, burns, reperfusion injury, keloid formation, scar tissue formation, pyrexia, periodontal disease, obesity, radiation toxicity, age-related cachexia, Alzheimer's disease, brain edema, inflammatory brain injury, cancer, chronic fatigue syndrome, dermatomyositis, drug reactions, such as Stevens-Johnson syndrome and Jarisch-Herxheimer reaction, edema in and/or around the spinal cord, familial periodic fevers, Felty's syndrome, fibrosis, glomerulonephritides (e.g. post-streptococcal glomerulonephritis or IgA nephropathy), loosening of prostheses, microscopic polyangiitis, mixed connective tissue disorder, multiple myeloma, cancer and cachexia, multiple organ disorder, myelo dysplastic syndrome, orchitism osteolysis, pancreatitis, including acute, chronic, and pancreatic abscess, polymyositis, progressive renal failure, pseudogout, pyoderma gangrenosum, relapsing polychondritis, rheumatic heart disease, sarcoidosis, sclerosing cholangitis, stroke, thoracoabdominal aortic aneurysm repair (TAAA), TNF receptor associated periodic syndrome (TRAPS), symptoms related to Yellow Fever vaccination, inflammatory diseases associated with the ear, chronic ear inflammation, chronic otitis media with or without cholesteatoma, pediatric ear inflammation, myotosis, ovarian cancer, colorectal cancer, therapy associated with induced inflammatory syndrome (e.g., syndromes following IL-2 administration), and a disorder associated with a reperfussion injury.

It is understood that all of the above-mentioned TNFα-related disorders include both the adult and juvenile forms of the disease where appropriate. It is also understood that all of the above-mentioned disorders include both chronic and acute forms of the disease. In addition, the multiple-variable dose methods of the invention can be used to treat each of the above-mentioned TNFα-related disorders alone or in combination with one another, e.g., a subject who is suffering from uveitis and lupus.

Additional Therapeutic Agents

The invention pertains to pharmaceutical compositions and methods of use thereof for the treatment of a TNFα-related disorder using a multiple-variable dose regimen. The pharmaceutical compositions comprise a first agent that prevents or inhibits a TNFα-related disorder. The pharmaceutical composition and methods of use may comprise a second agent that is an active pharmaceutical ingredient; that is, the second agent is therapeutic and its function is beyond that of an inactive ingredient, such as a pharmaceutical carrier, preservative, diluent, or buffer. The second agent may be useful in treating or preventing TNFα-related disorders. The second agent may diminish or treat at least one symptom(s) associated with the targeted disease. The first and second agents may exert their biological effects by similar or unrelated mechanisms of action; or either one or both of the first and second agents may exert their biological effects by a multiplicity of mechanisms of action. A pharmaceutical composition may also comprise a third compound, or even more yet, wherein the third (and fourth, etc.) compound has the same characteristics of a second agent.

It should be understood that the pharmaceutical compositions described herein may have the first and second, third, or additional agents in the same pharmaceutically acceptable carrier or in a different pharmaceutically acceptable carrier for each described embodiment. It further should be understood that the first, second, third and additional agent may be administered simultaneously or sequentially within described embodiments. Alternatively, a first and second agent may be administered simultaneously, and a third or additional agent may be administered before or after the first two agents.

The combination of agents used within the methods and pharmaceutical compositions described herein may have a therapeutic additive or synergistic effect on the condition(s) or disease(s) targeted for treatment. The combination of agents used within the methods or pharmaceutical compositions described herein also may reduce a detrimental effect associated with at least one of the agents when administered alone or without the other agent(s) of the particular pharmaceutical composition. For example, the toxicity of side effects of one agent may be attenuated by another agent of the composition, thus allowing a higher dosage, improving patient compliance, and improving therapeutic outcome. The additive or synergistic effects, benefits, and advantages of the compositions apply to classes of therapeutic agents, either structural or functional classes, or to individual compounds themselves.

Supplementary active compounds can also be incorporated into the compositions. In certain embodiments, an antibody or antibody portion of the invention is coformulated with and/or coadministered with one or more additional therapeutic agents that are useful for treating TNFα-related disorder in which TNFα activity is detrimental. For example, an anti-hTNFα antibody, antibody portion, or other TNFα inhibitor of the invention may be coformulated and/or coadministered with one or more additional antibodies that bind other targets (e.g., antibodies that bind other cytokines or that bind cell surface molecules), one or more cytokines, soluble TNFα receptor (see e.g., PCT Publication No. WO 94/06476) and/or one or more chemical agents that inhibit hTNFα production or activity (such as cyclohexane-ylidene derivatives as described in PCT Publication No. WO 93/19751). Furthermore, one or more antibodies or other TNFα inhibitors of the invention may be used in combination with two or more of the foregoing therapeutic agents. Such combination therapies may advantageously utilize lower dosages of the administered therapeutic agents, thus avoiding possible toxicities or complications associated with the various monotherapies. Specific therapeutic agent(s) are generally selected based on the particular TNFα-related disorder being treated, as discussed below.

Nonlimiting examples of therapeutic agents with which an antibody, antibody portion, or other TNFα inhibitor can be combined in a multiple variable dose method of treatment of the invention include the following: non-steroidal anti-inflammatory drug(s) (NSAIDs); cytokine suppressive anti-inflammatory drug(s) (CSAIDs); CDP-571/BAY-10-3356 (humanized anti-TNFα antibody; Celltech/Bayer); cA2/infliximab (chimeric anti-TNFα antibody; Centocor); 75 kdT-NFR-IgG/etanercept (75 kD TNF receptor-IgG fusion protein; Immunex; see e.g., *Arthritis & Rheumatism* (1994) Vol. 37, 5295; *J. Invest. Med.* (1996) Vol. 44, 235A); 55 kdTNF-IgG (55 kD TNF receptor-IgG fusion protein; Hoffmann-LaRoche); IDEC-CE9.1/SB 210396 (non-depleting primatized anti-CD4 antibody; IDEC/SmithKline; see e.g., *Arthritis & Rheumatism* (1995) Vol. 38, S185); DAB 486-IL-2 and/or DAB 389-IL-2 (IL-2 fusion proteins; Seragen; see e.g., *Arthritis & Rheumatism* (1993) Vol. 36, 1223); Anti-Tac (humanized anti-IL-2Rα; Protein Design Labs/Roche); IL-4 (anti-inflammatory cytokine; DNAX/Schering); IL-10 (SCH 52000; recombinant IL-10, anti-inflammatory cytokine; DNAX/Schering); IL-4; IL-10 and/or IL-4 agonists (e.g., agonist antibodies); IL-1RA (IL-1 receptor antagonist; Synergen/Amgen); anakinra (Kineret®/Amgen); TNF-bp/s-TNF (soluble TNF binding protein; see e.g., *Arthritis & Rheumatism* (1996) Vol. 39, No. 9 (supplement), S284; *Amer. J. Physiol.—Heart and Circulatory Physiology* (1995) Vol. 268, pp. 37-42); R973401 (phosphodiesterase Type IV inhibitor; see e.g., *Arthritis & Rheumatism* (1996) Vol. 39, No. 9 (supplement), S282); MK-966 (COX-2 Inhibitor; see e.g., *Arthritis & Rheumatism* (1996) Vol. 39, No. 9 (supplement), S81); Iloprost (see e.g., *Arthritis & Rheumatism* (1996) Vol. 39, No. 9 (supplement), S82); methotrexate; thalidomide (see e.g., *Arthritis & Rheumatism* (1996) Vol. 39, No. 9 (supplement), S282) and thalidomide-related drugs (e.g., Celgen); leflunomide (anti-inflammatory and cytokine inhibitor; see e.g., *Arthritis & Rheumatism* (1996) Vol. 39, No. 9 (supplement), S131; *Inflammation Research* (1996) Vol. 45, pp. 103-107); tranexamic acid (inhibitor of plasminogen activation; see e.g., *Arthritis & Rheumatism* (1996) Vol. 39, No. 9 (supplement), S284); T-614 (cytokine inhibitor; see e.g., *Arthritis & Rheumatism* (1996) Vol. 39, No. 9 (supplement), S282); prostaglandin E1 (see e.g., *Arthritis & Rheumatism* (1996) Vol. 39, No. 9 (supplement), S282); Tenidap (non-steroidal anti-inflammatory drug; see e.g., *Arthritis & Rheumatism* (1996) Vol. 39, No. 9 (supplement), S280); Naproxen (non-steroidal anti-inflammatory drug; see e.g., *Neuro Report* (1996) Vol. 7, pp. 1209-1213); Meloxicam (non-steroidal anti-inflammatory drug); Ibuprofen (non-steroidal anti-inflammatory drug); Piroxicam (non-steroidal anti-inflammatory drug); Diclofenac (non-steroidal anti-inflammatory drug); Indomethacin (non-steroidal anti-inflammatory drug); Sulfasalazine (see e.g., *Arthritis & Rheumatism* (1996) Vol. 39, No. 9 (supplement), S281); Azathioprine (see e.g., *Arthritis & Rheumatism* (1996) Vol. 39, No. 9 (supplement), S281); ICE inhibitor (inhibitor of the enzyme interleukin-1β converting enzyme); zap-70 and/or lck inhibitor (inhibitor of the tyrosine kinase zap-70 or lck); VEGF inhibitor and/or VEGF-R inhibitor (inhibitos of vascular endothelial cell growth factor or vascular endothelial cell growth factor receptor; inhibitors of angiogenesis); corticosteroid anti-inflammatory drugs (e.g., SB203580); TNF-convertase inhibitors; anti-IL-12 antibodies; anti-IL-18 antibodies; interleukin-11 (see e.g., *Arthritis & Rheumatism* (1996) Vol. 39, No. 9 (supplement), S296); interleukin-13 (see e.g., *Arthritis & Rheumatism* (1996) Vol. 39, No. 9 (supplement), S308); interleukin-17 inhibitors (see e.g., *Arthritis & Rheumatism* (1996) Vol. 39, No. 9 (supplement), S120); gold; penicillamine; chloroquine; hydroxychloroquine; chlorambucil; cyclosporine; cyclophosphamide; total lymphoid irradiation; anti-thymocyte globulin; anti-CD4 antibodies; CD5-toxins; orally-administered peptides and collagen; lobenzarit disodium; Cytokine Regulating Agents (CRAs) HP228 and HP466 (Houghten Pharmaceuticals, Inc.); ICAM-1 antisense phosphorothioate oligodeoxynucleotides (ISIS 2302; Isis Pharmaceuticals, Inc.); soluble complement receptor 1 (TP10; T Cell Sciences, Inc.); prednisone; orgotein; glycosaminoglycan polysulphate; minocycline; anti-IL2R antibodies; marine and botanical lipids (fish and plant seed fatty acids; see e.g., DeLuca et al. (1995) *Rheum. Dis. Clin. North Am.* 21:759-777); auranofin; phenylbutazone; meclofenamic acid; flufenamic acid; intravenous immune globulin; zileuton; azaribine; mycophenolic acid (RS-61443); tacrolimus (FK-506); sirolimus (rapamycin); amiprilose (therafectin); cladribine (2-chlorodeoxyadenosine); methotrexate; antivirals; and immune modulating agents. Any of the above-mentioned agents can be administered in combination with the TNFα antibody of the invention to treat an TNFα-related disorder using the multiple variable dose or single dose method of treatments of the invention.

In one embodiment, the TNFα antibody of the invention is administered in combination with one of the following agents for the treatment of rheumatoid arthritis using the multiple variable dose method of treatment of the invention: small molecule inhibitor of KDR (ABT-123), small molecule inhibitor of Tie-2; methotrexate; prednisone; celecoxib; folic acid; hydroxychloroquine sulfate; rofecoxib; etanercept; infliximab; anakinra (Kineret®/Amgen); leflunomide; naproxen; valdecoxib; sulfasalazine; ibuprofen; methylprednisolone; meloxicam; methylprednisolone acetate; gold sodium thiomalate; aspirin; azathioprine; triamcinolone acetonide; propxyphene napsylate/apap; folate; nabumetone; diclofenac; piroxicam; etodolac; diclofenac sodium; oxaprozin; oxycodone hcl; hydrocodone bitartrate/apap; diclofenac sodium/misoprostol; fentanyl; anakinra, human recombinant; tramadol hcl; salsalate; sulindac; cyanocobalamin/fa/pyridoxine; acetaminophen; alendronate sodium; prednisolone; morphine sulfate; lidocaine hydrochloride; indomethacin; glucosamine sulfate/chondroitin; cyclosporine; sulfadiazine; amitriptyline hcl; oxycodone hcl/acetaminophen; olopatadine hcl; misoprostol; naproxen sodium; omeprazole; mycophenolate mofetil; cyclophosphamide; rituximab; IL-1 TRAP; MRA; CTLA4-IG; IL-18 BP; ABT-874; ABT-325 (anti-IL 18); anti-IL 15; BIRB-796; SCIO-469; VX-702; AMG-548; VX-740; Roflumilast; IC-485; CDC-801; and mesopram. In another embodiment, the TNFα antibody of the invention is administered using a multiple-variable dose method for the treatment of a TNFα related disorder in combination with one of the above mentioned agents for the treatment of rheumatoid arthritis. In another embodiment, the above-mentioned additional agents are used in combination with a TNFα antibody in the single dose method of treatment of the invention.

In one embodiment, the TNFα antibody of the invention is administered using the multiple variable dose regimen in combination with one of the following agents for the treatment of a TNFα-related disorder in which TNFα activity is detrimental: anti-IL12 antibody (ABT 874); anti-IL18 antibody (ABT 325); small molecule inhibitor of LCK; small molecule inhibitor of COT; anti-IL1 antibody; small molecule inhibitor of MK2; anti-CD19 antibody; small molecule inhibitor of CXCR3; small molecule inhibitor of CCR5; small molecule inhibitor of CCR11 anti-E/L selectin antibody; small molecule inhibitor of P2X7; small molecule inhibitor of IRAK-4; small molecule agonist of glucocorticoid receptor; anti-05a receptor antibody; small molecule inhibitor of C5a receptor; anti-CD32 antibody; and CD32 as a therapeutic protein.

In yet another embodiment, a TNFα antibody obtained using the invention may be administered in combination with an antibiotic or antiinfective agent. Antiinfective agents include those agents known in the art to treat viral, fungal, parasitic or bacterial infections. The term, "antibiotic," as used herein, refers to a chemical substance that inhibits the growth of, or kills, microorganisms. Encompassed by this term are antibiotic produced by a microorganism, as well as synthetic antibiotics (e.g., analogs) known in the art. Antibiotics include, but are not limited to, clarithromycin (Biaxin®), ciprofloxacin (Cipro®), and metronidazole (Flagyl®).

In another embodiment, a TNFα antibody obtained using the invention may be administered with an additional therapeutic agent to treat sciatica or pain. Examples of agents which can be used to reduce or inhibit the symptoms of sciatica or pain include hydrocodone bitartrate/apap, rofecoxib, cyclobenzaprine hcl, methylprednisolone, naproxen, ibuprofen, oxycodone hcl/acetaminophen, celecoxib, valdecoxib, methylprednisolone acetate, prednisone, codeine phosphate/apap, tramadol hcl/acetaminophen, metaxalone, meloxicam, methocarbamol, lidocaine hydrochloride, diclofenac sodium, gabapentin, dexamethasone, carisoprodol, ketorolac tromethamine, indomethacin, acetaminophen, diazepam, nabumetone, oxycodone hcl, tizanidine hcl, diclofenac sodium/misoprostol, propoxyphene napsylate/apap, asa/oxycod/oxycodone ter, ibuprofen/hydrocodone bit, tramadol hcl, etodolac, propoxyphene hcl, amitriptyline hcl, carisoprodol/codeine phos/asa, morphine sulfate, multivitamins, naproxen sodium, orphenadrine citrate, and temazepam.

In yet another embodiment, the TNFα-related disorder is treated with a TNFα antibody obtained using the invention in combination with hemodialysis.

In another embodiment, a TNFα antibody obtained using the invention may be used in combination with a drug used to treat Crohn's disease or a Crohn's-related disorder in the multiple variable dose regimen of the invention. Examples of therapeutic agents which can be used to treat Crohn's include mesalamine, prednisone, azathioprine, mercaptopurine, infliximab, budesonide, sulfasalazine, methylprednisolone sod succ, diphenoxylate/atrop sulf, loperamide hydrochloride, methotrexate, omeprazole, folate, ciprofloxacin/dextrose-water, hydrocodone bitartrate/apap, tetracycline hydrochloride, fluocinonide, metronidazole, thimerosal/boric acid, hyoscyamine sulfate, cholestyramine/sucrose, ciprofloxacin hydrochloride, meperidine hydrochloride, midazolam hydrochloride, oxycodone hcl/acetaminophen, promethazine hydrochloride, sodium phosphate, sulfamethoxazole/trimethoprim, celecoxib, polycarbophil, propoxyphene napsylate, hydrocortisone, multivitamins, balsalazide disodium, codeine phosphate/apap, colesevelam hcl, cyanocobalamin, folic acid, levofloxacin, natalizumab, methylprednisolone, interferon-gamma, and sargramostim (GM-CSF). In one embodiment, methotrexate is administered for the treatment of Crohn's disease at a dose of 2.5 mg to 30 mg per week.

In another embodiment, a TNFα antibody is administered in combination with an additional therapeutic agent to treat asthma in the multiple variable dose regimen of the invention. Examples of agents which can be used to reduce or inhibit the symptoms of asthma include the following: albuterol; salmeterol/fluticasone; sodium; fluticasone propionate; budesonide; prednisone; salmeterol xinafoate; levalbuterol hcl; sulfate/ipratropium; prednisolone sodium phosphate; triamcinolone acetonide; beclomethasone dipropionate; ipratropium bromide; Azithromycin; pirbuterol acetate; prednisolone; theophylline anhydrous; zafirlukast; methylprednisolone sod succ; clarithromycin; formoterol fumarate; influenza virus vaccine; methylprednisolone; trihydrate; allergy injection; cromolyn sodium; cefprozil; fexofenadine hydrochloride; flunisolide/menthol; levofloxacin; amoxicillin/clavulanate, inhaler assist device, guaifenesin, dexamethasone sod phosphate; moxifloxacin hcl; hyclate; guaifenesin/d-methorphan; gatifloxacin; pephedrine/cod/chlorphenir; cetirizine hydrochloride; mometasone furoate; salmeterol xinafoate; benzonatate; cephalexin; pe/hydrocodone/chlorphenir; cetirizine hcl/pseudoephed; phenylephrine/cod/promethazine; codeine/promethazine; flunisolide; dexamethasone; guaifenesin/pseudoephedrine; chlorpheniramine/hydrocodone; nedocromil sodium; terbutaline sulfate; epinephrine and methylprednisolone, metaproterenol sulfate.

In another embodiment, the TNFα antibody of the invention is administered in combination with an additional therapeutic agent to treat COPD. Examples of agents which can be used to reduce or inhibit the symptoms of COPD include, albuterol sulfate/ipratropium; ipratropium bromide; salmeterol/fluticasone; albuterol; salmeterol; xinafoate; fluticasone propionate; prednisone; theophylline anhydrous; levofloxacin; methylprednisolone sod succ; montelukast sodium; budesonide; formoterol fumarate; triamcinolone acetonide; guaifenesin; azithromycin; beclomethasone; dipropionate; levalbuterol hcl; flunisolide; sodium; trihydrate; gatifloxacin; zafirlukast; furoate; amoxicillin/clavulanate; flunisolide/menthol; chlorpheniramine/hydrocodone; metaproterenol sulfate; methylprednisolone; ephedrine/cod/chlorphenir; pirbuterol acetate; -ephedrine/loratadine; terbutaline sulfate; tiotropium bromide;(R,R)-formoterol; TgAAT; Cilomilast and Roflumilast In another embodiment, the TNFα antibody of the invention is administered in combination with an additional therapeutic agent to treat IPF. Examples of agents which can be used to reduce or inhibit the symptoms of IPF include prednisone; azathioprine; albuterol; colchicines; sulfate; digoxin; gamma interferon; methylprednisolone sod succ; furosemide; lisinopril; nitroglycerin; spironolactone; cyclophosphamide; ipratropium bromide; actinomycin d; alteplase; fluticasone propionate; levofloxacin; metaproterenol sulfate; morphine sulfate; oxycodone hcl; potassium chloride; triamcinolone acetonide; tacrolimus anhydrous; calcium; interferon-alpha; methotrexate; mycophenolate mofetil.

In one embodiment of the invention, a TNFα antibody is administered in combination with an agent which is commonly used to treat spondyloarthropathies. Examples of such agents include nonsteroidal, anti-inflammatory drugs (NSAIDs), COX 2 inhibitors, including Celebrex®, Vioxx®, and Bextra®, aand etoricoxib. Physiotherapy is also commonly used to treat spondyloarthropathies, usually in conjunction with non-steoidal inflammatory drugs.

In another embodiment, the TNFα antibody of the invention may be administered in combination with an additional therapeutic agent to treat ankylosing spondylitis. Examples of agents which can be used to reduce or inhibit the symptoms of ankylosing spondylitis include ibuprofen, diclofenac and misoprostol, naproxen, meloxicam, indomethacin, diclofenac, celecoxib, rofecoxib, sulfasalazine, prednisone, methotrexate, azathioprine, minocyclin, prednisone, etanercept, and infliximab.

In another embodiment, the TNFα antibody of the invention is administered in combination with an additional therapeutic agent to treat psoriatic arthritis. Examples of agents which can be used to reduce or inhibit the symptoms of psoriatic arthritis include methotrexate; etanercept; rofecoxib; celecoxib; folic acid; sulfasalazine; naproxen; leflunomide; methylprednisolone acetate; indomethacin; hydroxychloroquine sulfate; sulindac; prednisone; betamethasone diprop augmented; infliximab; methotrexate; folate; triamcinolone acetonide; diclofenac; dimethylsulfoxide; piroxicam; diclofenac sodium; ketoprofen; meloxicam; prednisone; methylprednisolone; nabumetone; tolmetin sodium; calcipotriene; cyclosporine; diclofenac; sodium/misoprostol; fluocinonide; glucosamine sulfate; gold sodium thiomalate; hydrocodone; bitartrate/apap; ibuprofen; risedronate sodium; sulfadiazine; thioguanine; valdecoxib; alefacept; and efalizumab.

In one embodiment the TNFα inhibitor is administered following an initial procedure for treating coronary heart disease in the multiple variable dose regimen of the invention. Examples of such procedures include, but are not limited to coronary artery bypass grafting (CABG) and Percutaneous transluminal coronary balloon angioplasty (PTCA) or angioplasty. In one embodiment, the TNFα inhibitor is administered in order to prevent stenosis from re-occurring. In another embodiment of the invention, the TNFα inhibitor is administered in order to prevent or treat restenosis. The invention also provides a method of treatment, wherein the TNFα inhibitor is administered prior to, in conjunction with, or following the insertion of a stent in the artery of a subject receiving a procedure for treating coronary heart disease. In one embodiment the stent is administered following CABG or PTCA.

A wide variety of stent grafts may be utilized within the context of the present invention, depending on the site and nature of treatment desired. Stent grafts may be, for example, bifurcated or tube grafts, cylindrical or tapered, self-expandable or balloon-expandable, unibody, or, modular. Moreover, the stent graft may be adapted to release the drug at only the distal ends, or along the entire body of the stent graft. The TNFα inhibitor of the invention can also be administered on a stent. In one embodiment, the
TNFα antibody, including, for example, adalimumab/D2E7/HUMIRA® is administered by a drug-eluting stent.

The TNFα antibody can be administered in combination with an additional therapeutic agent to treat restenosis. Examples of agents which can be used to treat or prevent restenosis include sirolimus, paclitaxel, everolimus, tacrolimus, ABT-578, and acetaminophen.

The TNFα antibody of the invention can be administered in combination with an additional therapeutic agent to treat myocardial infarction. Examples of agents which can be used to treat or prevent myocardial infarction include aspirin, nitroglycerin, metoprolol tartrate, enoxaparin sodium, heparin sodium, clopidogrel bisulfate, carvedilol, atenolol, morphine sulfate, metoprolol succinate, warfarin sodium, lisinopril, isosorbide mononitrate, digoxin, furosemide, simvastatin, ramipril, tenecteplase, enalapril maleate, torsemide, retavase, losartan potassium, quinapril hcl/mag carb, bumetanide, alteplase, enalaprilat, amiodarone hydrochloride, tirofiban hcl m-hydrate, diltiazem hydrochloride, captopril, irbesartan, valsartan, propranolol hydrochloride, fosinopril sodium, lidocaine hydrochloride, eptifibatide, cefazolin sodium, atropine sulfate, aminocaproic acid, spironolactone, interferon, sotalol hydrochloride, potassium chloride, docusate sodium, dobutamine hcl, alprazolam, pravastatin sodium, atorvastatin calcium, midazolam hydrochloride, meperidine hydrochloride, isosorbide dinitrate, epinephrine, dopamine hydrochloride, bivalirudin, rosuvastatin, ezetimibe/simvastatin, avasimibe, abciximab, and cariporide.

The TNFα antibody of the invention can be administered in combination with an additional therapeutic agent to treat angina. Examples of agents which can be used to treat or prevent angina include: aspirin; nitroglycerin; isosorbide mononitrate; atenolol; metoprolol succinate; metoprolol tartrate; amlodipine besylate; digoxin; dilitiazem hydropchloride; isosorbide dinitrate; clopidogrel bisulfate; nifedipine; atorvastatin calcium; potassium chloride; simvastatin; verapamil hcl; furosemide; propranolol hcl; carvedilo; lisinopril; sprionolactone; hydrochlorothiazide; enalapril maleate; madolol; ramipril; enoxaparin sodium; heparin sodium; valsartan; sotalol hydrochloride; fenofibrate; ezetimibe; bumetanide; losartan potassium; lisinopril/hydrochlorothiazide; felodipine; captopril; and bisoprolol fumarate.

In one embodiment of the invention, a TNFα antibody is administered in combination with an agent which is commonly used to treat hepatitis C virus. Examples of such agents include Interferon-aplha-2a, Interferon-alpha-2b, Interferon-alpha con1, Interfero-aopha-n1, Pegylated interferon-alpha-2a, Pegylated interferon-alpha-2b, Ribavirin, Peginterferon alfa-2b and ribavirin, Ursodeoxycholic Acid, Glycyrrhizic Acid, Thymalfasin, Maxamine, and VX-497.

The TNFα antibody may be administered in combination with topical corticosteroids, vitamin D analogs, and topical or oral retinoids, or combinations thereof, for the treatment of psoriasis. In addition, the TNFα antibody may be administered in combination with one of the following agents for the treatment of psoriasis: small molecule inhibitor of KDR (ABT-123), small molecule inhibitor of Tie-2, calcipotriene, clobetasol propionate, triamcinolone acetonide, halobetasol propionate, tazarotene, methotrexate, fluocinonide, betamethasone diprop augmented, fluocinolone, acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, coal tar, diflorasone diacetate, etanercept, folate, lactic acid, methoxsalen, hc/bismuth subgal/znox/resor, methylprednisolone acetate, prednisone, sunscreen, salicylic acid, halcinonide, anthralin, clocortolone pivalate, coal extract, coal tar/salicylic acid, coal tar/salicylic acid/sulfur, desoximetasone, diazepam, emollient, pimecrolimus emollient, fluocinonide/emollient , mineral oil/castor oil/na lact, mineral oil/peanut oil, petroleum/isopropyl myristate, psoralen, salicylic acid, soap/tribromsalan, thimerosal/boric acid, celecoxib, infliximab, alefacept, efalizumab, tacrolimus, pimecrolimus, PUVA, UVB and other phototherapy, and sulfasalazine.

An antibody, antibody portion, may be used in combination with other agents to treat skin conditions. For example, an antibody, antibody portion, or other TNFα inhibitor of the invention is combined with PUVA therapy. PUVA is a combination of psoralen (P) and long-wave ultraviolet radiation (UVA) that is used to treat many different skin conditions. The antibodies, antibody portions, or other TNFα inhibitors of the invention can also be combined with pimecrolimus. In another embodiment, the antibodies of the invention are used to treat psoriasis, wherein the antibodies are administered in combination with tacrolimus. In a further embodiment, tacrolimus and TNFα inhibitors are administered in combination with methotrexate and/or cyclosporine. In still another embodiment, the TNFα inhibitor of the invention is administered with excimer laser treatment for treating psoriasis.

Nonlimiting examples of other therapeutic agents with which a TNFα antibody can be combined to treat a skin or nail disorder include UVA and UVB phototherapy. Other nonlimiting examples which can be used in combination with a TNFα inhibitor include anti-IL-12 and anti-IL-18 therapeutic agents, including antibodies.

In one embodiment, the TNFα antibody may be administered in combination with an additional therapeutic agent in the treatment of Behcet's disease. Additional therapeutic agents which can be used to treat Behcet's disease include, but are not limited to, prednisone, cyclophosphamide (Cytoxan), Azathioprine (also called imuran, methotrexate, timethoprim/sulfamethoxazole (also called bactrim or septra) and folic acid.

Any one of the above-mentioned therapeutic agents, alone or in combination therewith, can be administered to a subject suffering from a TNFα-related disorder in which TNFα is detrimental, in combination with the TNFα antibody using a multiple variable dose treatment regimen of the invention. In one embodiment, any one of the above-mentioned therapeutic agents, alone or in combination therewith, can be administered to a subject suffering from rheumatoid arthritis in addition to a TNFα antibody to treat a TNFα-related disorder. It should be understood that the additional therapeutic agents can be used in combination therapy as described above, but also may be used in other indications described herein wherein a beneficial effect is desired.

This invention is further illustrated by the following examples which should not be construed as limiting. The contents of all references, patents and published patent applications cited throughout this application are incorporated herein by reference

EXAMPLES

Example 1

Purification Procedure for Adalimumab

In this example, a purification process for purifying a mixture of adalimumab and host cell proteins (HCPs) was devised, which process is referred to as process A. In process A, the adalimumab-HCP mixture waas not subjected to a protein A chromatography step. The first column used in process A was a cation exchange resin, Fractogel S, to which adalimumab bound while HCP flowed through. Adalimumab was then eluated from the Fractogel S column in a first eluate. Next, the first eluate was subjected to pH viral inactivation to obtain a virally inactivated preparation. Next, the virally inactivated preparation was applied to an anion ion exchange resin, a Q sepharose column, to which adalimumab does not bind, to thereby obtain a first flow through. The first flow was then applied to a hydrophobic interaction column, a phenyl sepharose column, to which adalimumab binds and HCP flows through, to thereby obtain a second eluate. Further processing and packaging of the second eluate was performed to obtain the final bottled product.

In more detail, process A comprises the following steps:

Step 1: Fractogel S column, 100×20 cm (157 L), v=175 cm/hr, Load ≦30 g protein/L resin per cycle, equilibrated with 20 mM sodium phosphate, 25 mM sodium chloride. After loading of adalimumab, the column was washed once with equilibration buffer and eluted with an elution buffer comprising 20 mM sodium phosphate, 150 mM sodium chloride to obtain the first eluate;

Step 2: Delipid filtration;

Step 3: Ultrafiltration;

Step 4: pH inactivation at pH 3.5 for 1 hour; after inactivation was complete, pH was adjusted to 6.8 to 7.5, the filter train was washed with two volumes of 50 mM trolamine;

Step 5: Q Sepharose FF column, 60×30 cm (85L), v=150 cm/hr, Load 40 g protein/L resin per cycle, equilibrated an equilibration buffer comprising 25 mM trolamine, 40 mM sodium chloride, pH 7.6; flow through obtained;

Step 6: Phenyl Sepharose HP column, 80×15 cm (75 L), v=75 cm/hr (elute 37.5 cm/hr), Load 20-40 g protein/L resin per cycle, equilibrated with an equilibriation buffer comprising 20 mM sodium phosphate, 1.1 M $(NH_4)_2SO_4$, pH 7, washed once with equilibration buffer and eluted by performing a salt step-gradient to 11 mM sodium phosphate, 0.625 M $(NH_4)_2SO_4$, pH 7.0, to thereby obtain a second eluate, with fractionation of product peak if load ≦35 g protein/L resin;

Step 7: Viral filtration;

Step 8: Final Ultrafiltration/Diafiltration;

Step 9: Final Bottling.

Further details of process A are also described in Example 2 below.

Example 2

Purification of Adalimumab to Improve Yield and Decrease Impurities

Modifications were introduced to the capture and fine purification operations in the manufacturing process of the antibody adalimumab, namely process A described in Example 1 above. The modified process is referred to herein as "process B", and includes the following overall steps: The starting material was the mixture obtained from the fermentation process using the Chinese Hamster Ovary (CHO) cell expression system. The mixture was first separated using cation exchange chromatography, i.e., a Fractogel S column, where adalimumab was captured on the column (referred to as "capture"). The load on the Fractogel S column was increased due to displacement. An improved method of washing the Fractogel S column was used to decrease the amount of host cell protein (HCP). The Fractogel S column with bound adalimumab was washed with a plurality of washes, including an intermediate wash which was a higher conductivity wash comprising 45% elution buffer and 55% water for injection (WFI). Following capture and washing, adalimumab was eluted from the Fractogel S column and the eluate subjected to anion exchange chromatography, i.e., a Q Sepharose column. Prior to running the first adalimumab eluate over the anion exchange column, the eluate was virally inactivated using an improved method based on pH and conductivity. The adalimumab preparation was collected in the flow-through of the anion column, and was subsequently separated further according to hydrophobic interaction chromatography, i.e., phenyl sepharose column. The eluate from the phenyl sepharose column was the further processed for viral filtration, final ultrafiltration, and final bottling according to standard methods in the art.

Process B is an improved purification method for achieving an antibody preparation having a reduced level of HCP and procathepsin L. The processes described herein were performed using a 6000 L volume, however, it should be noted that the modifications described in process B may be used with any volume. A comparison between the modifications of process A versus process B is provided in Table 5 (modifications in process B are highlighted in bold):

TABLE 5

Comparison of process A and process B

| Unit operation | Process A | Process B |
| --- | --- | --- |
| Fractogel S column | 100 × 20 cm (157 L) | 100 × 20 cm (157 L) |
|  | v = 175 cm/hr | v = 175 cm/hr |
|  | Load ≦30 g protein/L per cycle | Load ≦35 g protein/L per cycle |
|  | Wash 1 = equilibration buffer | Wash 1 = equilibration buffer |
|  | Elution = elution buffer | Wash 2 = 45% elution buffer: 55% WFI |
|  |  | Elution = elution buffer |
| Delipid filtration | There are no changes to this processing step. | |
| Ultrafiltration | There are no changes to this processing step. | |

TABLE 5-continued

Comparison of process A and process B

| Unit operation | Process A | Process B |
|---|---|---|
| pH Inactivation | After inactivation complete, adjust pH to 6.8-7.5 Wash filter train with 2 volumes of 50 mM trolamine | After inactivation complete, adjust pH to 7.8-8.2 Wash filter train with approximately 2.5 volumes of WFI to achieve conductivity in the range of 3.9-5.2 mS/cm |
| Q Sepharose FF column | 60 × 30 cm (85 L) v = 150 cm/hr Load ≦40 g protein/L resin per cycle | 60 × 30 cm (85 L) v = 150 cm/hr Load ≦40 g protein/L resin per cycle |
| Phenyl Sepharose HP column | 80 × 15 cm (75 L) v = 75 cm/hr (elute 37.5 cm/hr) Load 20-40 g protein/L resin per cycle with fractionation of product peak if load ≦35 g/L resin | 80 × 15 cm (75 L) v = 75 cm/hr (elute 37.5 cm/hr) Load 20-40 g protein/L resin per cycle with no fractionation of product peak if load ≦35 g/L resin |
| Viral Filtration | There are no changes to this processing step. | |
| Final ultrafiltration/ diafiltration | There are no changes to this processing step. | |
| Final bottling | There are no changes to this processing step. | |

The modifications to the various steps in process B are described in more detail below:

Cation Chromatography

The primary recovery and capture operations of process B comprise depth filtration, Fractogel $SO_3^-$ cation exchange chromatography (Fractogel S), the latter of which serves to capture adalimumab from the clarified harvest and reduce process-related impurities (e.g., CHO host cell and medium impurities). A 100 cm diameter×20 cm long column (bed volume 157 L) was used for this operation. The column was packed with Fractogel S resin (EM Industries, Hawthorne, N.Y.) and the asymmetry and Height of an Equivalent Theoretical Plate (HETP) are measured to determine the quality of the packing. The column was then sanitized with 1.0 M NaOH for 1 hour, and stored in 0.1 M NaOH until ready for use.

Cation exchange chromatography can be affected by protein loading, ionic strength (controlled by filtered harvest dilution), pH and linear velocity. Protein loading can affect selectivity, resolution (purity) and yield. Ionic strength (controlled by load dilution) and pH of the load sample can affect binding capacity, selectivity, resolution and yield. Linear velocity may affect mass transport properties, potentially resulting in decreased binding and resolution at very high flow rates and axial dispersion at very low flow rates.

The maximum load to the Fractogel S column was increased to 35 g protein per liter resin. The cation column was equilibrated with 20 mM sodium phosphate, 25 mM NaCl, pH 7. Following equilibration, the column is loaded with ≦35 g protein/L resin of diluted depth filtrate. One part depth filtrate was diluted with approximately 1.3 parts of water to reduce the conductivity to approximately 6.1 mS/cm. The column was then washed to baseline with equilibration buffer followed by a wash with 9 mM sodium phosphate, 68 mM NaCl, pH 7 (equivalent to 45% elution buffer, 55% WFI). The product was eluted from the column in a single fraction with 20 mM sodium phosphate, 150 mM NaCl, pH 7 (elution buffer). The product pool is collected from 10% full-scale deflection of the product peak $A_{280}$ on both the leading and trailing edges. The column was cycled as necessary to process the crude adalimumab. The Fractogel S eluates from each column cycle were pooled into the same collection tank. Between each cycle, the column was regenerated with 25 mM sodium phosphate, 1.0 M NaCl, pH 7.

Studies performed at laboratory scale demonstrated that efficient recovery of product and reduction in HCP can be achieved at higher load ranges than the previously established Acceptable Operating Range (AOR) of 15 to 30 g protein/L resin. Analysis of adalimumab breakthrough versus column load indicates that the calculated 5% breakthrough occurs at 38 g/L resin at pH 7. Therefore, a revised AOR of ≦35 g protein/L resin was established for the Fractogel S chromatography step. In sum, the load limit was also increased to 35 grams protein per liter of resin to increase process capacity.

In another set of experiments with the Fractogel resin, the effect of pH on adalimumab breakthrough versus column load was examined. In particular, a product breakthrough curve was used to determine the resin dynamic binding capacity under defined loading conditions. Table 6 below summarizes the recovery data for the Fractogel loading capacity study at the previously described pH 7 conditions. Recovery percentage at 10 g/L was normalized to 100%.

TABLE 6

Recovery data for Fractogel loading capacity study at pH 7

| Loading capacity (g/L) | AYF16G recovery (%) | AYF17G recovery (%) | Average recovery (%) |
|---|---|---|---|
| 10 | 100 | 100 | 100 |
| 15 | 99 | 99 | 99 |
| 20 | 98 | 98 | 98 |
| 25 | 99 | 97 | 98 |
| 30 | 98 | 96 | 97 |
| 40 | 95 | 95 | 95 |
| 50 | 93 | 88 | 91 |

Fractogel step yield ≧50%, BR-068.

The results at pH 7 show greater than 90% adalimumab recovery was observed for loading conditions of less than 50 g adalimumab per liter of Fractogel resin. The adalimumab breakthough was plotted versus loading capacity to generate a theoretical breakthrough curve. At pH 7, the theoretical 10% breakthrough was found to be at 54 g adalimumab per liter of Fractogel resin. Also at pH7, the theoretical 5% breakthrough was found to be at 38 g adalimumab per liter of Fractogel resin, confirming the results described above.

A similar study was carried out as described above except that the load and the first wash pH conditions were adjusted to pH 5. The cation column was equilibrated with 24 mM citric acid and 51 mM sodium phosphate, dibasic, pH 5. Following equilibration, the column was loaded with up to 80 g protein/L resin of diluted depth filtrate. The cell culture harvest was pH adjusted to 5.0 with 3M acetic acid prior to the depth filtration. One part depth filtrate was diluted with approximately the same volume of water to reduce the conductivity to approximately 8 to 10 mS/cm. Again, the adalimumab breakthough was plotted versus loading capacity to generate a theoretical breakthrough curve. Under the studied conditions, the theoretical 10% breakthrough was found to be at approximately 74 g adalimumab per liter of Fractogel resin. The theoretical 5% breakthrough was found to be at approximately 73 g adalimumab per liter of Fractogel resin. Due to the character of the cation exchange of the resin, lowering the pH of the chromatography conditions significantly increased adalimumab dynamic binding capacity. Comparing the breakthrough curves at pH 5 and pH 7, the binding between adalimumab molecule and the Fractogel resin was observed to be much stronger at lower pH. It was also found that with the higher loading dynamic capacity at pH 5, better HCP clearance was achieved. Table 7 below summarizes the data for the Fractogel loading capacity study vs. the HCP present in the eluate at the newly tested pH 5 conditions. The data clearly indicate that under the tested conditions, HCP displacement by adalimumab had occurred.

TABLE 7

HCP Present in Fractogel Eluate at Different Loading Capacities at pH 5

| Loading capacity (g/L) | HCP (ng HCP/mg adalimumab) |
|---|---|
| 15 | 6102 |
| 20 | 6782 |
| 25 | 5767 |
| 30 | 5167 |
| 40 | 3983 |
| 60 | 3207 |

Since the analysis of adalimumab breakthrough versus column load at pH 5 indicated that the calculated 5% breakthrough occurs at 73 g/L resin, a revised AOR of ≦70 g protein/L resin can be established for the Fractogel S chromatography step at pH 5. In sum, the load limit, which previously was increased to 35 grams protein per liter of resin at pH 7 (as described above), can be further increased to 70 grams protein per liter of resin by lowering of the pH to 5.

Intermediate Wash

To further reduce the amount of impurities in the adalimumab preparation, an intermediate wash step was performed prior to adalimumab elution from the cation column (see Table 8 below). This additional wash was adjusted relative to the conductivity of the elution buffer, and helped to improve clearance of HCPs. The insertion of an intermediate wash step prior to elution reduced the amount of HCP eluted with adalimumab by over 60% compared to process A. Parameters investigated included the blend of elution buffer with water used in the wash (% elution buffer), conductivity, pH, wash volume, flow rate and resin age. The optimum wash consists of a blend of 45% elution buffer (20 mM sodium phosphate, 150 mM sodium chloride, pH 7) and 55% water. Table 8 presents data comparing the level of HCP in the Fractogel S eluate with and without the additional wash. Fractogel S eluate samples were assayed for HCP and compared with HCP levels in the eluate from a pilot-scale Fractogel S process, which incorporated a higher load and the wash step. The pilot-scale data indicates that the addition of the second wash step significantly improves the clearance of HCP by the Fractogel S step.

TABLE 8

HCP levels in Fractogel S eluate with and without pre-elution wash step at laboratory scale

| Sample | Column Load g protein/L resin | Step yield (%) | HCP (ng/mg adalimumab) |
|---|---|---|---|
| Lot A no $2^{nd}$ wash[a] | 25 | 96 | 19410 |
| Lot B no $2^{nd}$ wash[a] | 25 | 96 | 22992 |
| Lot C no $2^{nd}$ wash[a] | 25 | 93 | 21931 |
| Lot D no $2^{nd}$ wash[a] | 25 | 97 | 20037 |
| 6000 L load[b], pilot-scale[c] with $2^{nd}$ wash step | 30 | 95 | 4914 |

[a]Fractogel S eluate sample was taken from the indicated 6000 L lot and analyzed for HCP content
[b]Load consisted of a blend of filtered harvest from various lots
[c]Pilot-scale column size is 10 (D) × 21 (L) cm; $2^{nd}$ wash buffer: 45% elution buffer (20 mM sodium phosphate, 150 mM sodium chloride, pH 7.2), 55% water for injection.

Typical elution profiles for the Fractogel S chromatography step for each process are provided in FIG. 1. Process B includes the above-mentioned intermediate additional wash step prior to elution, thus the leading edge of the elution peak is sharper with less early-eluting species detected than that of the previous process. In sum, an intermediate wash step, just prior to the elution of adalimumab, was introduced to the Fractogel S step to improve clearance of process-related impurities, such as HCPs.

Viral Inactivation

The low pH inactivation step of process B provides a margin of safety by inactivating potential undetected enveloped viruses that may be present in the delipid filtrate. The viral-inactivated pool is subsequently pH-neutralized and filtered to remove particulates and minimize bioburden. The quality of the adalimumab during low pH virus inactivation may be affected by pH and the duration of the low pH incubation. Virus inactivation is dependent on these same parameters, and it may be affected by the protein concentration, which may reduce inactivation at high concentrations. The minimum incubation time at low pH was increased from 15 minutes to 60 minutes. Analysis of manufacturing samples taken before and after the low pH step confirmed that adalimumab can be safely held at pH 3.5 for 1 hour without compromising its ability to protect murine L929 cells against the cytotoxic effects of tumor necrosis factor (TNF).

Following inactivation, the pH and conductivity of the viral-inactivated eluate were adjusted in accordance with the equilibration buffer of the following column, e.g., Q Sepharose column The pH was adjusted to 7.8-8.2, with a target pH of 8.0. In sum, the pH and conductivity of the viral-inactivated pool, which serves as the Q Sepharose FF load, was adjusted to match to the pH and conductivity of the Q Sepharose equilibration buffer.

Anion Chromatography

The anionic column, i.e., Q Sepharose, step serves to reduce process-related impurities such as HCP, specifically including procathepsin L, as well as DNA and insulin. A 60 cm diameter×30 cm long column (bed volume 85 L) was used for Q Sepharose FF chromatography. The column was packed with Q Sepharose FF resin (Amersham Pharmacia, Piscataway, N.J.) and asymmetry and HETP were measured to determine the quality of the packing. The column was then sanitized with 1.0 M NaOH for 1 hour, and stored in 25 mM sodium phosphate, 20% isopropanol until ready for use.

Equilibration of the resin was accomplished with 25 mM trolamine, 40 mM NaCl, pH 8 (equilibration buffer). The maximum protein loading for this step was ≦40 g protein/L of resin per cycle. Process-related impurities adsorbed to the resin, and adalimumab flowed through the column. The diluted, filtered, virus-inactivated material was typically processed in two cycles of approximately equal amounts; additional cycles may be required to process all available material. Loading and elution were performed at 150 cm/hr, and the column flow-through is collected when the $A_{280}$ rises above 2% full scale. The column was then washed with equilibration buffer and the wash was collected until the $A_{280}$ returns to 5% full scale. The wash is pooled with the flow-through and is designated Q Sepharose FTW. Between cycles, the column was regenerated with 25 mM sodium phosphate, 1.0 M NaCl, pH 7, and then equilibrated with equilibration buffer.

Anion exchange chromatography operated in flow-through mode can be affected by protein loading, ionic strength (conductivity, which may be controlled by dilution of the low pH inactivation filtrate), pH and linear velocity. Protein loading can affect selectivity and yield. Ionic strength and pH of the load sample can affect binding capacity and selectivity. Linear velocity may affect mass transport properties, potentially resulting in decreased binding of process related impurities at very high flow rates and axial dispersion at very low flow rates. New load conductivity and pH ranges have been established based on laboratory studies Laboratory studies indicated that reduction of HCP by the Q Sepharose FF step could be enhanced by alterations to the loading conditions. Parameters investigated included the load pH, conductivity and grams of protein loaded per L of resin. Adjustment of the load conductivity and pH to match that of the column equilibration buffer (5 mS/cm, pH 8), and limiting the load 40 g adalimumab/L resin result in improved clearance of HCP and procathepsin L. Table 9 presents laboratory-scale data showing the reduction in HCP under process A (pH 7.7, conductivity 6.65 mS/cm) and the improved process conditions of pH 8 and conductivity of 5 mS/cm of process B. Limiting the load on the Q Sepharose column to 40 g/L of resin provides a four-fold improvement in clearance of HCP and the additional modifications to the pH and conductivity of the load yield a three-fold further improvement in HCP reduction.

Hydrophobic Interaction Chromatography

The objective of the Phenyl Sepharose HP chromatography column was to further reduce process-related and product-related impurities such as host cell proteins and aggregates, respectively. An 80 cm diameter×15 cm long column (bed volume 75 L) was used for this operation. The column was packed with Phenyl Sepharose HP resin (Amersham Pharmacia, Piscataway, N.J.) and asymmetry and HETP were measured to determine the quality of the packing. The column was then sanitized with 1.0 M NaOH for 1 hour, and stored in 25 mM Na Phosphate, 20% isopropanol until ready for use.

Equilibration of the resin was accomplished with 20 mM sodium phosphate, 1.1 M $(NH_4)_2SO_4$, pH 7.0 (equilibration buffer). The protein loading for this step was 20 to 40 g protein per L of resin, and two or three chromatography cycles were required to process the entire quantity of available material. The column operated at a linear velocity of 75 cm/hr. The Q Sepharose flowthrough was diluted with an equal volume of 40 mM sodium phosphate, 2.2 M $(NH_4)_2SO_4$, pH 7.0. Following loading the column was washed with 20 mM sodium phosphate, 1.1 M $(NH_4)_2SO_4$, pH 7.0. The product was eluted by performing a salt step-gradient to 11 mM sodium phosphate, 0.625 M $(NH_4)_2SO_4$, pH 7.0. Product was collected as the absorbance rises above 50% UV full scale and continued until absorbance decreases to less than 20% UV full scale as the peak tails.

The process modifications to the Fractogel S and Q Sepharose FF chromatography steps significantly reduced the burden of process-related impurity reduction placed upon the Phenyl Sepharose HP step. As a consequence of the changes, the major function of the Phenyl Sepharose HP step was the removal of adalimumab aggregates.

Process A required that at column loads of 35 g protein/L resin or higher, product was collected as the UV absorbance rises above 50% full scale deflection and continues until absorbance decreases to <20% full scale. At column loadings below 35 g protein/L resin, the first 0.15 column volume of the eluate peak was excluded from the collected pool to improve HCP clearance at this step. The incorporation of the modifications at the previous chromatography steps in process B alleviated the need for the peak exclusion at loads below 35 g protein/L resin since the incoming HCP load was significantly reduced. The reduction in the HCP load allowed expansion of the load range without fractionation. The effect

TABLE 9

HCP reduction under varying Q Sepharose FF load conditions

| Load amount G protein/L resin | Load conditions | Load HCP (ng/mg adalimumab) | Flow-through HCP (ng/mg adalimumab) | Fold reduction in HCP |
|---|---|---|---|---|
| 80 | pH 7.7, 6.65 mS/cm | 726 | 452 | 1.6 |
| 40 | pH 7.7, 6.65 mS/cm | 726 | 114 | 6.4 |
| 40 | pH 8.1, 5.08 mS/cm | 726 | 37.6 | 19.3 |

The HCP-reduced flowthrough comprising adalimumab obtained from the ion exchange column was subsequently used in hydrophobic interaction chromatography.

of this change permits processing of all material from each fermentation by the recovery process without Phenyl Sepharose HP peak cutting The linear flow rate for Phenyl Sepharose operation was investigated at laboratory scale. The adalimumab load was held constant and flow rates of 25 to 125 cm/hr were examined. The flow rate did affect product recovery but had no impact on product quality as assessed by SEC (% monomer) and clearance of HCP (Table 10), justifying the broader range of 25 to 125 cm/hr. The target flow rates for the Phenyl Sepharose manufacturing operation remain as previously established at 75 cm/hr and 37.5 cm/hr for the elution phase.

TABLE 10

Phenyl sepharose flow rate evaluation

| Flow rate (cm/hr) | Load (g protein/L resin) | % Recovery[a] | % Monomer[b] | % HCP clearance |
|---|---|---|---|---|
| 25 | 32.5 | 69 | 99.98 | 92.1 |
| 75 | 32.5 | 84 | 99.98 | 92.2 |
| 125 | 32.5 | 84 | 99.98 | 91.8 |

[a]Phenyl Sepharose step yield action limit: ≧48%
[b]Phenyl Sepharose step SEC action limit: ≧98% monomer The acceptable operating ranges for Phenyl Sepharose HP chromatography were investigated. Hydrophobic interaction chromatography can be affected by protein loading, ionic strength (conductivity), and linear velocity. Protein loading can affect selectivity and yield. Ionic strength of the load sample can affect binding capacity, selectivity and resolution. Linear velocity may affect mass transport properties, potentially resulting in decreased resolution of process related impurities at very high flow rates and axial dispersion at very low flow rates. The linear flow rate range is expanded to 25 to 125 cm/hr. The other acceptable operating ranges for Phenyl Sepharose chromatography are unchanged from those previously established for the 6000 L process and are listed in Table 10.

Comparable performance of the fine purification operations in both processes was demonstrated. Changes introduced as part of improved process B include: adjustment of the pH and conductivity of the viral-inactivated pool, which serves as the Q Sepharose FF load, to match the Q Sepharose equilibration buffer, limiting the Q Sepharose load to less than 40 g protein per liter resin, and elimination of the requirement to fractionate the Phenyl Sepharose eluate at loads of less than 35 g protein per liter resin. The quality of intermediates, as determined by SEC and WCX-10 assays, were comparable between the two processes.

Figure 3A:
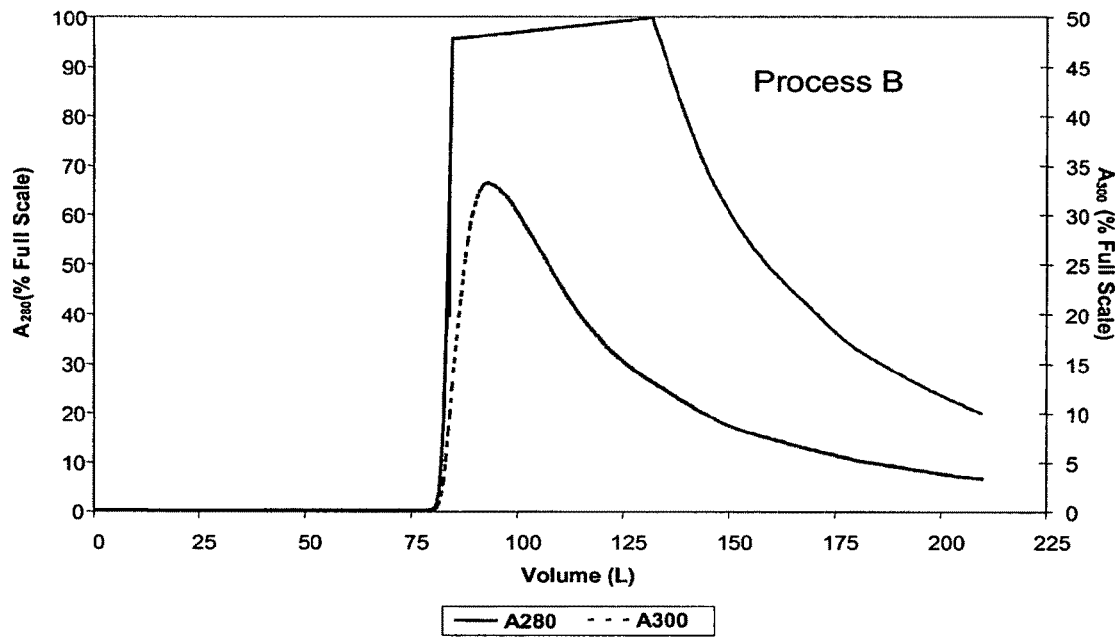
FIGS. 3A and 3B show a comparison of the elution profile of Phenyl Sepharose HP chromatography step, including process B (FIG. 3A) and process A (FIG. 3B).
Figure 3B:
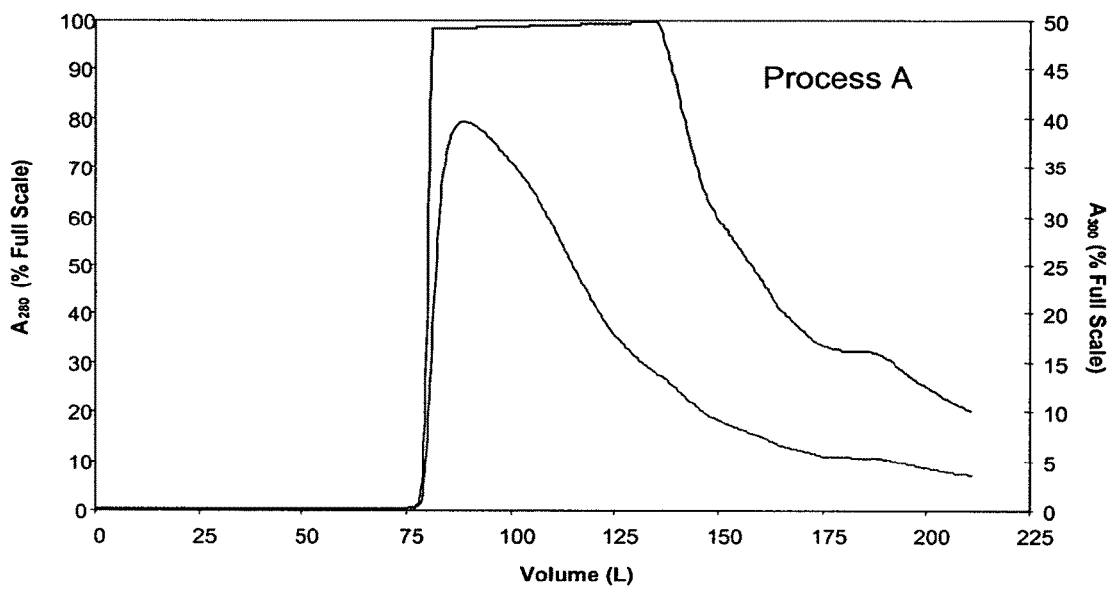

Typical elution profiles for the Q Sepharose FF and Phenyl Sepharose HP chromatography steps for each process are provided in FIGS. 2 and 3, respectively. The Q Sepharose flow-through comprising adalimumab and was collected. The load volume amounts for process B were higher than the previous process, due to the greater loads at the previous chromatography step (Fractogel S) and increased dilution volume; therefore the total flow-through volume is correspondingly greater.

In sum, a requirement to fractionate the Phenyl Sepharose eluate for loads less than 35 g protein per liter resin was eliminated due to improvements in impurity clearance resulting from the changes in the Fractogel S and Q Sepharose operations. In addition, the linear flow rate range was expanded to 25 to 125 cm/hr.

Reduction in HCP

Process B included modifications to the Fractogel S and Q Sepharose chromatography steps which were implemented to improve control of process-related impurities such as host cell protein (HCP) and, specifically, procathepsin L. A study was undertaken to assess the impact of process B on the removal of these impurities. The capacity of the Fractogel S, Q Sepharose FF and Phenyl Sepharose HP columns to remove CHO host cell proteins was evaluated at manufacturing scale. Host cell protein levels were determined by HCP ELISA (see Example 3) and data are expressed in ng HCP/mg adalimumab.

Representative samples were taken during process B and assayed for HCP. The results are presented in Table 11. Changes to the chromatography steps represent more rigorous chromatographic conditions which would be expected to improve the HCP clearance. Delipid filtration results reported are those from process A. The delipid filtration step was unchanged process B, therefore the HCP reduction factor achieved at this step is included in the overall performance of process B. On average, process B is able to remove greater than 4.35 $\log_{10}$ of HCP. Both Fractogel S chromatography and Q Sepharose FF chromatography cleared more than 1 $\log_{10}$ HCP, and the depth filtration step also cleared more then 1 $\log_{10}$. Additional HCP was removed by the Phenyl Sepharose column, however, the clearance value was not calculable because both the load and eluate HCP levels were below the level of quantitation. The drug substance produced by process B exhibited HCP levels below the limit of quantitation (LOQ) for the three validation lots.

TABLE 11

Host cell protein clearance

| Chromatography step | HCP in (ng/mg ada) | HCP out (ng/mg ada) | $\log_{10}$ reduction factor |
|---|---|---|---|
| Fractogel SO$_3$-column (average)[a] | | | 1.71 |
| Lot D | 1,035,101 | 18,199 | 1.75 |
| Lot E | 747,748 | 16,079 | 1.67 |
| Lot F | 1,350,632 | 26,772 | 1.70 |
| Delipid Filtration (average)[b] | | | 1.58 |
| Lot | 18,174 | 1,466 | 1.11 |
| Lot H | 34,369 | 805 | 1.63 |
| Lot I | 38,453 | 570 | 1.83 |
| Lot J | 25,774 | 466 | 1.74 |
| Q Seph. FF column (average)[a] | | | 1.07 |
| Lot D | 269.98 | Cycle A:28.41 | 0.98 |
| | | Cycle B:30.54 | 0.95 |
| Lot E | 313.44 | Cycle A:28.94 | 1.03 |
| | | Cycle B:29.82 | 1.02 |
| Lot F | 391.96 | Cycle A:22.51 | 1.24 |
| | | Cycle B:26.52 | 1.17 |
| Phenyl Seph. HP column (average)[a] | | | N/A |
| Lot D | <40.44 | <9.08 | N/A |
| Lot E | <43.56 | <8.65 | N/A |
| Lot F | <44.65 | <9.22 | N/A |
| Total Clearance[c] | | | 4.35 |

[a]Data from process B
[b]Data from process A
[c]Log 10 reduction factors less than 1 are not included in the overall clearance calculation Overall improvements in HCP and procathepsin L levels are also shown in Tables 12 and 13, respectively, where process B showed significant decreases in both levels in comparison to process A.

Procathepsin L Process Mapping

Process intermediate samples were taken at several steps and analyzed for fluorescence generated by activation of procathepsin L to cathepsin L. Results are shown in Table 14 below for process B and process A samples. The Fractogel S load and Phenyl Sepharose load and eluate samples could not be evaluated due to interference with the method. The Q Sepharose FF chromatography step has the capability of removing greater than 90% of the detectable enzyme in the load. The Q Sepharose flow-through and wash (FTW) from the improved process contains approximately 50% less activatable procathepsin L than the Q Sepharose FTW from the 6000 L previous process. Reductions also occur between the Fractogel S and the Q Sepharose steps during which the delipid filtration, concentration by ultrafiltration, low pH viral inactivation and depth filtration operations are performed.

TABLE 14

Procathepsin L mapping of the process A and process B

Process B (RFU/s/mg)

| Sample | Lot S | Lot U | Lot T | Average ± SD | Reduction Factor[a] |
|---|---|---|---|---|---|
| Fractogel Eluate Pool | 46 | 59 | 57 | 54 ± 7 | N/A |
| Q Sepharose load | 32 | 31 | 39 | 34 ± 4 | 1.6 |
| Q Sepharose FTW | 2.2 | 3.6 | 2.3 | 2.7 ± 0.8 | 13.4 |
| Drug substance | 2.6 | 3.0 | 2.7 | 2.8 ± 0.2 | None |

Process A

| | Lot V | Lot W | Lot X | Average ± SD | Reduction Factor |
|---|---|---|---|---|---|
| Fractogel Eluate Pool | 96 | 83 | 96 | 91 ± 7 | N/A |
| Q Sepharose load | 46 | 67 | 58 | 57 ± 10 | 1.6 |
| Q Sepharose FTW | 5.8 | 5.7 | 5.0 | 5.5 ± 0.5 | 10.5 |
| Drug substance | 4.2 | 3.9 | 3.8 | 4.0 ± 0.2 | 1.4 |

[a]The reduction factor is calculated using pre-rounded data for each lot and the average of the three runs is reported.

Figure 4:
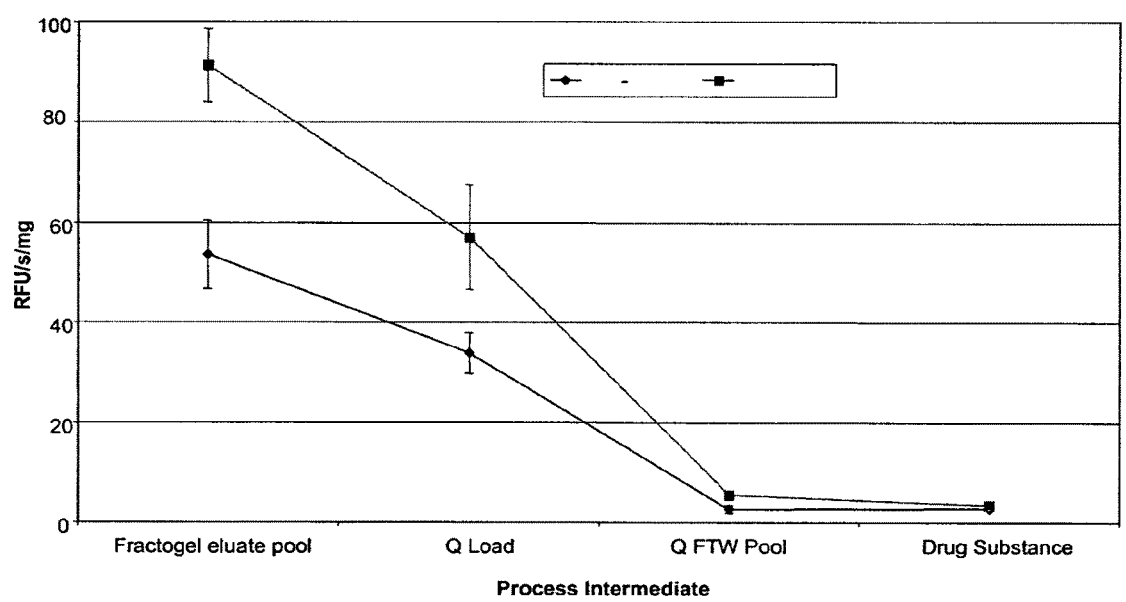
FIG. 4 shows a graphic depiction of a stepwise reduction in procathepsin L for the average process B (diamond shape) and average process A (square shape).

The comparison of procathepsin L reduction in processes A and B is displayed in FIG. 4. Process B exhibits lower procathepsin L levels than process A at each intermediate step, indicating that the modifications to the Fractogel S and Q Sepharose chromatography steps improve process performance with respect to removal of this impurity.

HCP Process Mapping

Process intermediate samples were collected from both processes A and B, and analyzed for HCP content. This study was performed in order to directly compare the two processes for HCP reduction. The results of the HCP analysis are shown in Table 15. Significant removal of HCP occurs at the Fractogel S and Q Sepharose steps in both processes but process B exhibits improved HCP clearance across both of these steps. The improved Fractogel S step, which includes the second wash step prior to product elution, has a reduction factor of 96 (1.96 $\log_{10}$) whereas the same step in the previous process yields a reduction factor of 48 (1.67 $\log_{10}$). Both processes exhibit a reduction factor of 50 accomplished by the delipid filtration, performed between the Fractogel S and Q Sepharose chromatography steps. The Q Sepharose operation in process B is performed with the load adjusted to the pH and conductivity of the column equilibration buffer. The HCP reduction factor achieved by the improved Q Sepharose step is four-fold greater than that demonstrated by the previous process (21 vs. 5). Further reduction occurs across the Phenyl Sepharose step such that the level of HCP is below the level of quantitation in the improved process UF/DF pool and drug substance; the previous drug substance samples exhibit very low but measurable levels of HCP.

TABLE 15

Host cell protein mapping of processes A and B

Process B lots (ng HCP/mg adalimumab)

| Sample | Lot D | Lot E | Lot F | Average ± SD | Reduction Factor |
|---|---|---|---|---|---|
| Filtered Harvest | 1,330,000 | 813,000 | 2,130,000 | 1,420,000 ± 661,000 | N/A |
| Fractogel Eluate Pool | 12,400 | 19,200 | 15,300 | 15,600 ± 3370 | 96 |
| Q Sepharose load | 554 | 220 | 371 | 382 ± 167 | 50 |
| Q Sepharose FTW | 18.5 | 20 | 17 | 18.5 ± 1.5 | 21 |
| Drug substance[a] | <5 | <5 | <5 | <5 | >4 |

Process A lots (ng HCP/mg adalimumab)

| | Lot V | Lot W | Lot X | Average ± SD | Reduction Factor |
|---|---|---|---|---|---|
| Filtered Harvest | 2,030,000 | 2,520,000 | 1,870,000 | 2,140,000 ± 339,000 | N/A |
| Fractogel Eluate Pool | 40,400 | 40,700 | 56,400 | 45,800 ± 9160 | 48 |
| Q Sepharose load | 536 | 1347 | 1248 | 1040 ± 442 | 50 |
| Q Sepharose FTW | 98 | 213 | 283 | 198 ± 93 | 5 |
| Drug substance | 5 | 8 | 11 | 8 ± 3 | 24 |

[a]All improved lot samples for this step were below the 5 ng/mg limit of quantitation. A value of 5 ng/mg was used to estimate the reduction factor.

Figure 5:
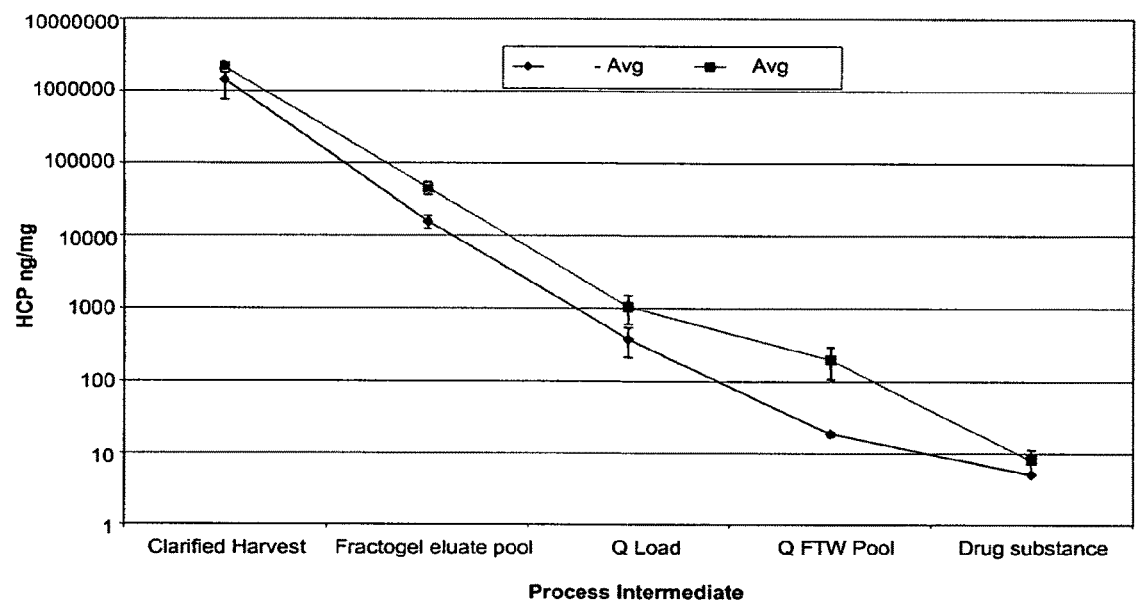
FIG. 5 shows a graphic depiction of the stepwise reduction in HCP for the average process B (diamond shape) and process A (square shape).

The comparison of HCP reduction in process B versus process A, plotted on a $\log_{10}$ scale, is displayed in FIG. 5. Process B exhibits lower HCP levels than process A at each intermediate step, including a 10-fold difference following the Q Sepharose step, indicating that the modifications to the Fractogel S and Q Sepharose chromatography steps improve process performance with respect to removal of HCPs.

Impact of the Capture and Fine Purification Operations on Processing Capacity

Two changes were introduced to increase the processing capacity of the capture and fine purification operations in process B. The first was the increase in the allowable load limit on the Fractogel S column from 30 g protein/L resin to 35 g protein/L resin at pH 7 and from 30 g protein/L resin to 70 g protein/L resin at pH 5. These changes allowed all of the filtered harvest material from the bioreactor to be loaded onto the Fractogel S column. The average load onto the Fractogel S column was approximately 9% higher in the improved process (at pH 7) than the load in the previous process (Table 16).

The second change was the removal of the requirement to fractionate the Phenyl Sepharose product peak with loads of less than 35 g protein/L resin. The fractionation resulted in discarding a significant portion of the product peak in order to adequately control host cell proteins. The changes implemented at the Fractogel S and Q Sepharose steps to control host cell proteins and procathepsin L levels rendered the fractionation of the Phenyl Sepharose peak unnecessary. This change allowed running three cycles of the Phenyl Sepharose column at a lower load range for process B resulting in a 12% increase in total load on the Phenyl Sepharose column compared with process A.

Table 16 compares the loads on the Fractogel S and the Phenyl Sepharose columns as well as the final drug substance amounts from the improved and previous processes. The improved process exhibits an approximate 8% overall increase in adalimumab yield for the three validation batches.

TABLE 16

Comparison of Fractogel S and Phenyl Sepharose column loads and drug substance yields in processes A and B

| Process | Fractogel S load[a] | Phenyl Sepharose load[a] | Drug substance yield[a] |
|---|---|---|---|
| Process A (n = 15) | 7641 ± 138 | 5947 ± 28 | 5290 ± 158 |
| Process B (n = 3) | 8375 ± 293 | 6752 ± 38 | 5748 ± 75 |
| Increase in process B | 9% | 12% | 8% |

[a]Load and yield are expressed in grams of protein

The improved method of purifying the antibody adalimumab improved clearance of HCP and procathepsin L (relative to process A), resulting in reduced levels in the drug substance. More specifically, in a comparison of drug substance lot release data, the following levels of HCP and procathepsin L were determined, as described in Table 17.

TABLE 17

Comparison of HCP and procathepsin L in processes A and B

| Assay | Lot release specification | Process A.1 | Process A.2 | Process A.3 | Process A.4 | Process B |
|---|---|---|---|---|---|---|
| Host cell protein (HCP) | ≤70 ng/mg | 46 ± 15 | 6 ± 3[b] | 22 ± 19 | 9 ± 4 | <5 |
| Procathepsin L | ≤5% | 18 ± 8[a] | <3.85[c] | 65 ± 23[=a] | <3.61[d] | <3.3[e] |

[a]Procathepsin L specification does not apply to process A.1; values provided for information only.

[b]14 of 17 lots below LOQ limit of 5 ng/mg; a value of 5 ng/mg used to calculate average and standard deviation.

[c]LOQ ranged from 3.30 to 3.85.

[d]LOQ ranged from 3.29 to 3.61.

[e]LOQ was 3.3 (LOQ = Limit of quantitation)

Extended characterization of the drug substance produced using the process B was performed. Drug substance from the three validation lots was analyzed and compared with an adalimumab reference standard, using the assays including amino acid analysis, circular dichroism, analytical centrifugation, QSTAR LC-mass spectrometry, non-reduced tryptic and LYS C peptide mapping with MS detection, free sulfhydryl assay, tryptic peptide mapping with MS detection, immunoblot, L929 bioassay, and BIAcore. All batches of drug substance manufactured by the improved process met the acceptance criteria and are comparable to the reference standard.

In sum, the performance of the process B has been demonstrated to be comparable to the process A at fermentation, capture and fine purification stages. Process B, however, exhibits improved capability with regard to reduction of host cell protein and procathepsin L, as well as an increase in capacity with regard to adalimumab yield. Drug substance release testing and extended characterization studies further demonstrate the comparability of the adalimumab drug substance produced by process B with that produced by process A.

TABLE 12

Overall improvement of HCP levels.

|   |   | Process A.1 (3 K) | | | Process A.2 (2 K) | | |
|---|---|---|---|---|---|---|---|
|   |   | A | B | C | D | E | F |
| 1 | Post depth filtration | 853,852 | 1,181,845 | 936,390 | 1,238,297 | 991,390 | 1,018,529 |
| 2 | Fractogel-S eluate | 6,739 | 15,772 | 16,286 | 17,528 | 15141 | 15426 |
| 3 | Conc. Fractogel-S eluate | 5980 | 13958 | 15361 | 14984 | 12769 | 434* |
|   |   | G | H | I | J | K | L |
| 4 | Viral inactivated filtrate | 2702 | 5074 | 5181 | 3826 | 3321 | 216 |
| 5 | Q Seph. FF flow through | 415 | 891 | 562 | 311 | 157 | 30 |
| 6 | Final UF/DF retentate | 36 | 83 | 43 | 20 | 7 | <LOQ |
|   | HCP Q reduction (fold) | 6.51 | 5.69 | 9.22 | 12.30 | 21.15 | 7.20 |

| Sample ID |   | Process A.3 (6 K) | | | Process A.4 (6 K) | | |
|---|---|---|---|---|---|---|---|
|   |   | M | N | O | P | Q | R |
| 7 | Post depth filtration | 2,039,630 | 2,150,284 | 2,125,986 | 2,026,000 | 2,517,074 | 1,867,919 |
| 8 | Fractogel-S eluate | 35,223 | 31,461 | 46,072 | 40,399 | 40,710 | 56,415 |
|   |   | Y | Z | A.A | A.B | A.C | A.D |
| 9 | Conc. Fractogel-S eluate | 1157 | NA | NA | 2,325 | 2,553 | 2,437 |
| 10 | Viral inactivated filtrate | 468 | 527 | 1,563 | 536 | 1,347 | 1,248 |
| 11 | Q Seph. FF flow through | 229 | 314 | 594 | 98 | 213 | 283 |
| 12 | Final UF/DF retentate | 23 | 33 | 48 | 5* | 8 | 11 |
|    | HCP Q reduction (fold) | 2.04 | 1.68 | 2.63 | 5.47 | 6.32 | 4.41 |

| Sample ID |   | Process B.1 (6 K) | | | Process B.2 (12 K) | | |
|---|---|---|---|---|---|---|---|
|   |   | S | T | U | V | W | X |
| 7 | Post depth filtration | 1,333,900 | 813,256 | 2,126,449 | 1,271,211 | 1,261,889 | 1,056,935 |
| 8 | Fractogel-S eluate | 12,430 | 19,150 | 15,257 | 9,558 | 13,130 | 17,427 |
|   |   | A.E | A.F | A.G |   |   |   |
| 9 | Conc. Fractogel-S eluate | N/A | N/A | N/A | 4824 | 771 | 526 |
| 10 | Viral inactivated filtrate | 554 | 220 | 371 | 1,317 | 376 | 255 |
| 11 | Q Seph. FF flow through | 18.5 | 20 | 17 | 14 | 3 | 0 |
| 12 | Final UF/DF retentate | 0.5 | 0 | 0 | 0 | 0 | 0 |

*lot was operated with delipid filter in the process.

TABLE 13

Overall improvements in procathepsin L levels.

| Sample ID | | Process A.1 (3 K) | | | Process A.2 (3 K) | | |
|---|---|---|---|---|---|---|---|
| | | Sample description | | | | | |
| | | A | B | C | D | E | F |
| 1 | Fractogel-S eluate | 54.07 | 51.23 | 61.04 | 42.19 | 50.14 | 48.28 |
| 2 | Conc. Fractogel-S eluate | 45.76 | 42.95 | 48.44 | 46.72 | 43.77 | 46.13 |
| | | G | H | I | J | K | L |
| 3 | Viral inactivated filtrate | 41.54 | 36.37 | 43.70 | 36.49 | 38.28 | 38.94 |
| 4 | Q Seph. FF flow through | 6.55 | 6.22 | 7.16 | 3.39 | 3.37 | 3.41 |
| 5 | Phenyl Seph FF eluate | 6.82 | 6.92 | 8.75 | 2.57 | 2.11 | 3.01 |
| 6 | Final UF/DF retentate | 9.85 | 9.77 | 9.69 | 1.84 | 2.93 | 3.00 |
| | Cathepsin L Activity Q reduction (fold) | 6.34 | 5.85 | 6.10 | 10.76 | 11.36 | 11.42 |

| Sample ID | | Process A.3 (6 K) | | | Process A.4 (3 K) | | |
|---|---|---|---|---|---|---|---|
| | | Sample description | | | | | |
| | | M | N | O | P | Q | R |
| 7 | Fractogel-S eluate | 98.26 | 77.10 | 106.41 | 97.42 | 84.91 | 94.14 |
| | Conc. Fractogel-S eluate | | | | 61.94 | 57.20 | 47.20 |
| | | Y | Z | A.A | A.B | A.C | A.D |
| 8 | Viral inactivated filtrate | 51.49 | 64.38 | 69.29 | 46.43 | 67.28 | 57.59 |
| 9 | Q Seph. FF flow through | 10.02 | 9.86 | 10.05 | 5.81 | 5.65 | 4.96 |
| 10 | Phenyl Seph FF eluate | 8.48 | 8.79 | 9.21 | 3.29 | 4.28 | 3.48 |
| 11 | Final UF/DF retentate | 6.68 | 8.76 | 8.54 | 3.28 | 3.46 | 3.71 |
| | Cathepsin L Activity Q reduction (fold) | 5.14 | 6.53 | 6.89 | 7.99 | 11.91 | 11.61 |

| Sample ID | | Process B.1 (6 K) | | | Process B.2 (12 K) | | |
|---|---|---|---|---|---|---|---|
| | | Sample description | | | | | |
| | | S | T | U | V | W | X |
| 7 | Fractogel-S eluate | 45.78 | 58.55 | 56.61 | 26.70 | 40.70 | 41.05 |
| | Conc. Fractogel-S eluate | | | | 22.20 | 42.80 | 35.53 |
| | | A.E | A.F | A.G | | | |
| 8 | Viral inactivated filtrate | 31.85 | 31.19 | 38.56 | 13.20 | 45.90 | 42.32 |
| 9 | Q Seph. FF flow through | 2.21 | 3.57 | 2.25 | 0.40 | 1.30 | 0.9 |
| 10 | Phenyl Seph FF eluate | | | | 1.00 | 1.30 | 0.85 |
| 11 | Final UF/DF retentate | 2.59 | 3.03 | 2.65 | 1.30 | 0.60 | 1.00 |
| | Cathepsin L Activity Q reduction (fold) | 14.41 | 8.74 | 17.14 | 33.00 | 35.31 | 47.02 |

Cathepsin L activitity: The unit used in red numbers is the fluorescent signal release rate described as RFU/sec./mg D2E7

Example 3

Assay for HCP Detection

The following example describes an HCP ELISA method for the determination of the residual Host Cell Protein (HCP) concentration in adalimumab drug substance samples obtained from process B, described in Example 2. Enzyme Linked Immunosorbent Assay (ELISA) was used to sandwich the sample comprising the HCP antigen between two layers of specific antibodies. This was followed by the blocking of non-specific sites with Casein. The sample was then incubated during which time the antigen molecules were captured by the first antibody (coating antibody Cygnus goat anti-CHO (Chinese Hamster Ovary), affinity purified). A second antibody (anti-CHO host cell protein biotinylated) was then added which fixed to the antigen (CHO host cell proteins) Importantly, the second antibody specific to the HCPs was produced from the cells used to generate the antibody. Neutravidin HRP-conjugated was added which binds to the biotinylated anti-CHO host cell protein. This was followed by the addition of K blue substrate. The chromogenic substrate was hydrolyzed by the bound enzyme conjugated antibody, producing a blue color. The reaction was stopped with 2 M $H_3PO_4$, changing color to yellow. Color intensity was directly proportional to the amount of antigen bound to the well. The HCP ELISA showed improvements for determining HCP levels in an antibody preparation than standard ELISA methods.

Example 4

Cathepsin L Kinetic Assay

A kinetic assay was developed and used to quantify cathepsin L activity for adalimumab manufacturing process intermediates of process B (see Example 2). The weak anion exchange HPLC assay (WAX-10 HPLC) used to measure HCP for drug substance release testing could not be used for this study since the variable protein content and buffer composition of the in-process samples may interfere with the method. The inability to directly quantitate procathepsin L in the process intermediates led to the development of an assay which measured the activity of cathepsin L by a kinetic fluorescence method. The kinetic assay, i.e., a high throughput fluorescent enzymatic method, has less interference for in-process samples than standard methods used to detect procathepsin L levels. The kinetic assay also provides a means for examining the reliability of the process for purifying adalimumab in-process samples described in Examples 1 and 2.

This method forces the activation of the procathepsin L in the samples to cathepsin L by addition of dextran sulfate. A fluorogenic peptide substrate, Z-leucine-arginine-AMC (7-amino-4-methyl coumarin), was used to detect cathepsin L activity at excitation 380 nm and emission 460 nm. The level of fluorescence activity in the samples was determined by the slope of the fluorogenic signal generated by the cleavage of the substrate per second. The range of this fluorescent activity assay was determined to be between 0.0144 to 1.04 RFU/sec. This activity was correlated to the amount of adalimumab present in the test sample; hence results are report as RFU/sec/mg adalimumab. Optimum activation conditions to achieve the maximum fluorescent signal were developed for each process intermediate sample using JMP software derived DOE experiments. The recommended activation conditions for this assay are summarized in Table 16.

Materials and Methods

Preparation of 500 mM DTT Stock Solution 7.7 grams of Ultrapure DTT (Invitrogen) was added into 90 mL of Milli-Q water and mixed until homogenous. The solution was topped up the solution with Milli-Q Water to a final volume of 100 mL. This 500 mM DTT stock was then aliquoted and stored at −80° C.

Preparation of the Activation Buffer (25 mM NaOAc, 5 mM DTT, 1 mM EDTA pH 5.5)

3.44 grams of sodium acetate (J. T. Baker), 0.38 grams of EDTA (J. T. Baker) and 950 mL Milli-Q water were added to a proper container and mixed until completely homogonous. The pH of the buffer was adjusted to 5.5 with 1 M HCl, and brought up to the final volume of 1 L in a volumetric flask. The buffer was filtered through a 0.22 μm filter and stored at 4° C. prior to use. 500 μL of DTT stock solution (500 mM described above) was added to 50 mL of buffer to a final concentration of 5 mM at the day of use.

Preparation of Dextran Sulfate +0.1% Sodium Azide stock solution 1 gram of dextran sulfate (EM Science) was added into 90 mL of Milli-Q water and mixed by until homogenous. 100 μL sodium azide was added from a 1 mg/mL stock solution (J. T. Baker). The solution was topped up to a final volume of 100 mL. This solution was then aliquoted and stored at −80° C.

Kinetic Assay Set-Up

Samples to be tested for cathepsin L activity require activation of the proenzyme (procathepsin L) to active enzyme (cathepsin L). This was accomplished by diluting samples in activation buffer, adding dextran sulfate and incubating at 37° C. for an appropriate time (details discussed in below). After activation, samples can be stored at −80° C. and remain stable. Optimal activation conditions determined for in-process samples are shown in Table 18.

TABLE 18

Summary of refined activation conditions for in-process samples

| Sample | Dilution | Dextran sulfate (μg/mL) | Activation time (hr) |
|---|---|---|---|
| Fractogel eluate | 700 | 0.035 | 6 |
| Q Sepharose Load | 700 | 0.035 | 6 |
| Q Sepharose FTW | 70 | 0.035 | 18 |
| Phenyl eluate | 200 | 0.035 | 6 |
| Drug substance | 600 | 0.035 | 6 |

On the day of testing, an aliquot of the test samples were removed from −80° C. and thawed in an ice bath. Once the test samples have thawed, (2×) 100 μL of each sample was loaded into a black polystyrene micro titer plate (Corning cat #3650). An aliquot of the Z-L-R-AMC Fluorogenic Peptide Substrate VII (R&D Systems) was thawed while protected from light. The substrate was diluted 1:1350 with the acetate buffer to a final concentration of 20 μM. 100 μL of the fluorogenic substrate was added to each well. The plate was then mixed for ~1 second and incubated at 37° C. for 3 minutes, while protected from light. The plate was then placed in the fluorescent plate reader that has been set to 37° C. The excitation wavelength was set to 380 nm and the emission was set to 460 nm. The fluorescence of each well was measured every 3 minutes for 30 minutes and the rate of substrate hydrolysis was calculated. The results, which take into consideration the dilution factor, were then divided by the adalimumab concentration for comparison. Results using this kinetic assay are described above in Example 2.

Adalimumab concentration was determined by $A_{280}$ using an extinction coefficient of 1.39. Adalimumab quantitation was performed on study samples using Poros A analysis. Sample dilutions were applied to achieve readings within the standard curve. A Shimadzu HPLC system was configured with a Poros A ImmunoDetection sensor cartridge (Applied Biosystems, Foster City, Calif.). The column was maintained at ambient temperature. The system was run at 2 mL/minute. The auto sampler tray temperature was set at 4° C. Absorbance was monitored at 280 nm. Buffer A was 1×PBS; buffer B was 0.1 M acetic acid and 150 mM sodium chloride. The sample was injected and Adalimumab was eluted using 100% buffer B.

Figure 6:
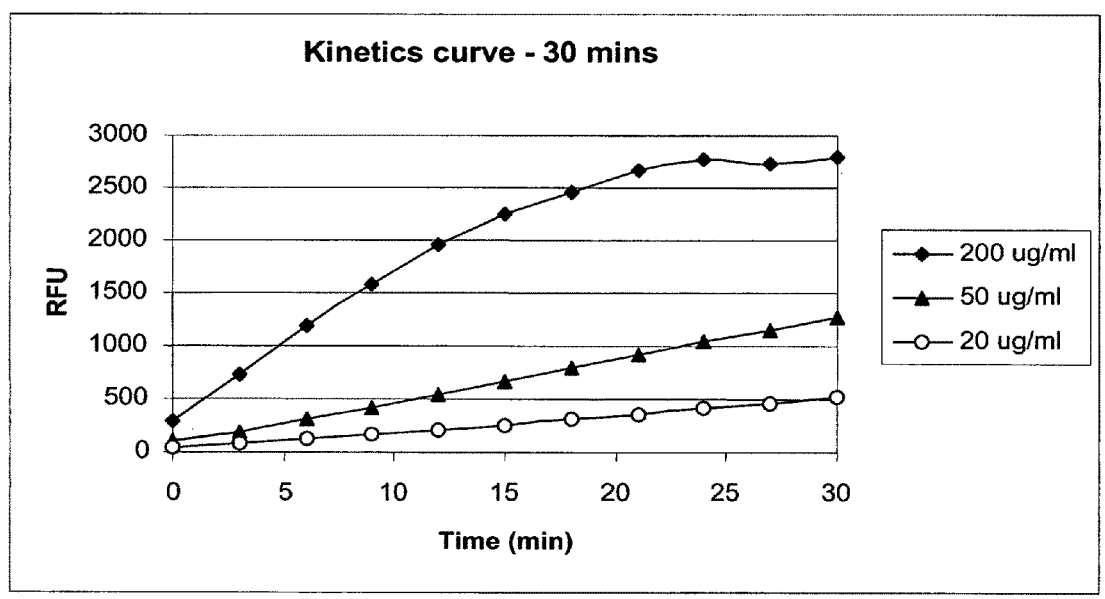
FIG. 6 shows that kinetic readings of activated in-process samples indicated the linear relationship of reaction time versus fluorescent signal.

The turnover of fluorogenic peptide using Fractogel load (sse first eluate Example 2; process B) from material obtained from CHO cell expression of adalimumab is shown in FIG. 6. This sample was diluted to 200, 50 and 20 μg/mL of adalimumab with activation buffer using 0.5 μg/mL dextran sulfate, and incubated at 37° C. for 16 hours. This lot at 50 and 20 μg/mL showed linear responses. The $R^2$ values are ≧0.99. However, the lot at 200 μg/mL shows nonlinear substrate turnover towards the end of the 30 minutes measurement time, resulting in a lower $R^2$ value of 0.91. Therefore, careful sample dilution is critical to maintain linear hydrolysis rates.

Assays were also performed to confirm that the kinetic assay using cathepsin activity to determine the level of procathepsin A were compliant with ICH guidelines, including precision analysis, including repeatbility precision. Furthermore, it was deteremined that the type of container, e.g., glass and polypropylene vials influences of cathepsin L activity. The results suggest that higher levels of cathepsin L are achieved when incubating in a polypropylene container as opposed to a glass container. In both cases, the addition of 0.5 μg/mL dextran sulfate was required for procathepsin L activation at pH 5.5.

In sum, the precision of the kinetic assay demonstrates that this assay is valid for detection of potential cathepsin L activity of adalimumab process intermediates.

This application is related to U.S. Pat. Nos. 6,090,382, 6,258,562, and 6,509,015. This application is also related to U.S. patent application Ser. No. 09/801,185, filed Mar. 7, 2001; U.S. patent application Ser. No. 10/302,356, filed Nov. 22, 2002; U.S. patent application Ser. No. 10/163657, filed Jun. 5, 2002; and U.S. patent application Ser. No. 10/133715, filed Apr. 26, 2002; U.S. patent application Ser. No. 10/222, 140, filed Aug. 16, 2002; U.S. patent application Ser. No. 10/693,233, filed Oct. 24, 2003; U.S. patent application Ser. No. 10/622,932, filed Jul. 18, 2003; U.S. patent application Ser. No. 10/623,039, filed Jul. 18, 2003; U.S. patent application Ser. No. 10/623,076, filed Jul. 18, 2003; U.S. patent application Ser. No. 10/623,065, filed Jul. 18, 2003; U.S. patent application Ser. No. 10/622,928, filed Jul. 18, 2003; U.S. patent application Ser. No. 10/623,075, filed Jul. 18, 2003; U.S. patent application Ser. No. 10/623,035, filed Jul. 18, 2003; U.S. patent application Ser. No. 10/622,683, filed Jul. 18, 2003; U.S. patent application Ser. No. 10/622,205, filed Jul. 18, 2003; U.S. patent application Ser. No. 10/622, 210, filed Jul. 18, 2003; and U.S. patent application Ser. No. 10/623,318, filed Jul. 18, 2003. This application is also related to PCT/US05/12007, filed Apr. 11, 2005. The entire contents of each of these patents and patent applications are hereby incorporated herein by reference.

Equivalents

Those skilled in the art will recognize, or be able to ascertain using no more than routine experimentation, many equivalents to the specific embodiments of the invention described herein. Such equivalents are intended to be encompassed by the following claims. The contents of all references, patents and published patent applications cited throughout this application are incorporated herein by reference.

What is claimed:

1. A host cell protein (HCP)-reduced antibody preparation produced by a method comprising:
applying a mixture comprising an antibody and at least one HCP to a cation exchange resin in an equilibration buffer, wherein greater than 30 grams of antibody per liter of cation exchange resin are applied;
washing HCP from the cation exchange resin with a plurality of wash steps comprising a first wash and a second wash, wherein there is an increase in conductivity from the first wash to the second wash;
eluting the antibody from the cation exchange resin with an elution buffer to form a first eluate;
applying the first eluate to an anion exchange resin, wherein prior to applying the first eluate to the anion exchange resin, pH and conductivity of the first eluate are adjusted to be substantially similar to pH and conductivity of the anion exchange resin; and
obtaining a first flowthrough comprising the antibody, such that the HCP-reduced antibody preparation is obtained, wherein the antibody is an isolated human anti-TNFα antibody that dissociates from human TNFα with a $K_d$ of $1 \times 10^{-8}$ M or less and a $K_{off}$ rate constant of $1 \times 10^{-3}$ $s^{-1}$ or less, both determined by surface plasmon resonance, and neutralizes human TNFα cytotoxicity in a standard in vitro L929 assay with an $IC_{50}$ of $1 \times 10^{-7}$ M or less, and wherein the HCP-reduced antibody preparation comprises no greater than about 70 ng of HCP per mg of antibody as measured by a HCP ELISA and a cathepsin L activity of no greater than about 3.0 RFU/s/mg antibody.

2. A pharmaceutical composition comprising the HCP-reduced antibody preparation of claim 1, and a pharmaceutically acceptable carrier.

3. A pharmaceutical composition comprising an isolated human anti-TNFα antibody that dissociates from human TNFα with a $K_d$ of $1 \times 10^{-8}$ M or less and a $K_{off}$ rate constant of $1 \times 10^{-3}$ $s^{-1}$ or less, both determined by surface plasmon resonance, and neutralizes human TNFα cytotoxicity in a standard in vitro L929 assay with an $IC_{50}$ of $1 \times 10^{-7}$ M or less, and a pharmaceutically acceptable carrier, wherein the composition contains a level of HCP no greater than about 70 ng of HCP per mg of antibody as measured by an HCP ELISA and a cathepsin L activity of no greater than about 3.0 RFU/s/mg antibody.

4. The pharmaceutical composition of claim 3, wherein the level of HCP comprises no greater than 13 ng of HCP per mg of antibody as measured by a HCP ELISA.

5. The pharmaceutical composition of claim 3, wherein the level of HCP comprises no greater than 5 ng of HCP per mg of antibody as measured by a HCP ELISA.

6. The pharmaceutical composition of claim 3, wherein the anti-TNFα antibody, or antigen-binding portion thereof, has the following characteristics:
   comprises a light chain variable region comprising a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9; a light chain CDR2 domain comprising the amino acid sequence of SEQ ID NO: 5; and a light chain CDR1 domain comprising the amino acid sequence of SEQ ID NO: 7; and
   comprises a heavy chain variable reason comprising a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12, a heavy chain CDR2 domain comprising the amino acid sequence of SEQ ID NO: 6, and a heavy chain CDR1 domain comprising the amino acid sequence of SEQ ID NO: 8.

7. The pharmaceutical composition of claim 3, wherein the anti-TNFα antibody, or antigen-binding portion thereof, comprises a light chain variable region (LCVR) comprising the amino acid sequence of SEQ ID NO: 1, and a heavy chain variable region (HCVR) comprising the amino acid sequence of SEQ ID NO: 2.

8. The pharmaceutical composition of claim 3, wherein the anti-TNFα antibody is adalimumab, or an antigen-binding portion thereof.

9. The pharmaceutical composition of claim 3, wherein the composition has an antibody concentration of 50 mg/mL.

10. An article of manufacture comprising a packaging material and an adalimumab formulation, wherein the adalimumab formulation comprises no greater than about 70 ng of HCP per mg of adalimumab as measured by an HCP ELISA and a cathepsin L activity of no greater than about 3.0 RFU/s/mg adalimumab.

11. The article of manufacture of claim 10, wherein the adalimumab formulation comprises no greater than 13 ng of HCP per mg of adalimumab.

12. The article of manufacture of claim 10, wherein the adalimumab formulation comprises no greater than 5 ng of HCP per mg of adalimumab.

13. The article of manufacture of claim 10, wherein the adalimumab formulation has an adalimumab concentration of 50 mg/mL.

* * * * *

UNITED STATES PATENT AND TRADEMARK OFFICE
CERTIFICATE OF CORRECTION

| | | |
|---|---|---|
| PATENT NO. | : 8,231,876 B2 | Page 1 of 1 |
| APPLICATION NO. | : 12/882601 | |
| DATED | : July 31, 2012 | |
| INVENTOR(S) | : Min Wan et al. | |

It is certified that error appears in the above-identified patent and that said Letters Patent is hereby corrected as shown below:

IN THE CLAIMS:

In column 131, claim 6, line 16 replace "heavy chain variable reason" with --heavy chain variable region--

Signed and Sealed this
Eighteenth Day of December, 2012

David J. Kappos
*Director of the United States Patent and Trademark Office*

SEQUENCE LISTING

```
<160> NUMBER OF SEQ ID NOS: 37

<210> SEQ ID NO 1
<211> LENGTH: 107
<212> TYPE: PRT
<213> ORGANISM: Artificial Sequence
<220> FEATURE:
<223> OTHER INFORMATION: adalimumab light chain variable region

<400> SEQUENCE: 1

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Tyr
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105

<210> SEQ ID NO 2
<211> LENGTH: 121
<212> TYPE: PRT
<213> ORGANISM: Artificial Sequence
<220> FEATURE:
<223> OTHER INFORMATION: adalimumab heavy chain variable region

<400> SEQUENCE: 2

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80
```

-continued

```
Leu Gln Met Asn Ser Leu Arg Ala Glu Asp Thr Ala Val Tyr Tyr Cys
                 85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120

<210> SEQ ID NO 3
<211> LENGTH: 9
<212> TYPE: PRT
<213> ORGANISM: Artificial Sequence
<220> FEATURE:
<223> OTHER INFORMATION: adalimumab light chain variable region CDR3
<221> NAME/KEY: VARIANT
<222> LOCATION: (9)
<223> OTHER INFORMATION: Xaa = Thr or Ala

<400> SEQUENCE: 3

Gln Arg Tyr Asn Arg Ala Pro Tyr Xaa
1               5

<210> SEQ ID NO 4
<211> LENGTH: 12
<212> TYPE: PRT
<213> ORGANISM: Artificial Sequence
<220> FEATURE:
<223> OTHER INFORMATION: adalimumab heavy chain variable region CDR3
<221> NAME/KEY: VARIANT
<222> LOCATION: (12)
<223> OTHER INFORMATION: Xaa = Tyr or Asn

<400> SEQUENCE: 4

Val Ser Tyr Leu Ser Thr Ala Ser Ser Leu Asp Xaa
1               5                   10

<210> SEQ ID NO 5
<211> LENGTH: 7
<212> TYPE: PRT
<213> ORGANISM: Artificial Sequence
<220> FEATURE:
<223> OTHER INFORMATION: adalimumab light chain variable region CDR2

<400> SEQUENCE: 5

Ala Ala Ser Thr Leu Gln Ser
1               5

<210> SEQ ID NO 6
<211> LENGTH: 17
<212> TYPE: PRT
<213> ORGANISM: Artificial Sequence
<220> FEATURE:
<223> OTHER INFORMATION: adalimumab heavy chain variable region CDR2

<400> SEQUENCE: 6

Ala Ile Thr Trp Asn Ser Gly His Ile Asp Tyr Ala Asp Ser Val Glu
1               5                   10                  15

Gly

<210> SEQ ID NO 7
<211> LENGTH: 11
<212> TYPE: PRT
<213> ORGANISM: Artificial Sequence
<220> FEATURE:
<223> OTHER INFORMATION: adalimumab light chain variable region CDR1

<400> SEQUENCE: 7
```

Arg Ala Ser Gln Gly Ile Arg Asn Tyr Leu Ala
1               5                   10

<210> SEQ ID NO 8
<211> LENGTH: 5
<212> TYPE: PRT
<213> ORGANISM: Artificial Sequence
<220> FEATURE:
<223> OTHER INFORMATION: adalimumab heavy chain variable region CDR1

<400> SEQUENCE: 8

Asp Tyr Ala Met His
1               5

<210> SEQ ID NO 9
<211> LENGTH: 107
<212> TYPE: PRT
<213> ORGANISM: Artificial Sequence
<220> FEATURE:
<223> OTHER INFORMATION: 2SD4 light chain variable region

<400> SEQUENCE: 9

Asp Ile Gln Met Thr Gln Ser Pro Ser Ser Leu Ser Ala Ser Ile Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Tyr
                85                  90                  95

Ala Phe Gly Gln Gly Thr Lys Val Glu Ile Lys
            100                 105

<210> SEQ ID NO 10
<211> LENGTH: 121
<212> TYPE: PRT
<213> ORGANISM: Artificial Sequence
<220> FEATURE:
<223> OTHER INFORMATION: 2SD4 heavy chain variable region

<400> SEQUENCE: 10

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Asp Trp Val
        35                  40                  45

Ser Ala Ile Thr Trp Asn Ser Gly His Ile Asp Tyr Ala Asp Ser Val
    50                  55                  60

Glu Gly Arg Phe Ala Val Ser Arg Asp Asn Ala Lys Asn Ala Leu Tyr
65                  70                  75                  80

Leu Gln Met Asn Ser Leu Arg Pro Glu Asp Thr Ala Val Tyr Tyr Cys
                85                  90                  95

Thr Lys Ala Ser Tyr Leu Ser Thr Ser Ser Ser Leu Asp Asn Trp Gly
            100                 105                 110

Gln Gly Thr Leu Val Thr Val Ser Ser
        115                 120

```
<210> SEQ ID NO 11
<211> LENGTH: 9
<212> TYPE: PRT
<213> ORGANISM: Artificial Sequence
<220> FEATURE:
<223> OTHER INFORMATION: 2SD4 light chain variable region CDR3

<400> SEQUENCE: 11

Gln Lys Tyr Asn Ser Ala Pro Tyr Ala
 1               5

<210> SEQ ID NO 12
<211> LENGTH: 9
<212> TYPE: PRT
<213> ORGANISM: Artificial Sequence
<220> FEATURE:
<223> OTHER INFORMATION: EP B12  light chain variable region CDR3

<400> SEQUENCE: 12

Gln Lys Tyr Asn Arg Ala Pro Tyr Ala
 1               5

<210> SEQ ID NO 13
<211> LENGTH: 9
<212> TYPE: PRT
<213> ORGANISM: Artificial Sequence
<220> FEATURE:
<223> OTHER INFORMATION: VL10E4 light chain variable region CDR3

<400> SEQUENCE: 13

Gln Lys Tyr Gln Arg Ala Pro Tyr Thr
 1               5

<210> SEQ ID NO 14
<211> LENGTH: 9
<212> TYPE: PRT
<213> ORGANISM: Artificial Sequence
<220> FEATURE:
<223> OTHER INFORMATION: VL100A9 light chain variable region CDR3

<400> SEQUENCE: 14

Gln Lys Tyr Ser Ser Ala Pro Tyr Thr
 1               5

<210> SEQ ID NO 15
<211> LENGTH: 9
<212> TYPE: PRT
<213> ORGANISM: Artificial Sequence
<220> FEATURE:
<223> OTHER INFORMATION: VLL100D2 light chain variable region CDR3

<400> SEQUENCE: 15

Gln Lys Tyr Asn Ser Ala Pro Tyr Thr
 1               5

<210> SEQ ID NO 16
<211> LENGTH: 9
<212> TYPE: PRT
<213> ORGANISM: Artificial Sequence
<220> FEATURE:
<223> OTHER INFORMATION: VLL0F4 light chain variable region CDR3

<400> SEQUENCE: 16

Gln Lys Tyr Asn Arg Ala Pro Tyr Thr
 1               5
```

```
<210> SEQ ID NO 17
<211> LENGTH: 9
<212> TYPE: PRT
<213> ORGANISM: Artificial Sequence
<220> FEATURE:
<223> OTHER INFORMATION: LOE5 light chain variable region CDR3

<400> SEQUENCE: 17

Gln Lys Tyr Asn Ser Ala Pro Tyr Tyr
 1               5

<210> SEQ ID NO 18
<211> LENGTH: 9
<212> TYPE: PRT
<213> ORGANISM: Artificial Sequence
<220> FEATURE:
<223> OTHER INFORMATION: VLLOG7 light chain variable region CDR3

<400> SEQUENCE: 18

Gln Lys Tyr Asn Ser Ala Pro Tyr Asn
 1               5

<210> SEQ ID NO 19
<211> LENGTH: 9
<212> TYPE: PRT
<213> ORGANISM: Artificial Sequence
<220> FEATURE:
<223> OTHER INFORMATION: VLLOG9 light chain variable region CDR3

<400> SEQUENCE: 19

Gln Lys Tyr Thr Ser Ala Pro Tyr Thr
 1               5

<210> SEQ ID NO 20
<211> LENGTH: 9
<212> TYPE: PRT
<213> ORGANISM: Artificial Sequence
<220> FEATURE:
<223> OTHER INFORMATION: VLLOH1 light chain variable region CDR3

<400> SEQUENCE: 20

Gln Lys Tyr Asn Arg Ala Pro Tyr Asn
 1               5

<210> SEQ ID NO 21
<211> LENGTH: 9
<212> TYPE: PRT
<213> ORGANISM: Artificial Sequence
<220> FEATURE:
<223> OTHER INFORMATION: VLLOH10 light chain variable region CDR3

<400> SEQUENCE: 21

Gln Lys Tyr Asn Ser Ala Ala Tyr Ser
 1               5

<210> SEQ ID NO 22
<211> LENGTH: 9
<212> TYPE: PRT
<213> ORGANISM: Artificial Sequence
<220> FEATURE:
<223> OTHER INFORMATION: VL1B7 light chain variable region CDR3

<400> SEQUENCE: 22

Gln Gln Tyr Asn Ser Ala Pro Asp Thr
 1               5

<210> SEQ ID NO 23
<211> LENGTH: 9
```

```
<212> TYPE: PRT
<213> ORGANISM: Artificial Sequence
<220> FEATURE:
<223> OTHER INFORMATION: VL1C1 light chain variable region CDR3

<400> SEQUENCE: 23

Gln Lys Tyr Asn Ser Asp Pro Tyr Thr
1               5

<210> SEQ ID NO 24
<211> LENGTH: 9
<212> TYPE: PRT
<213> ORGANISM: Artificial Sequence
<220> FEATURE:
<223> OTHER INFORMATION: VL0.1F4 light chain variable region CDR3

<400> SEQUENCE: 24

Gln Lys Tyr Ile Ser Ala Pro Tyr Thr
1               5

<210> SEQ ID NO 25
<211> LENGTH: 9
<212> TYPE: PRT
<213> ORGANISM: Artificial Sequence
<220> FEATURE:
<223> OTHER INFORMATION: VL0.1H8 light chain variable region CDR3

<400> SEQUENCE: 25

Gln Lys Tyr Asn Arg Pro Pro Tyr Thr
1               5

<210> SEQ ID NO 26
<211> LENGTH: 9
<212> TYPE: PRT
<213> ORGANISM: Artificial Sequence
<220> FEATURE:
<223> OTHER INFORMATION: L0E7.A light chain variable region CDR3

<400> SEQUENCE: 26

Gln Arg Tyr Asn Arg Ala Pro Tyr Ala
1               5

<210> SEQ ID NO 27
<211> LENGTH: 12
<212> TYPE: PRT
<213> ORGANISM: Artificial Sequence
<220> FEATURE:
<223> OTHER INFORMATION: 2SD4 heavy chain variable region CDR3

<400> SEQUENCE: 27

Ala Ser Tyr Leu Ser Thr Ser Ser Ser Leu Asp Asn
1               5                   10

<210> SEQ ID NO 28
<211> LENGTH: 12
<212> TYPE: PRT
<213> ORGANISM: Artificial Sequence
<220> FEATURE:
<223> OTHER INFORMATION: VH1B11 heavy chain variable region CDR3

<400> SEQUENCE: 28

Ala Ser Tyr Leu Ser Thr Ser Ser Ser Leu Asp Lys
1               5                   10

<210> SEQ ID NO 29
<211> LENGTH: 12
<212> TYPE: PRT
<213> ORGANISM: Artificial Sequence
```

```
<220> FEATURE:
<223> OTHER INFORMATION: VH1D8 heavy chain variable region CDR3

<400> SEQUENCE: 29

Ala Ser Tyr Leu Ser Thr Ser Ser Ser Leu Asp Tyr
1               5                   10

<210> SEQ ID NO 30
<211> LENGTH: 12
<212> TYPE: PRT
<213> ORGANISM: Artificial Sequence
<220> FEATURE:
<223> OTHER INFORMATION: VH1A11 heavy chain variable region CDR3

<400> SEQUENCE: 30

Ala Ser Tyr Leu Ser Thr Ser Ser Ser Leu Asp Asp
1               5                   10

<210> SEQ ID NO 31
<211> LENGTH: 12
<212> TYPE: PRT
<213> ORGANISM: Artificial Sequence
<220> FEATURE:
<223> OTHER INFORMATION: VH1B12 heavy chain variable region CDR3

<400> SEQUENCE: 31

Ala Ser Tyr Leu Ser Thr Ser Phe Ser Leu Asp Tyr
1               5                   10

<210> SEQ ID NO 32
<211> LENGTH: 12
<212> TYPE: PRT
<213> ORGANISM: Artificial Sequence
<220> FEATURE:
<223> OTHER INFORMATION: VH1E4 heavy chain variable region CDR3

<400> SEQUENCE: 32

Ala Ser Tyr Leu Ser Thr Ser Ser Ser Leu His Tyr
1               5                   10

<210> SEQ ID NO 33
<211> LENGTH: 12
<212> TYPE: PRT
<213> ORGANISM: Artificial Sequence
<220> FEATURE:
<223> OTHER INFORMATION: VH1F6 heavy chain variable region CDR3

<400> SEQUENCE: 33

Ala Ser Phe Leu Ser Thr Ser Ser Ser Leu Glu Tyr
1               5                   10

<210> SEQ ID NO 34
<211> LENGTH: 12
<212> TYPE: PRT
<213> ORGANISM: Artificial Sequence
<220> FEATURE:
<223> OTHER INFORMATION: 3C-H2 heavy chain variable region CDR3

<400> SEQUENCE: 34

Ala Ser Tyr Leu Ser Thr Ala Ser Ser Leu Glu Tyr
1               5                   10

<210> SEQ ID NO 35
<211> LENGTH: 12
<212> TYPE: PRT
<213> ORGANISM: Artificial Sequence
<220> FEATURE:
<223> OTHER INFORMATION: VH1-D2.N heavy chain variable region CDR3
```

```
<400> SEQUENCE: 35

Val Ser Tyr Leu Ser Thr Ala Ser Ser Leu Asp Asn
 1               5                   10

<210> SEQ ID NO 36
<211> LENGTH: 321
<212> TYPE: DNA
<213> ORGANISM: Artificial Sequence
<220> FEATURE:
<223> OTHER INFORMATION: adalimumab light chain variable region

<400> SEQUENCE: 36
gacatccaga tgacccagtc tccatcctcc ctgtctgcat ctgtagggga cagagtcacc      60
atcacttgtc gggcaagtca gggcatcaga aattacttag cctggtatca gcaaaaacca    120
gggaaagccc ctaagctcct gatctatgct gcatccactt tgcaatcagg ggtcccatct    180
cggttcagtg gcagtggatc tgggacagat ttcactctca ccatcagcag cctacagcct    240
gaagatgttg caacttatta ctgtcaaagg tataaccgtg caccgtatac ttttggccag    300
gggaccaagg tggaaatcaa a                                              321

<210> SEQ ID NO 37
<211> LENGTH: 363
<212> TYPE: DNA
<213> ORGANISM: Artificial Sequence
<220> FEATURE:
<223> OTHER INFORMATION: adalimumab heavy chain variable region

<400> SEQUENCE: 37
gaggtgcagc tggtggagtc tgggggaggc ttggtacagc ccggcaggtc cctgagactc      60
tcctgtgcgg cctctggatt cacctttgat gattatgcca tgcactgggt ccggcaagct    120
ccagggaagg gcctggaatg ggtctcagct atcacttgga atagtggtca catagactat    180
gcggactctg tggagggccg attccaccatc tccagagaca cgccaagaa ctccctgtat    240 ctgcaaatga acagtctgag agctgaggat acggccgtat attactgtgc gaaagtctcg    300
taccttagca ccgcgtcctc ccttgactat tggggccaag gtaccctggt caccgtctcg    360
agt                                                                  363
```